United States Patent
Schobel et al.

(10) Patent No.: US 12,403,090 B2
(45) Date of Patent: Sep. 2, 2025

(54) ORAL FILM COMPOSITIONS AND DOSAGE FORMS HAVING PRECISE ACTIVE DISSOLUTION PROFILES

(71) Applicant: Aquestive Therapeutics, Inc., Warren, NJ (US)

(72) Inventors: Alexander Mark Schobel, Vero Beach, FL (US); Stephen Wargacki, Pittstown, NJ (US); Vincent J. Buono, Basking Ridge, NJ (US); Susan Shumard, Green Brook, NJ (US); Christopher James Santee, Portage, IN (US)

(73) Assignee: Aquestive Therapeutics, Inc., Warren, NJ (US)

( * ) Notice: Subject to any disclaimer, the term of this patent is extended or adjusted under 35 U.S.C. 154(b) by 0 days.

(21) Appl. No.: 17/989,307

(22) Filed: Nov. 17, 2022

(65) Prior Publication Data
US 2023/0149304 A1 May 18, 2023

Related U.S. Application Data

(63) Continuation of application No. 16/561,573, filed on Sep. 5, 2019, now Pat. No. 11,541,002.

(60) Provisional application No. 62/732,720, filed on Sep. 18, 2018, provisional application No. 62/728,187, filed on Sep. 7, 2018.

(51) Int. Cl.
*A61K 9/00* (2006.01)
*A61K 31/5513* (2006.01)
*A61P 25/08* (2006.01)

(52) U.S. Cl.
CPC .......... *A61K 9/006* (2013.01); *A61K 31/5513* (2013.01); *A61P 25/08* (2018.01)

(58) Field of Classification Search
None
See application file for complete search history.

(56) References Cited

U.S. PATENT DOCUMENTS

| | | |
|---|---|---|
| 4,631,837 A | 12/1986 | Magoon |
| 6,552,017 B1 | 4/2003 | Robichaud et al. |
| 6,713,471 B1 | 3/2004 | Robichaud et al. |
| 7,071,186 B2 | 7/2006 | Robichaud et al. |
| 7,183,282 B2 | 2/2007 | Robichaud et al. |
| RE39,680 E | 6/2007 | Robichaud et al. |
| 7,357,891 B2 | 4/2008 | Yang et al. |
| 7,425,292 B2 | 9/2008 | Yang et al. |
| 7,666,337 B2 | 2/2010 | Yang et al. |
| 8,012,505 B2 | 9/2011 | Houghton et al. |
| 8,017,150 B2 | 9/2011 | Yang et al. |
| 8,309,722 B2 | 11/2012 | Tomesch et al. |
| 8,598,119 B2 | 12/2013 | Mates et al. |
| 8,603,514 B2 | 12/2013 | Yang et al. |
| 8,648,077 B2 | 2/2014 | Tomesch et al. |
| 8,652,378 B1 | 2/2014 | Yang et al. |
| 8,663,667 B2 | 3/2014 | Bui et al. |
| 8,765,167 B2 | 7/2014 | Myers et al. |
| 8,779,139 B2 | 7/2014 | Tomesch et al. |
| 8,900,497 B2 | 12/2014 | Yang et al. |
| 8,900,498 B2 | 12/2014 | Yang et al. |
| 8,936,825 B2 | 1/2015 | Myers et al. |
| 8,956,685 B2 | 2/2015 | Bogue et al. |
| 8,993,572 B2 | 3/2015 | Mates et al. |
| 9,108,340 B2 | 8/2015 | Yang et al. |
| 9,168,258 B2 | 10/2015 | Mates et al. |
| 9,315,504 B2 | 4/2016 | Tomesch et al. |
| 9,371,324 B2 | 6/2016 | Mates et al. |
| 9,428,506 B2 | 8/2016 | Mates et al. |
| 9,586,960 B2 | 3/2017 | Tomesch et al. |
| 9,616,061 B2 | 4/2017 | Mates et al. |
| 9,708,322 B2 | 7/2017 | Li et al. |
| 9,745,300 B2 | 8/2017 | Mates et al. |
| 9,751,883 B2 | 9/2017 | Tomesch et al. |
| 9,855,221 B2 | 1/2018 | Myers et al. |
| 9,931,305 B2 | 4/2018 | Yang et al. |
| 10,744,086 B2 | 8/2020 | Lim et al. |
| 10,857,097 B2 | 12/2020 | Lim et al. |
| 2004/0034015 A1 | 2/2004 | Robichaud et al. |
| 2004/0228919 A1 | 11/2004 | Houghton et al. |
| 2005/0037055 A1 | 2/2005 | Yang et al. |

(Continued)

FOREIGN PATENT DOCUMENTS

| | | |
|---|---|---|
| CN | 1758899 A | 4/2006 |
| CN | 102933207 A | 2/2013 |

(Continued)

OTHER PUBLICATIONS

Rajni Bala et al., Design Optimization and In Vitro-In Vivo Evaluation of Orally Dissolving Strips of Clobazam, 2014, Journal of Drug Delivery, Article ID 392783, pp. 1-15 (Year: 2014).*
Aprea, E. et al., "Volatile Compounds of Raspberry Fruit: From Analytical Methods to Biological Role and Sensory Impact," Molecules 2015, vol. 20, 2445-2474.
PION Rainbow Dynamic Dissolution Monitor (https://pion.com.cn/dissolution/compendial-dissolution/rainbow/) (5 pages).
International Search Report issued in PCT/US2019/049725, dated Jan. 28, 2020 (5 pages).

(Continued)

*Primary Examiner* — Nannette Holloman
(74) *Attorney, Agent, or Firm* — Hoffmann & Baron, LLP

(57) ABSTRACT

An oral film in an individual unit dose for delivery of one or more actives is disclosed herein, the film having a precisely calculated and controlled active dissolution profile. A wide variety of actives may be used, including, for example, clobazam, diazepam, or riluzole. Also disclosed are methods of treating a variety of diseases and conditions, for example, epilepsy and seizures, by administering the oral film disclosed herein.

14 Claims, 12 Drawing Sheets

(11 of 12 Drawing Sheet(s) Filed in Color)

(56) References Cited

U.S. PATENT DOCUMENTS

| | | | |
|---|---|---|---|
| 2005/0281772 | A1 | 12/2005 | Bromley et al. |
| 2012/0219628 | A1 | 8/2012 | Lim et al. |
| 2012/0263865 | A1 | 10/2012 | Bogue |
| 2013/0156823 | A1* | 6/2013 | Wu .................... A61K 31/5513 424/45 |
| 2014/0178473 | A1 | 6/2014 | Lim et al. |
| 2015/0072964 | A1 | 3/2015 | Mates et al. |
| 2015/0080404 | A1 | 3/2015 | Mates et al. |
| 2016/0310502 | A1 | 10/2016 | Vanover et al. |
| 2017/0056374 | A1 | 3/2017 | Lee et al. |
| 2017/0114037 | A1 | 4/2017 | Davis et al. |
| 2017/0183350 | A1 | 6/2017 | Mates et al. |
| 2017/0189398 | A1 | 7/2017 | Mates et al. |
| 2017/0290776 | A1 | 10/2017 | Schobel et al. |
| 2017/0348251 | A1 | 12/2017 | Schobel et al. |
| 2017/0360942 | A1* | 12/2017 | Myers .................... A61P 23/00 |
| 2018/0280518 | A1 | 10/2018 | Myers et al. |
| 2020/0000773 | A1 | 1/2020 | Lee et al. |
| 2020/0046637 | A1 | 2/2020 | Lim et al. |
| 2023/0086496 | A1 | 3/2023 | Lim et al. |

FOREIGN PATENT DOCUMENTS

| | | | |
|---|---|---|---|
| CN | 105193772 | A | 12/2015 |
| JP | 2013253039 | A * | 12/2013 |
| WO | 2004075875 | A1 | 9/2004 |
| WO | 2011053251 | A1 | 5/2011 |
| WO | 2017192923 | A1 | 11/2017 |

OTHER PUBLICATIONS

Written Opinion of the International Searching Authority issued in PCT/US2019/049725, dated Jan. 28, 2020 (5 pages).

Rajni Bala et al., Design Optimization and In Vitro-In Vivo Evaluation of Orally Dissolving Strips of Clobazam, 2014, Journal of Drug Delivery, vol. 2014, Article ID 392783, pp. 1-15 (Year: 2014).

Meng Shengnan et al., Pharmaceutics, Shanghai Scientific & Technical Publishers, pp. 81-83, published on Sep. 30, 2011 (in Chinese with English machine translation).

First Office Action for Chinese Application No. 201980073077.2 dated Apr. 20, 2023 (in Chinese with English translation).

Communication pursuant to Article 94(3) EPC for European Patent Application No. 19 797 399.3-1112 dated Mar. 28, 2023.

Preliminary Office Action for Brazilian Patent Application No. BR112021004053-6 dated Jun. 5, 2023 (in Portuguese with Informal English Translation).

Official Action (Dispatch Date Jul. 6, 2023) for Japanese Patent Application No. 2021-512652 in Japanese with English machine translation.

Foo, Wen Chin et al., A novel unit-dose approach for the pharmaceutical compounding of an orodispersible film, Int J Pharm. Mar. 25, 2018;539(1-2) : 165-174. doi: 10.1016/j. ijpharm.2018.01.047. Epub Feb. 27, 2018.

Office Action issued by the Canadian Intellectual Property Office (CIPO) dated Dec. 8, 2023 for Canadian Patent Application No. 3,110,997.

International Preliminary Report on Patentability (Chapter I) issued by the International Bureau of WIPO on behalf of the International Searching Authority for International application No. PCT/US2019/ 049725, Date of issuance of the report: Mar. 9, 2021.

Second Office Action issued by the China National Intellectual Property Administration for Chinese Application No. 201980073077.2 dated Dec. 7, 2023 (in Chinese with English translation).

Decision on Rejection issued by the China National Intellectual Property Administration for Chinese Application No. 201980073077.2 dated May 9, 2024 (in Chinese with English translation).

Official Action (Dispatch Date: Apr. 25, 2024) issued by the Japan Patent Office for Japanese Patent Application No. 2021-512652 (in Japanese with English machine translation and with a Brief summary of Official Action in English).

Pre-grant Opposition Petition filed Feb. 28, 2024 with the National Institute of Industrial Property—INPI by EMS S.A. for Brazilian Patent Application No. BR 11 2021 004053 6 (in Portuguese with English Translation).

Pre-grant Opposition Petition filed Sep. 20, 2024 with the National Institute of Industrial Property—INPI by Biolab Sanus Farmacêutica Ltda. for Brazilian Patent Application No. BR 11 2021 004053 6 (in Portuguese with English Translation).

Shen, Bao-De et al., Development and characterization of an orodispersible film containing drug nanoparticles, European Journal of Pharmaceutics and Biopharmaceutics, vol. 85, Issue 3, Part B, Nov. 2013, pp. 1348-1356, https://doi.org/10.1016/j.ejpb.2013.09. 019.

Office Action issued in U.S. Appl. No. 16/561,573, mail date Jun. 22, 2021.

Office Action issued in U.S. Appl. No. 16/561,573, mail date Apr. 12, 2022.

Office Action issued in U.S. Appl. No. 18/091,556, mail date Mar. 9, 2023.

Office Action issued in U.S. Appl. No. 18/091,556, mail date Nov. 21, 2023.

Communication pursuant to Article 94(3) EPC from the European Patent Office for European Patent Application No. 19 797 399.3- 1109 dated Dec. 4, 2024.

Official Action (Dispatch Date: Jul. 6, 2023) for Japanese Patent Application No. 2021-512652 in Japanese with English Summary of the Official Action.

English Summary of Official Action (Dispatch Date: Jul. 6, 2023) for Japanese Patent Application No. 2021-512652.

Office Action issued by the Canadian Intellectual Property Office (CIPO) dated Feb. 6, 2025 for Canadian Patent Application No. 3,110,997.

* cited by examiner

ORAL FILM COMPOSITIONS AND DOSAGE FORMS HAVING PRECISE ACTIVE DISSOLUTION PROFILES

CROSS-REFERENCE TO RELATED APPLICATIONS

This application is a continuation of U.S. application Ser. No. 16/561,573, filed on Sep. 5, 2019, which issued as U.S. Pat. No. 11,541,002 B2 on Jan. 3, 2023, which U.S. application Ser. No. 16/561,573 claims the benefit of U.S. Provisional Application No. 62/728,187, filed on Sep. 7, 2018, and U.S. Provisional Application No. 62/732,720, filed on Sep. 18, 2018. The contents of each of these aforementioned applications are incorporated herein by reference in their entirety.

FIELD OF THE DISCLOSURE

The present disclosure relates to an oral film in an individual unit dose for delivery of one or more actives, such as clobazam, having an average particle size D90 of less than about 160 microns, wherein the oral film has a precise, controlled active dissolution rate, and methods of treating a variety of diseases, including epilepsy and seizures, by administering the same to a patient in need thereof.

BACKGROUND

Active ingredients, such as drugs or pharmaceuticals, may be prepared in a tablet form to allow for accurate and consistent dosing. However, this form of preparing and dispensing medications has many disadvantages including that a large proportion of adjuvants that must be added to obtain a size able to be handled, that a larger medication form requires additional storage space, and that dispensing includes counting the tablets which has a tendency for inaccuracy. In addition, many persons, estimated to be as much as 28% of the population, have difficulty swallowing tablets. While tablets may be broken into smaller pieces or even crushed as a means of overcoming swallowing difficulties, this is not a suitable solution for many tablet or pill forms. For example, crushing or destroying the tablet or pill form to facilitate ingestion, alone or in admixture with food, may also destroy the controlled release properties.

As an alternative to tablets and pills, films may be used to carry active ingredients such as drugs, pharmaceuticals, and the like. However, historically films and the process of making drug delivery systems using this dosage form have presented some unique challenges, both in the formulation, processing and pharmacokinetic areas. In particular, films and oral dosage units cut therefrom have suffered from a number of unfavorable characteristics that have not allowed them to be used in practice, until recent years when advancements have made film a highly desirable dosage form.

As with traditional tablets and pills, the absorption of drugs administered in the form of oral films depends on a number of factors, including the release of the drug substance from the film, the dissolution, and solubilization of the drug under physiological conditions. In one manner, in vitro dissolution is a relevant predictor of in vivo performance. In vitro dissolution tests for immediate release oral dosage forms are used to assess the quality of a drug product between lots; guide development of new formulations; and ensure continuing product quality, bioequivalence, and performance as changes are made to the product.

Because oral films dissolve rapidly, there is a need for improved dissolution testing that is capable of precise measurements almost immediately upon placement in a liquid and at very small time intervals for these rapid dissolving products.

SUMMARY

An oral film for delivery of a desired amount of an active having an average particle size D90 of less than about 160 microns in an individual unit dose is disclosed. The film comprises: a water-soluble polymer matrix, a water swellable polymer matrix, or a water-soluble and water swellable polymer matrix; and an additive. The active may be chosen from a wide variety of actives, such as those disclosed herein, including clobazam, riluzole, diazepam, or any combination thereof. The additive may be selected from the group consisting of a sweetener, a flavor, a flavor enhancer, a filler, a plasticizer, a dye, a pigment, a permeation enhancer, a buffer, a preservative, silicon dioxide, an anti-tacking agent, and any combination thereof. Upon placing the film in a medium, more than about 2% of the active is dissolved in the medium after about 3 minutes.

The active has an average particle size D90 of less than about 160 microns, less than about 120 microns, less than about 100 microns, less than about 80 microns, less than about 50 microns, less than about 20 microns, less than about 10 microns, or D90 of about 8 microns. Optionally, the active also has an average particle size D50 of less than about 30, less than about 20, less than about 10, less than about 4, or a D50 of about 3, and/or an average particle size D10 of less than about 10, less than about 5, less than about 2, or D10 of about 1.

When the active is clobazam, the individual unit dose may contain about 2 mg to about 20 mg, about 5 mg, or about 20 mg of clobazam. Optionally, less than about 10% of the active is dissolved in the oral film. In certain embodiments, upon placing the film in a medium, more than about 20% of the active is dissolved after about 3 minutes, about 30% of the active is dissolved after about 3 minutes, about 30% of the active is dissolved after about 1 minute, more than about 50% of the active is dissolved after about 1 minute, more than about 95% of the active is dissolved after about 2.5 minutes, more than about 40% of the active is dissolved after about 3.5 minutes, more than about 55% of the active is dissolved after about 5 minutes, more than about 75% of the active is dissolved after about 5 minutes, more than about 85% of the active is dissolved after about 6.5 minutes, or more than about 95% of the active is dissolved in the medium after about 10 minutes. In certain embodiments thereof, dissolution of the active is measured after storage of the film for more than 0 to about 36 months, at about 20° C. to about 60° C., and/or up to about 75% relative humidity (RH), or about 60% RH.

The oral film may contain a sweetener selected from the group consisting of: sucralose, *stevia*, acesulfame potassium, saccharin, fructose, aspartame, and any combination thereof, optionally present in about 0.5% to about 5% by weight of the composition. The oral film may contain berry flavoring, optionally present in about 0.1% to about 15% by weight of the composition.

A method of treating epilepsy and seizures by administering an oral film containing an active in an individual unit dose to a human in need thereof is also disclosed.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

Figure 1:
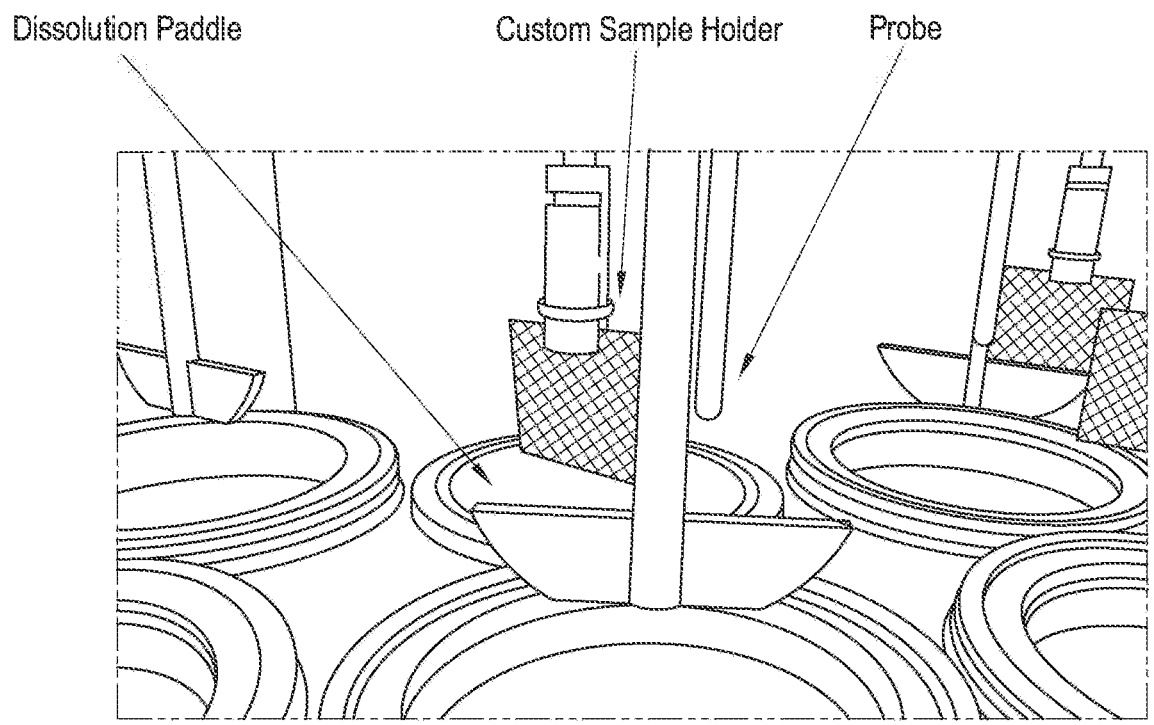
FIGS. 1 and 2 are exemplary configurations of systems used in PION technology.

Dissolution profiles, and, more specifically, dissolution rates, for drug products, including oral films, and actives are established to ensure consistency between batches and to identify any potential issues with bioavailability of a pharmaceutical active. A surprising new means for more precisely and accurately testing dissolution profiles was developed using PION technology, a fiber optic UV monitoring system.

An oral film for delivery of a desired amount of an active having an average particle size D90 of less than about 160 microns in an individual unit dose is disclosed herein, having an active dissolution profile with improved precision, more sampling points and enhanced rate of change evaluation as compared to prior dissolution tests and profiles currently known with respect to film dosage forms.

The oral film in an individual unit dose (i.e., dosage unit) disclosed herein contains: a water-soluble polymer matrix, a water swellable polymer matrix, or a water-soluble and water swellable polymer matrix; optionally micronized active; and one or more additives. The film is self-supporting and the active is substantially uniformly distributed within the film. The substantially uniform distribution is measured by substantially equally sized individual unit doses that do not vary by more than 10% of the desired amount of the active. The film containing the active may be made by casting methods as described in, for example, U.S. Pat. Nos. 7,666,337; 8,603,514; 8,765,167; 9,855,221; and 9,931,305, all incorporated herein by reference in their entirety, and then cut into individual unit doses (dosage units). Alternatively, the individual unit doses may be made in individual wells or strips, such as disclosed in U.S. Pat. Nos. 8,956,685; 8,936,825; and U.S. Publication US2012/0263865, all incorporated herein by reference in their entirety.

The term "film" can include films and sheets, in any shape, including rectangular, square, or other desired shape. A film can be any desired thickness and size. In an embodiment, a film can have a thickness and size such that it can be administered to a patient, for example, by placement into the oral cavity. A film can be relatively thin from about 0.0025 mm to about 0.250 mm, or a film can be somewhat thicker from about 0.250 mm to about 1.0 mm. Some films may be even thicker, e.g., greater than about 1.0 mm, or thinner, e.g., less than about 0.0025 mm. A film can be a single layer or a film can be multi-layered, including laminated or multiple cast films. When multilayered, the active may be present in one layer, in more than one layer but not all layers, or in all layers. The active may be present in the mucosal-contacting layer. An active may be combined, with one or more additives, in a single layer, each contained in separate layers, or can each be otherwise contained in discrete regions of the same dosage form.

Active

The films may be processed to ensure that any active(s) are substantially uniformly distributed throughout. For example, when the films, such as cast films, are cut into individual unit doses which are substantially the same size, the amount of the active in the unit dose can be known with a great deal of accuracy. The accuracy in dose is particularly advantageous and in fact required by governmental regulatory bodies such as the U.S. FDA, when the active is a medicament, i.e., a drug.

The active that may be incorporated into the film of the present invention include, without limitation pharmaceutical and cosmetic actives, drugs, medicaments, antigens or allergens such as ragweed pollen, spores, microorganisms including bacteria, seeds, mouthwash components such as chlorates or chlorites, flavors, fragrances, enzymes, preservatives, sweetening agents, colorants, spices, vitamins and combinations thereof.

The amount of active in the film depends on a number of factors, including, e.g., the chosen active, the desired treatment strength, the number of layers of the film, and the chosen formulation, as readily understood by one of ordinary skill in the art. The pharmaceutical active comprises from about 0.001% to about 99%, from about 0.003% to about 75%, or from about 0.005% to about 50% by weight of the film composition including, more than about 0.005%, more than about 0.05%, more than about 0.5%, more than about 1%, more than about 5%, more than about 10%, more than about 15%, more than about 20%, more than about 30%, about 50%, more than about 50%, less than about 50%, less than about 30%, less than about 20%, less than about 15%, less than about 10%, less than about 5%, less than about 1%, less than about 0.5%, less than about 0.05%, or less than about 0.005%. The amounts of other components may vary depending on the active and other components but typically these components comprise no more than about 50%, no more than about 30%, or no more than about 15% by total weight of the film composition.

Suitable actives for use in the films herein include, but are not limited to, the following therapeutic classes: ace-inhibitor; adrenergic agent; adrenocortical steroid; adrenocortical suppressant; aldosterone antagonist; alkaloid; amino acid; anabolic; analeptic; analgesic; anesthetic; anorectic; anti-acne agent; anti-adrenergic; anti-allergic; anti-amebic; anti-anemic; anti-anginal; anti-anxiety; anti-arthritic; anti-arrythmia; anti-asthmatic; anti-atherosclerotic; anticholesterolemic; antibacterial; antibiotic; anticholinergic; anticoagulant; anticonvulsant; antidepressant; antidiabetic; antidiarrheal; antidiuretic; antidote; anti-emetic; anti-epileptic; antifibrinolytic; antifungal; antihemorrhagic; antihistamine; antihyperlipidemia; antihypertensive; antihypotensive; anti-infective (both systemic and non-systemic); anti-inflammatory; anti-lipid; anti-manic; antimicrobial; antimigraine; antimitotic; antimycotic, antinauseant; antineoplastic; antineutropenic; anti-obesity; antiparasitic; anti-parkinson; antiproliferative; antipsychotic; anti-pyretic; antirheumatic; antiseborrheic; antisecretory; antispasmodic; anti-stroke; antithrombotic; anti-thyroid; anti-tumor; anti-tussive; anti-ulcerative; anti-uricemic; antiviral; appetite suppressant; appetite stimulant; biological response modifier; blood glucose regulator; blood modifier; blood metabolism regulator; bone resorption inhibitor; bronchodilator; cardiovascular agent; central nervous system stimulant; cerebral dilator; contraceptive; coronary dilator; cholinergic; cough suppressant; decongestant; depressant; diagnostic aid; dietary supplement; diuretic; dopaminergic agent; enzymes; estrogen receptor agonist; endometriosis management agent; expectorant; erectile dysfunction therapy; erythropoietic; ibrinolytic; fertility agent; fluorescent agent; free oxygen radical scavenger; gastric acid suppressant; gastrointestinal motility effector; genetic modifier; glucocorticoid; hair growth stimulant; hemostatic; histamine H2 receptor antagonists; homeopathic remedy; hormone; hypercalcemia management agent; hypocalcemia management agent; hypocholesterolemic; hypoglycemic; hypolipidemic; hypotensive; ion exchange resin; imaging agent; immunizing agent; immunomodulator; immunoregulator; immunostimulant; immunosuppressant; keratolytic; laxative; LHRH agonist; mood regulator; motion sickness preparation; mucolytic; muscle relaxant; mydriatic; nasal decongestant; neuromuscular blocking agent; neuroprotective; NMDA antagonist; non-hormonal sterol derivative; osteoporosis therapy; oxytocic; parasympatholytic; parasympathomimetic; plasminogen activator; platelet activating factor antagonist; platelet aggregation inhibitor; prostaglandin; psychotherapeutic; psychotropic; radioactive agent; respiratory agent; scabicide; sclerosing agent; sedative; sedative-hypnotic; selective adenosine A1 antagonist; serotonin antagonist; serotonin inhibitor; serotonin receptor antagonist; smoking cessation therapy; steroid; stimulant; sympatholytic; terine relaxant; thyroid hormone; thyroid inhibitor; thyromimetic; tranquilizer; tremor therapy; amyotrophic lateral sclerosis agent; cerebral ischemia agent; Paget's disease agent; unstable angina agent; vasoconstrictor; vasodilator; weight management; wound healing agent; xanthine oxidase inhibitor; and combinations thereof.

Examples of actives suitable for use herein include antacids, $H_2$-antagonists, and analgesics. For example, antacid dosages can be prepared using the ingredients calcium carbonate alone or in combination with magnesium hydroxide, and/or aluminum hydroxide. Moreover, antacids can be used in combination with $H_2$-antagonists.

Analgesics include opiates and opiate derivatives, such as oxycodone (commercially available as Oxycontin®); ibuprofen (commercially available as Motrin®, Advil®, Motrin Children's®, Motrin TB®, Advil Children's®, Motrin Infants'®, Motrin Junior®, Ibu-2®, Proprinal®, Ibu-200®, Midol Cramp Formula®, Bufen®, Motrin Migraine Pain®, Addaprin® and Haltran®), aspirin (commercially available as Empirin®, Ecotrin®, Genuine Bayer®, and Halfprin®), acetaminophen (commercially available as Silapap Infant's®, Silapap Children's®, Tylenol®, Tylenol Children's®, Tylenol Extra Strength®, Tylenol Infants' Original®, Tylenol Infants'®, Tylenol Arthritis®, T-Painol®, Q-Pap®, Cetafen®, Dolono®, Tycolene®, APAP® and Aminofen®), and combinations thereof that may optionally include caffeine. Other pain relieving agents may be used in the present invention, including meperidine hydrochloride (commercially available as Demerol®), capsaicin (commercially available as Qutenza®), morphine sulfate and naltrexone hydrochloride (commercially available as Embeda®), hydromorphone hydrochloride (commercially available as Dilaudid®), propoxyphene napsylate and acetaminophen (commercially available as Darvocet-N®), Fentanyl (commercially available as Duragesic®, Onsolis®, and Fentora®), sodium hyaluronate (commercially available as Euflexxa®), adalimumab (commercially available as Humira®), sumatriptan succinate (commercially available as Imitrex®), fentanyl iontophoretic (commercially available as Lonsys®), orphenadrine citrate (commercially available as Norgesic®), magnesium salicylate tetrahydrate (commercially available as Novasal®), oxymorphone hydrochloride (commercially available as Opana ER®), methocarbamol (commercially available as Robaxin®), carisoprodol (commercially available as Soma®), tramadol hydrochloride (commercially available as Ultracet® and Ultram®), morphine sulfate (commercially available as MS Contin®), metaxalone (commercially available as Skelaxin®), oxycodone hydrochloride (commercially available as OxyContin®), acetaminophen/oxycodone hydrochloride (commercially available as Percocet®), oxycodone/aspirin (commercially available as Percodan®), hydrocodone bitartrate/acetaminophen (commercially available as Vicodin®), hydrocodone bitartrate/ibuprofen (commercially available as Vicoprofen®), nepafenac (commercially available as Nevanac®), and pregabalin (commercially available as Lyrica®).

The films disclosed herein may further include agents such as NSAIDs, including etodolac (commercially available as Lodine®), ketorolac tromethamine (commercially available as Acular® or Acuvail®), naproxen sodium (commercially available as Anaprox®, Naprosyn®), flurbiprofen (commercially available as Ansaid®), diclofenac sodium/misoprostol (commercially available as Arthrotec®), celecoxib (commercially available as Celebrex®), sulindac (commercially available as Clinoril®), oxaprozin (commercially available as Daypro®), piroxicam (commercially available as Feldene®), indomethacin (commercially available as Indocin®), meloxicam (commercially available as Mobic®), mefenamic acid (commercially available as Ponstel®), tolmetin sodium (commercially available as Tolectin®), choline magnesium trisalicylate (commercially available as Trilisate®), diclofenac sodium (commercially available as Voltaren®), diclofenac potassium (commercially available as Cambia® or Zipsor®), and misoprostol (commercially available as Cytotec®). Opiate agonists and antagonists, such as buprenorphine and naloxone are further examples of drugs for use in the present invention.

Other drugs for other actives for use herein include anti-diarrheals such as loperamide (commercially available as Imodium AD®, Imotil®, Kaodene®, Imperim®, Diamode®, QC Anti-Diarrheal®, Health Care America Anti-Diarrheal®, Leader A-D®, and Imogen®), nitazoxanide (commercially available as Alinia®) and diphenoxylate hydrochloride/atropine sulfate (commercially available as Lomotil®), anti-histamines, anti-tussives, decongestants, vitamins, and breath fresheners. Common drugs used alone or in combination for colds, pain, fever, cough, congestion, runny nose and allergies, such as acetaminophen, ibuprofen, chlorpheniramine maleate, dextromethorphan, dextromethorphan HBr, phenylephrine HCl, pseudoephedrine HCl, diphenhydramine and combinations thereof, such as dextromethophan HBr and phenylephrine HCl (available as Triaminic®) may be included in the film compositions of the present invention.

Other actives useful herein include, but are not limited to, alcohol dependence treatment, such as acamprosate calcium (commercially available as Campral®); Allergy treatment medications, such as promethazine hydrochloride (commercially available as Phenergan®), bepotastine besilate (commercially available as Bepreve®), hydrocodone polistirex/chlorpheniramine polistirex (commercially available as Tussionex®), cetirizine hydrochloride (commercially available as Zyrtec®), cetirizine hydrochloride/pseudoephedrine hydrochloride (commercially available as Zyrtec-D®), promethazine hydrochloride/codeine phosphate (commercially available as Phenergan® with Codeine), pemirolast (commercially available as Alamast®), fexofenadine hydrochloride (commercially available as Allegra®), meclizine hydrochloride (commercially available as Antivert®), azelastine hydrochloride (commercially available as Astelin®), nizatidine (commercially available as Axid®), desloratadine (commercially available as Clarinex®), cromolyn sodium (commercially available as Crolom®), epinastine hydrochloride (commercially available as Elestat®), azelastine hydrochloride (commercially available as Optivar®), prednisolone sodium phosphate (commercially available as Orapred ODT®), olopatadine hydrochloride (commercially available as Patanol®), ketotifen fumarate (commercially available as Zaditor®), and montelukast sodium (commercially available as Singulair®); and anti-histamines such as diphenhydramine HCl (available as Benadryl®), loratadine (available as Claritin®), astemizole (available as Hismanal®), nabumetone (available as Relafen®), diphenydramine HCL (available as TheraFlu®) and clemastine (available as Tavist®).

Films of the present disclosure may further include Alzheimer's treatment medications, such as tacrine hydrochloride (commercially available as Cognex®), galantamine (commercially available as Razadyne®), donepezil hydrochloride (commercially available as Aricept®), rivastigmine tartrate (commercially available as Exelon®), caprylidene (commercially available as Axona®), and memantine (commercially available as Namenda®); anemia medication, such as cyanocobalamin (commercially available as Nascobal®) and ferumoxytol (commercially available as Feraheme®); anesthetics, such as antipyrine with benzocaine (commercially available as Auralgan®, Aurodex® and Auroto®); angina medication, such as amlodipine besylate (commercially available as Norvasc®), nitroglycerin (commercially available as Nitro-Bid®, Nitro-Dur®, Nitrolingual®, Nitrostat®, Transderm-Nitro®), isosorbide mononitrate (commercially available as Imdur®), and isosorbide dinitrate (commercially available as Isordil®); anti-tussives such as guaifensin; anti-Alzheimer's agents, such as nicergoline; and $Ca^H$-antagonists such as nifedipine (commercially available as Procardia® and Adalat®).

Actives useful in the present disclosure may also include anti-asthmatics, such as albuterol sulfate (commercially available as Proventil®), ipratropium bromide (commercially available as Atrovent®), salmeterol xinafoate (commercially available as Serevent®), zafirlukast (commercially available as Accolate®), flunisolide (commercially available as AeroBid®), metaproterenol sulfate (commercially available as Alupent®), albuterol inhalation (commercially available as Ventolin®), terbutaline sulfate (commercially available as Brethine®), formoterol (commercially available as Foradil®), cromolyn sodium (commercially available as Intal®), levalbuterol hydrochloride (commercially available as Xopenex®), zileuton (commercially available as Zyflo®), fluticasone propionate/salmeterol (commercially available as Advair®), albuterol sulfate/triamcinolone acetonide (commercially available as Azmacort®), dimethylxanthine (commercially available as Theophylline®), and beclomethasone (commercially available as Beclovent®, Beconase®, Qvar®, Vancenase®, Vanceril®); angioedema medication, such as C1 esterase Inhibitor (human) (commercially available as Berinert®) and ecallantide (commercially available as Kalbitor®); and anti-bacterial medications, such as trimethoprim/sulfamethoxazole (commercially available as Bactrim®), mupirocin (commercially available as Bactroban®), metronidazole (commercially available as Flagyl®), sulfisoxazole acetyl (commercially available as Gantrisin®), bismuth subsalicylate and metronidazole/tetracycline hydrochloride (commercially available as Helidac Therapy®), nitrofurantoin (commercially available as Macrodantin®), norfloxacin (commercially available as Noroxin®), erythromycin ethylsuccinate/Sulfisoxazole acetyl (commercially available as Pediazole®), and levofloxacin (commercially available as Levaquin®).

The films of the present disclosure may further include one or more antibiotics, including amoxicillin (commercially available as Amoxil®), ampicillin (commercially available as Omnipen®, Polycillin® and Principen®), amoxicillin/clavulanate potassium (commercially available as Augmentin®), moxifloxacin hydrochloride (commercially available as Avelox®), besifloxacin (commercially available as Besivance®), clarithromycin (commercially available as Biaxin®), ceftibuten (commercially available as Cedax®), cefuroxime axetil (commercially available as Ceftin®), cefprozil (commercially available as Cefzil®), ciprofloxacin hydrochloride (commercially available as Ciloxan® and Cipro®), clindamycin phosphate (commercially available as Cleocin T®), doxycycline hyclate (commercially available as Doryx®), dirithromycin (commercially available as Dynabac®), erythromycin (commercially available as E.E.S.®, E-Mycin®, Eryc®, Ery-Tab®, Erythrocin®, and PCE®), erythromycin topical (commercially available as A/T/S®, Erycette®, T-Stat®), gemifloxacin (commercially available as Factive®), ofloxacin (commercially known as Ocuflox®, Floxin®), telithromycin (commercially available as Ketek®), lomefloxacin hydrochloride (commercially available as Maxaquin®), minocycline hydrochloride (commercially available as Minocin®), fosfomycin tromethamine (commercially available as Monurol®), penicillin with potassium (commercially available as Penicillin VK®, Veetids®), trimethoprim (commercially available as Primsol®), ciprofloxacin hydrochloride (commercially available as Proquin XR®), rifampin, isoniazid and pyrazinamide (commercially available as Rifater®), cefditoren (commercially available as Spectracef®), cefixime (commercially available as Suprax®), tetracycline (commercially available as Achromycin V® and Sumycin®), tobramycin (commercially available as Tobrex®), rifaximin (commercially available as Xifaxan®), azithromycin (commercially available as Zithromax®), azithromycin suspension (commercially available as Zmax®), linezolid (commercially available as Zyvox®), benzoyl peroxide and clindamycin (commercially available as BenzaClin®), erythromycin and benzoyl peroxide (commercially available as Benzamycin®), dexamethasone (commercially available as Ozurdex®), ciprofloxacin and dexamethasone (commercially available as Ciprodex®), polymyxin B sulfate/neomycin sulfate/hydrocortisone (commercially available as Cortisporin®), colistin sulfate/neomycin sulfate/hydrocortisone acetate/thonzonium bromide (commercially available as Cortisporin-TC Otic®), cephalexin hydrochloride (commercially available as Keflex®), cefdinir (commercially available as Omnicef®), and gatifloxacin (commercially available as Zymar®).

Other useful actives include cancer treatment medications, including cyclophosphamide (commercially available as Cytoxan®), methotrexate (commercially available as Rheumatrex® and Trexal®), tamoxifen citrate (commercially available as Nolvadex®), bevacizumab (commercially available as Avastin®), everolimus (commercially available as Afinitor®), pazopanib (commercially available as Votrient®), and anastrozole (commercially available as Arimidex®); leukemia treatment, such as ofatumumab (commercially available as Arzerra®); anti-thrombotic drugs, such as antithrombin recombinant lyophilized powder (commercially available as Atryn®), prasugrel (commercially available as Efient®); anti-coagulants, such as aspirin with extended-release dipyridamole (commercially available as Aggrenox®), warfarin sodium (commercially available as Coumadin®), dipyridamole (commercially available as Persantine®), dalteparin (commercially available as Fragmin®), danaparoid (commercially available as Orgaran®), enoxaparin (commercially available as Lovenox®), heparin (commercially available as Hep-Lock, Hep-Pak, Hep-Pak CVC, Heparin Lock Flush), tinzaparin (commercially available as Innohep®), and clopidogrel bisulfate (commercially available as Plavix®); antiemetics, such as granisetron hydrochloride (commercially available as Kytril®) and nabilone (commercially available as Cesamet®), trimethobenzamide hydrochloride (commercially available as Tigan®), and ondansetron hydrochloride (commercially available as Zofran®); anti-fungal treatment, such as ketoconazole (commercially available as Nizoral®), posaconazole (commercially available as Noxafil®), ciclopirox (commercially available as Penlac®), griseofulvin (commercially available as Gris-PEG®), oxiconazole nitrate (commercially available as Oxistat®), fluconazole (commercially available as Diflucan®), sertaconazole nitrate (commercially available as Ertaczo®), terbinafine hydrochloride (commercially available as Lamisil®), ciclopirox (commercially available as Loprox®), nystatin/triamcinolone acetonide (commercially available as Mycolog-II®), econazole nitrate (commercially available as Spectazole®), itraconazole (commercially available as Sporanox®), and terconazole (commercially available as Terazol®).

Actives may further include anti-inflammatory medications, such as hydroxychloroquine sulfate (commercially available as Plaquenil®), fluticasone propionate (commercially available as Cutivate®), canakinumab (commercially available as Llaris®), amcinonide (commercially available as Cyclocort®), methylprednisolone (commercially available as Medrol®), budesonide (commercially available as Entocort EC®), anakinra (commercially available as Kineret®), diflorasone diacetate (commercially available as Psorcon®), and etanercept (commercially available as Enbrel®); antispasmodic medication, such as phenobarbital/hyoscyamine sulfate/atropine sulfate/scopolamine hydrobromide (commercially available as Donnatal®); antiviral treatment, such as oseltamivir phosphate (commercially available as Tamiflu®); anti-parasites medication, including tinidazole (commercially available as Tindamax®); appetite treatment mediations, such as megestrol acetate (commercially available as Megace ES®), phentermine hydrochloride (commercially available as Adipex-P®), and diethylpropion hydrochloride (commercially available as Tenuate®); arthritis medications, including leflunomide (commercially available as Arava®), certolizumab pegol (commercially available as Cimzia®), diclofenac sodium (commercially available as Pennsaid®), golimumab (commercially available as Simponi®), and tocilizumab (commercially available as Actemra®); bladder control medication, such as trospium chloride (commercially available as Sanctura®), desmopressin acetate (commercially available as DDAVP®), tolterodine tartrate (commercially available as Detrol®), oxybutynin chloride (commercially available as Ditropan® or Gelnique®), darifenacin (commercially available as Enablex®), and solifenacin succinate (commercially available as VESlcare®); blood vessel constrictors, such as methylergonovine maleate (commercially available as Methergine®); plasma uric managers, such as rasburicase (commercially available as Elitek®); iron deficiency anemia medications, such as ferumoxytol (commercially available as Feraheme®); lymphoma medications, such as pralatrexate (commercially available as Folotyn®), romidepsin (commercially available as Isodax®); malaria medication, such as artemether/lumefantrine (commercially available as Coartem®); hyponatremia medication, such as tolvatpan (commercially available as Samsca®); medication for treatment of von Willebrand disease (commercially available as Wilate®); anti-hypertension medications, such as treprostinil (commercially available as Tyvaso®), tadalafil (commercially available as Adcirca®); cholesterol lowering medication, including paricalcitol (commercially available as Altocor®), pitavastatin (commercially available as Livalo®), lovastatin, niacin (commercially available as Advicor®), colestipol hydrochloride (commercially available as Colestid®), rosuvastatin calcium (commercially available as Crestor®), fluvastatin sodium (commercially available as Lescol®), atorvastatin calcium (commercially available as Lipitor®), lovastatin (commercially available as Mevacor®), niacin (commercially available as Niaspan®), pravastatin sodium (commercially available as Pravachol®), pavastatin sodium with buffered aspirin (commercially available as Pravigard PAC®), cholestyramine (commercially available as Questran®), simvastatin and niacin (commercially available as Simcor®), atenolol, chlorthalidone (commercially available as Tenoretic®), atenolol (commercially available as Tenormin®), fenofibrate (commercially available as Tricor®), fenofibrate (commercially available as Triglide®), ezetimibe/simvastatin (commercially available as Vytorin®), colesevelam (commercially available as WelChol®), bisoprolol fumarate (commercially available as Zebeta®), ezetimibe (commercially available as Zetia®), bisoprolol fumarate/hydrochlorothiazide (commercially available as Ziac®), and simvastatin (commercially available as Zocor®).

The actives included herein may also include chronic kidney disease medication, such as paricalcitol (commercially available as Zemplar®); contraceptive agents, including etonogestrel (commercially available as Implanon®), norethindrone acetate, ethinyl estradiol (commercially available as Loestrin 24 FE®), ethinyl estradiol, norelgestromin (commercially available as Ortho Evra®), levonorgestrel (commercially available as Plan B®), levonorgestrel and ethinyl estradiol (commercially available as Preven®), levonorgestrel, ethinyl estradiol (commercially available as Seasonique®), and medroxyprogesterone acetate (commercially available as Depo-Provera®); COPD medication, such as arformoterol tartrate (commercially available as Brovana®) and ipratropium bromide, albuterol sulfate (commercially available as Combivent®); cough suppressants, including benzonatate (commercially available as Tessalon®), guaifenesin, codeine phosphate (commercially available as Tussi-Organidin NRC)), and acetaminophen, codeine phosphate (commercially available as Tylenol with Codeine®); medication for the treatment of diabetes, including pioglitazone hydrochloride, metformin hydrochloride (commercially available as ACTOplus Met®), bromocriptine mesylate (commercially available as Cycloset®), liraglutide (commercially available as Victoza®), saxagliptin (commercially available as Onglyza®), pioglitazone hydrochloride (commercially available as Actos®), glimepiride (commercially available as Amaryl®), rosiglitazone maleate, metformin hydrochloride (commercially available as Avandamet®), rosiglitazone maleate (commercially available as Avandaryl®), rosiglitazone maleate (commercially available as Avandia®), exenatide (commercially available as Byetta®), exenatide (commercially available as Bydureon®), chlorpropamide (commercially available as Diabinese®), pioglitazone hydrochloride, glimepiride (commercially available as Duetact®), metformin hydrochloride (commercially available as Glucophage®), glipizide (commercially available as Glucotrol®), glyburide, metformin (commercially available as Glucovance® and Fortamet®), metformin hydrochloride (commercially available as Glumetza®), sitagliptin (commercially available as Januvia®), detemir (commercially available as Levemir®), glipizide, metformin hydrochloride (commercially available as Metaglip®), glyburide (commercially available as Micronase®), repaglinide (commercially available as Prandin®), acarbose (commercially available as Precose®), nateglinide (commercially available as Starlix®), pramlintide acetate (commercially available as Symlin®), canagliflozin (commercially available as Invokana®), linagliptin (commercially available as Tradjenta®), dapagliflozin (commercially available as Farxiga®), insulin glargine (commercially available as Lantus® or Toujeo®), insulin aspart (commercially available as Novolog®), insulin lispro, empagliflozin (commercially available as Jardiance®), and tolazamide (commercially available as Tolinase®).

Other useful actives may include digestive agents, such as sulfasalazine (commercially available as Azulfidine®), rabeprazole sodium (commercially available as AcipHex®), lubiprostone (commercially available as Amitiza®), dicyclomine hydrochloride (commercially available as Bentyl®), sucralfate (commercially available as Carafate®), lactulose (commercially available as Chronulac®), docusate (commercially available as Colace®), balsalazide disodium (commercially available as Colazal®), losartan potassium (commercially available as Cozaar®), olsalazine sodium (commercially available as Dipentum®), chlordiazepoxide hydrochloride, clidinium bromide (commercially available as Librax®), esomeprazole magnesium (commercially available as Nexium®), famotidine (commercially available as Pepcid®), lansoprazole (commercially available as Prevacid®), lansoprazole and naproxen (commercially available as Prevacid NapraPAC®), amoxicillin/clarithromycin/lansoprazole (commercially available as Prevpac®), omeprazole (commercially available as Prilosec®), pantoprazole sodium (commercially available as Protonix®), metoclopramide hydrochloride (commercially available as Reglan® or Metozolv®), cimetidine (commercially available as Tagamet®), ranitidine hydrochloride (commercially available as Zantac®), and omeprazole, sodium bicarbonate (commercially available as Zegerid®); diuretics, including spironolactone, hydrochlorothiazide (commercially available as Aldactazide®), spironolactone (commercially available as Aldactone®), bumetanide (commercially available as Bumex®), torsemide (commercially available as Demadex®), chlorothiazide (commercially available as Diuril®), furosemide (commercially available as Lasix®), metolazone (commercially available as Zaroxolyn®), and hydrochlorothiazide, triamterene (commercially available as Dyazide®).

Actives useful herein may also include treatment for emphysema, such as tiotropium bromide (commercially available as Spiriva®); fibromyalgia medication, such as milnacipran hydrochloride (commercially available as Savella®); medication for the treatment of gout, such as colchicine (commercially available as Colcrys®), and febuxostat (commercially available as Uloric®); enema treatments, including aminosalicylic acid (commercially available as Mesalamine® and Rowasa®); epilepsy medications, including valproic acid (commercially available as Depakene®), felbamate (commercially available as Felbatol®), lamotrigine (commercially available as Lamictal®), primidone (commercially available as Mysoline®), oxcarbazepine (commercially available as Trileptal®), zonisamide (commercially available as Zonegran®), levetiracetam (commercially available as Keppra®), and phenytoin sodium (commercially available as Dilantin®).

Actives useful herein may further include eye medications and treatment, such as dipivefrin hydrochloride (commercially available as Propine®), valganciclovir (commercially available as Valcyte®), ganciclovir ophthalmic gel (commercially available as Zirgan®); bepotastine besilate (commercially available as Bepreve®), besifloxacin (commercially available as Besivance®), bromfenac (commercially available as Xibrom®), fluorometholone (commercially available as FML®), pilocarpine hydrochloride (commercially available as Pilocar®), cyclosporine (commercially available as Restasis®), brimonidine tartrate (commercially available as Alphagan P®), dorzolamide hydrochloride/timolol maleate (commercially available as Cosopt®), bimatoprost (commercially available as Lumigan®), timolol maleate (available as Timoptic®), travoprost (commercially available as Travatan®), latanoprost (commercially available as Xalatan®), echothiophate iodide (commercially available as Phospholine Iodide®), and ranibizumab (commercially available as Lucentis®); fluid controllers, such as acetazolamide (commercially available as Diamox®); gallstone medications, including ursodiol (commercially available as Actigall®); medication for the treatment of gingivitis, including chlorhexidine gluconate (commercially available as Peridex®); headache medications, including butalbital/codeine phosphate/aspirin/caffeine (commercially available as Fiornal® with Codeine), naratriptan hydrochloride (commercially available as Amerge®), almotriptan (commercially available as Axert®), ergotamine tartrate/caffeine (commercially available as Cafergot®), butalbital/acetaminophen/caffeine (commercially available as Fioricet®), butalbital/aspirin/caffeine (commercially available as Fiorinal®), frovatriptan succinate (commercially available as Frova®), rizatriptan benzoate (commercially available as Maxalt®), isometheptene mucate/dichloralphenazone/acetaminophen (commercially available as Midrin®), dihydroergotamine mesylate (commercially available as Migranal®), eletriptan hydrobromide (commercially available as Relpax®), and zolmitriptan (commercially available as Zomig®); influenza medication, such as *haemophilus* b conjugate vaccine; tetanus toxoid conjugate (commercially available as Hiberix®); and heart treatments, including quinidine sulfate, isosorbide dinitrate/hydralazine hydrochloride (commercially available as BiDil®), digoxin (commercially available as Lanoxin®), flecainide acetate (commercially available as Tambocor®), mexiletine hydrochloride (commercially available as Mexitil®), disopyramide phosphate (commercially available as Norpace®), procainamide hydrochloride (commercially available as Procanbid®), and propafenone (commercially available as Rythmol®).

Other useful actives include hepatitis treatments, including entecavir (commercially available as Baraclude®), hepatitis B immune globulin (commercially available as HepaGam B®), and copegus/rebetol/ribasphere/vilona/virazole (commercially available as Ribavirin®); herpes treatments, including valacyclovir hydrochloride (commercially available as Valtrex®), penciclovir (commercially available as Denavir®), acyclovir (commercially available as Zovirax®), and famciclovir (commercially available as Famvir®); treatment for high blood pressure, including enalaprilat (available as Vasotec®), captopril (available as Capoten®) and lisinopril (available as Zestril®), verapamil hydrochloride (available as Calan®), ramipril (commercially available as Altace®), olmesartan medoxomil (commercially available as Benicar®), amlodipine/atorvastatin (commercially available as Caduet®), nicardipine hydrochloride (commercially available as Cardene®), diltiazem hydrochloride (commercially available as Cardizem®), quinapril hydrochloride (commercially available as Accupril®), quinapril hydrochloride/hydrochlorothiazide (commercially available as Accuretic®), perindopril erbumine (commercially available as Aceon®), candesartan cilexetil (commercially available as Atacand®), candesartan cilexetil/hydrochlorothiazide (commercially available as Atacand HCT®), irbesartan/hydrochlorothiazide (commercially available as Avalide®), irbesartan (commercially available as Avapro®), amlodipine besylate/olmesartan medoxomil (commercially available as Azor®), levobunolol hydrochloride (commercially available as Betagan®), betaxolol hydrochloride (commercially available as Betoptic®), nebivolol (commercially available as Bystolic®), captopril/hydrochlorothiazide (commercially available as Capozide®), doxazosin mesylate (commercially available as Cardura®), clonidine hydrochloride (commercially available as Catapres®), carvedilol (commercially available as Coreg®), nadolol (commercially available as Corgard®), nadolol/bendroflumethiazide (commercially available as Corzide®), valsartan (commercially available as Diovan®), isradipine (commercially available as DynaCirc®), Guanabenz acetate. (commercially available as Wytensin®), Guanfacine hydrochloride (commercially available as Tenex® or Intuniv®), losartan potassium/hydrochlorothiazide (commercially available as Hyzaar®), propranolol hydrochloride (commercially available as Indera®), propranolol hydrochloride/hydrochlorothiazide (commercially available as Inderide®), eplerenone (commercially available as Inspra®), ambrisentan (commercially available as Letairis®), enalapril maleate/felodipine (commercially available as Lexxel®), metoprolol tartrate (commercially available as Lopressor®), benazepril hydrochloride (commercially available as Lotensin®), benazepril hydrochloride/hydrochlorothiazide (commercially available as Lotensin HCT®), amlodipine/benazepril hydrochloride (commercially available as Lotrel®), indapamide (commercially available as Lozol®), trandolapril (commercially available as Mavik®), telmisartan (commercially available as Micardis®), telmisartan/hydrochlorothiazide (commercially available as Micardis HCT®), prazosin hydrochloride (commercially available as Minipress®), amiloride, hydrochlorothiazide (commercially available as Moduretic®), fosinopril sodium (commercially available as ZZXT Monopril®), fosinopril sodium/hydrochlorothiazide (commercially available as Monopril-HCT®), pindolol (commercially available as Visken®), felodipine (commercially available as Plendil®), sildenafil citrate (commercially available as Revatio®), Nisoldipine (commercially available as Sular®), trandolapril/verapamil hydrochloride (commercially available as Tarka®), aliskiren (commercially available as Tekturna®), eprosartan mesylate (commercially available as Teveten®), eprosartan mesylate/hydrochlorothiazide (commercially available as Teveten HCT®), moexipril hydrochloride/hydrochlorothiazide (commercially available as Uniretic®), moexipril hydrochloride (commercially available as Univasc®), enalapril maleate/hydrochlorothiazide (commercially available as Vaseretic®), and lisinopril/hydrochlorothiazide (commercially available as Zestoretic®).

The films of the present disclosure may include actives useful in the medication for the treatment of HIV/AIDS, such as amprenavir (commercially available as Agenerase®), tipranavir (commercially available as Aptivus®), efavirenz/emtricitabine/tenofovir (commercially available as Atripla®), lamivudine/zidovudine (commercially available as Combivir®), indinavir sulfate (commercially available as Crixivan®), lamivudine (commercially available as Epivir®), saquinavir (commercially available as Fortovase®), zalcitabine (commercially available as Hivid®), lopinavir/ritonavir (commercially available as Kaletra®), fosamprenavir calcium (commercially available as Lexiva®), ritonavir (commercially available as Norvir®), zidovudine (commercially available as Retrovir®), atazanavir sulfate (commercially available as Reyataz®), efavirenz (commercially available as Sustiva®), abacavir/lamivudine/zidovudine (commercially available as Trizivir®), didanosine (commercially available as Videx®), nelfinavir mesylate (commercially available as Viracept®), nevirapine (commercially available as Viramune®), tenofovir disoproxil fumarate (commercially available as Viread®), stavudine (commercially available as Zerit®), and abacavir sulfate (commercially available as Ziagen®); homocysteiene removers, including betaine anhydrous (commercially available as Cystadane®); medications, such as insulin (commercially available as Apidra®, Humalog®, Humulin®, Iletin®, Tresiba®, and Novolin®); and HPV treatment, such as Human papillomavirus vaccine (commercially available as Gardasil®) or human papillomavirus bivalent (commercially available as Cervarix®); immunosuppressants, including cyclosporine (commercially available as Gengraf®, Neoral®, Sandimmune®, and Apo-Cyclosporine®).

Actives useful in the present disclosure may further include prolactin inhibitors, such as bromocriptine mesylate (commercially available as Parlodel®); medications for aiding in stress tests, such as regadenoson (commercially available as Lexiscan®); baldness medication, including finasteride (commercially available as Propecia® and Proscar®); pancreatitis treatment, such as gemfibrozil (commercially available as Lopid®); hormone medications, such as norethindrone acetate/ethinyl estradiol (commercially available as femHRT®), goserelin acetate (commercially available as Zoladex®), progesterone gel (commercially available as Prochieve®), progesterone (commercially available as Prometrium®), calcitonin-salmon (commercially available as Miacalcin®), calcitriol (commercially available as Rocaltrol®), synthroid (commercially available as Levothroid®, Levoxyl®, Unithroid®), testosterone (commercially available as Testopel®, Androderm®, Testoderm®, and AndroGel®); menopause medication, such as estradiol/norethindrone acetate (commercially available as Activella®), drospirenone/estradiol (commercially available as Angeliq®), estradiol/levonorgestrel (commercially available as Climara Pro®), estradiol/norethindrone acetate (commercially available as CombiPatch®), estradiol (commercially available as Estrasorb®, Vagifem® and Estro-Gel®), esterified estrogens and methyltestosterone (commercially available as Estratest®), estrogen (commercially available as Alora®, Climara®, Esclim®, Estraderm®, Vivelle®, Vivelle-Dot®), estropipate (commercially available as Ogen®), conjugated estrogens (commercially available as Premarin®), and medroxyprogesterone acetate (commercially available as Provera®); menstrual medications, including leuprolide acetate (commercially available as Lupron Depot), tranexamic acid (commercially available as Lysteda®), and norethindrone acetate (commercially available as Aygestin®); and muscle relaxants, including cyclobenzaprine hydrochloride (commercially available as Flexeril®), tizanidine (commercially available as Zanaflex®), and hyoscyamine sulfate (commercially available as Levsin®).

Actives useful herein may also include osteoporosis medications, including ibrandronate sodium (commercially available as Boniva®), risedronate (commercially available as Actonel®), raloxifene hydrochloride (commercially available as Evista®, Fortical®), and alendronate sodium (commercially available as Fosamax®); ovulation enhancers, including clomiphene citrate (commercially available as Serophene®, Clomid®, Serophene®); Paget's disease treatment, such as etidronate disodium (commercially available as Didronel®); pancreatic enzyme deficiency medications, such as pancrelipase (commercially available as Pancrease® or Zenpep®); medication for the treatment of Parkinson's disease, such as pramipexole dihydrochloride (commercially available as Mirapex®), ropinirole hydrochloride (commercially available as Requip®), carbidopa/levodopa (commercially available as Sinemet CR®), carbidopa/levodopa/entacapone (commercially available as Stalevo®), selegiline hydrochloride (commercially available as Zelapar®), rasagiline (commercially available as Azilect®), entacapone (commercially available as Comtan®), and selegiline hydrochloride (commercially available as Eldepryl®); multiple sclerosis medication, such as dalfampridine (commercially available as Ampyra®) and interferon beta-I b (commercially available as Extavia®); prostate medication, including flutamide (commercially available as Eulexin®), nilutamide (commercially available as Nilandron®), dutasteride (commercially available as Avodart®), tamsulosin hydrochloride (commercially available as Flomax®), terazosin hydrochloride (commercially available as Hytrin®), and alfuzosin hydrochloride (commercially available as UroXatral®).

Films of the present disclosure may further include psychiatric medications, including alprazolam (available as Niravam®, Xanax®), clozopin (available as Clozaril®), haloperidol (available as Haldol®), fluoxetine hydrochloride (available as Prozac®), sertraline hydrochloride (available as Zoloft®), asenapine (commercially available as Saphris®), iloperidone (commercially available as Fanapt®), paroxtine hydrochloride (available as Paxil®), aripiprazole (commercially available as Abilify®), guanfacine (commercially available as Intuniv®), Amphetamines and methamphetamines (commercially available as Adderall® and Desoxyn®), clomipramine hydrochloride (commercially available as Anafranil®), Buspirone hydrochloride (commercially available as BuSpar®), citalopram hydrobromide (commercially available as Celexa®), duloxetine hydrochloride (commercially available as Cymbalta®), methylphenidate (commercially available as Ritalin, Daytrana®), divalproex sodium (Valproic acid) (commercially available as Depakote®), dextroamphetamine sulfate (commercially available as Dexedrine®), venlafaxine hydrochloride (commercially available as Effexor®), selegiline (commercially available as Emsam®), carbamazepine (commercially available as Equetro®), lithium carbonate (commercially available as Eskalith®), fluvoxamine maleate/dexmethylphenidate hydrochloride (commercially available as Focalin®), ziprasidone hydrochloride (commercially available as Geodon®), ergoloid mesylates (commercially available as Hydergine®), escitalopram oxalate (commercially available as Lexapro®), chlordiazepoxide (commercially available as Librium®), molindone hydrochloride (commercially available as Moban®), phenelzine sulfate (commercially available as Nardil®), thiothixene (commercially available as Navane®), desipramine hydrochloride (commercially available as Norpramin®), benzodiazepines (such as those available as Oxazepam®), nortriptyline hydrochloride (commercially available as Pamelor®), tranylcypromine sulfate (commercially available as Parnate®), prochlorperazine, mirtazapine (commercially available as Remeron®), risperidone (commercially available as Risperdal®), quetiapine fumarate (commercially available as Seroquel®), doxepin hydrochloride (commercially available as Sinequan®), atomoxetine hydrochloride (commercially available as Strattera®), trimipramine maleate (commercially available as Surmontil®), olanzapine/fluoxetine hydrochloride (commercially available as Symbyax®), imipramine hydrochloride (commercially available as Tofranil®), protriptyline hydrochloride (commercially available as Vivactil®), bupropion hydrochloride (commercially available as Wellbutrin®, Wellbutrin SR®, and Wellbutrin XR®), and olanzapine (commercially available as Zyprexa®).

Actives useful herein may also include uric acid reduction treatment, including allopurinol (commercially available as Zyloprim®); seizure medications, including gabapentin (commercially available as Neurontin®), ethotoin (commercially available as Peganone®), vigabatrin (commercially available as Sabril®), and topiramate (commercially available as Topamax®); treatment for shingles, such as zoster vaccine live (commercially available as Zostavax®); skin care medications, including calcipotriene (commercially available as Dovonex®), ustekinumab (commercially available as Stelara®), televancin (commercially available as Vibativ®), isotretinoin (commercially available as Accutane®), hydrocortisone/iodoquinol (commercially available as Alcortin®), sulfacetamide sodium/sulfur (commercially available as Avar®), azelaic acid (commercially available as Azelex®, Finacea®), benzoyl peroxide (commercially available as Desquam-E®), adapalene (commercially available as Differin®), fluorouracil (commercially available as Efudex®), pimecrolimus (commercially available as Elidel®), topical erythromycin (commercially available as A/T/S®, Erycette®, T-Stat®), hydrocortisone (commercially available as Cetacort®, Hytone®, Nutracort®), metronidazole (commercially available as MetroGel®), doxycycline (commercially available as Oracea®), tretinoin (commercially available as Retin-A® and Renova®), mequinol/tretinoin (commercially available as Solage®), acitretin (commercially available as Soriatane®), calcipotriene hydrate/betamethasone dipropionate (commercially available as Taclonex®), tazarotene (commercially available as Tazorac®), fluocinonide (commercially available as Vanos®), desonide (commercially available as Verdeso®), miconazole nitrate/Zinc oxide (commercially available as Vusion®), ketoconazole (commercially available as Xolegel®), and efalizumab (commercially available as Raptiva®).

Other actives useful herein may include Sleep disorder medications, including zaleplon (available as Sonata®), eszopiclone (available as Lunesta®), zolpidem tartrate (commercially available as Ambien®, Ambien CR®, Edluar®), lorazepam (commercially available as Ativan®), flurazepam hydrochloride (commercially available as Dalmane®), triazolam (commercially available as Halcion®), clonazepam (commercially available as Klonopin®), barbituates, such as Phenobarbital®), Modafinil (commercially available as Provigil®), temazepam (commercially available as Restoril®), ramelteon (commercially available as Rozerem®), clorazepate dipotassium (commercially available as Tranxene®), diazepam (commercially available as Valium®), quazepam (commercially available as Doral®), and estazolam (commercially available as ProSom®); smoking cessation medications, such as varenicline (commercially available as Chantix®), nicotine, such as Nicotrol®, and bupropion hydrochloride (commercially available as Zyban®); and steroids, including alclometasone dipropionate (commercially available as Aclovate®), betamethasone dipropionate (commercially available as Diprolene®), mometasone furoate (commercially available as Elocon®), fluticasone (commercially available as Flonase®, Flovent®, Flovent Diskus®, Flovent Rotadisk®), fluocinonide (commercially available as Lidex®), mometasone furoate monohydrate (commercially available as Nasonex®), desoximetasone (commercially available as Topicort®), clotrimazole/betamethasone dipropionate (commercially available as Lotrisone®), prednisolone acetate (commercially available as Pred Forte®, Prednisone®, Budesonide Pulmicort®, Rhinocort Aqua®), prednisolone sodium phosphate (commercially available as Pediapred®), desonide (commercially available as Tridesilon®), and halobetasol propionate (commercially available as Ultravate®).

Films of the present invention may further include actives useful for thyroid disease treatment, such as hormones TC and TD (commercially available as Armour Thyroid®); potassium deficiency treatment, including potassium chloride (commercially available as Micro-KC)); triglycerides regulators, including omega-3-acid ethyl esters (commercially available as Omacor®); urinary medication, such as phenazopyridine hydrochloride (commercially available as Pyridium®) and methenamine, methylene blue/phenyl salicylate/benzoic acid/atropine sulfate/hyoscyamine (commercially available as Urised®); prenatal vitamins (commercially available as Advanced Natalcare®, Materna®, Natalins®, Prenate Advance®); weight control medication, including orlistat (commercially available as Xenical®) and sibutramine hydrochloride (commercially available as Meridia®).

The popular $H_2$-antagonists which are contemplated for use herein include cimetidine, ranitidine hydrochloride, famotidine, nizatidien, ebrotidine, mifentidine, roxatidine, pisatidine and aceroxatidine.

Active antacid ingredients include, but are not limited to, the following: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, bismuth subsilysilate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium trisilicate, milk solids, aluminum mono-ordibasic calcium phosphate, tricalcium phosphate, potassium bicarbonate, sodium tartrate, sodium bicarbonate, magnesium aluminosilicates, tartaric acids and salts.

The active agents employed in the present invention may include allergens or antigens, such as, but not limited to, plant pollens from grasses, trees, or ragweed; animal danders, which are tiny scales shed from the skin and hair of cats and other furred animals; insects, such as house dust mites, bees, and wasps; and drugs, such as penicillin.

Examples of specific actives include but are not limited to 16-alpha fluorocstradiol, 16-alpha-gitoxin, 16-epiestriol, 17 alpha dihydroequilenin, 17 alpha estradiol, 17 beta estradiol, 17 hydroxy progesterone, lalpha-hydroxyvitamin D2,1-dodecpyrrolidinone, 20-epi-1,25 dihydroxyvitamin D3, 22-oxacalcitriol, 2CVV, 2'-nor-cGMP, 3-isobutyl GABA, 5-ethynyluracil, 6-FUDCA, 7-methoxytacrine, Abamectin, abanoquil, abecarnil, abiraterone, Ablukast, Ablukast Sodium, Acadesine, acamprosate, Acarbose, Acebutolol, Acecainide Hydrochloride, Aceclidine, aceclofenae, Acedapsone, Aceglutamide Aluminum, Acemannan, Acetaminophen, Acetazolamide, Acetohexamide, Acetohydroxamic Acid, acetomepregenol, Acetophenazine Maleate, Acetosulfone Sodium, Acetylcholine Chloride, Acetylcysteine, acetyl-L-carnitine, acetylmethadol, Acifran, acipimox, acitemate, Acitretin, Acivicin, Aclarubicin, aclatonium, Acodazole Hydrochloride, aconiazide, Acrisorcin, Acrivastine, Acronine, Actisomide, Actodigin, Acyclovir, acylfulvene, adafenoxate, adapalene, Adapalene, adatanserin, Adatanserin Hydrochloride, adecypenol, adecypenol, Adefovir, adelmidrol, ademetionine, Adenosine, Adinazolam, Adipheinine Hydrochloride, adiposin, Adozelesin, adrafinil, Adrenalone, airbutamine, alacepril, Alamecin, Alanine, Alaproclate, alaptide, Albendazole, albolabrin, Albuterol, Albutoin, Alclofenae, Alclometasone Dipropionate, Alcloxa, aldecalmycin, Aldesleukin, Aldioxa, Alendronate Sodium, alendronic acid, alentemol, Alentemol Hydrobromide, Aletamine Hydrochloride, Aleuronium Chloride, Alexidine, alfacalcidol, Alfentanil Hydrochloride, alfuzosin, Algestone Acetonide, alglucerase, Aliflurane, alinastine, Alipamide, Allantoin, Allobarbital, Allopurinol, ALL-TK antagonists, Alogliptin, Alonimid, alosetron, Alosetron Hydrochloride, Alovudine, Alpertine, Alpha Amylase, alpha idosone, Alpidem, Alprazolam, Alprenolol Hydrochloride, Alprenoxime Hydrochloride, Alprostadil, Alrestatin Sodium, Altanserin Tartrate, Alteplase, Althiazide, Altretamine, altromycin B, Alverine Citrate, Alvircept Sudotox, Amadinone Acetate, Amantadine Hydrochloride, ambamustine, Ambomycin, Ambruticin, Ambuphylline, Ambuside, Amcinafal, Amcinonide, Amdinocillin, Amdinocillin Pivoxil, Amedalin Hydrochloride, amelometasone, Ameltolide, Amesergide, Ametantrone Acetate, amezinium metilsulfate, amfebutamone, Amfenac Sodium, Amflutizole, Amicycline, Amidephrine Mesylate, amidox, Amifloxacin, amifostine, Amikacin, Amiloride Hydrochloride, Aminacrine Hydrochloride, Aminobenzoate Potassium, Aminobenzoate Sodium, Aminocaproic Acid, Aminoglutethimide, Aminohippurate Sodium, aminolevulinic acid, Aminophylline, A minorex, Aminosalicylate sodium, Aminosalicylic acid, Amiodarone, Amiprilose Hydrochloride, Amiquinsin Hydrochloride, amisulpride, Amitraz, Amitriptyline Hydrochloride, Amlexanox, amlodipine, Amobarbital Sodium, Amodiaquine, Amodiaquine Hydrochloride, Amorolfine, Amoxapine, Amoxicillin, Amphecloral, Amphetamine Sulfate, Amphomycin, Amphotericin B, Ampicillin, ampiroxicam, Ampyzine Sulfate, Amquinate, Amrinone, amrinone, amrubicin, Amsacrine, amylin, amythiamicin, Anagestone Acetate, anagrelide, Anakinra, ananain, anaritide, Anaritide Acetate, Anastrozole, Anazolene Sodium, Ancrod, andrographolide, Androstenedione, angiogenesis inhibitors, Angiotensin Amide, Anidoxime, Anileridine, Anilopam Hydrochloride, Aniracetam, Anirolac, Anisotropine Methylbromide, Anistreplase, Anitrazafen, anordrin, antagonist D, antagonist G, antarelix, Antazoline Phosphate, Anthelmycin, Anthralin, Anthramycin, antiandrogen, Acedapsone, Felbamate, antiestrogen, antineoplaston, Antipyrine, antisense oligonucleotides, apadoline, apafant, Apalcillin Sodium, apaxifylline, Apazone, aphidicolin glycinate, Apixifylline, Apomorphine Hydrochloride, apraclonidine, Apraclonidine Hydrochloride, Apramycin, Aprindine, Aprindine Hydrochloride, aprosulate sodium, Aprotinin, Aptazapine Maleate, aptiganel, apurinic acid, apurinic acid, aranidipine, Aranotin, Arbaprostil, arbekicin, arbidol, Arbutamine Hydrochloride, Arclofenin, Ardeparin Sodium, argatroban, Arginine, Argipressin Tannate, Arildone, aripiprazol, arotinolol, Arpinocid, Arteflene, Artilide Fumarate, asimadoline, aspalatone, Asparaginase, Asparic Acid, Aspartocin, asperfuran, Aspirin, aspoxicillin, Asprelin, Astemizole, Astromicin Sulfate, asulacrine, atamestane, Atenolol, atevirdine, Atipamezole, Atiprosin Maleate, Atolide, Atorvastatin Calcium, Atosiban, Atovaquone, atpenin B, Atracurium Besylate, atrimustine, atrinositol, Atropine, Auranofin, aureobasidin A, Aurothioglucose, Avilamycin, Avoparcin, Avridine, Axid, axinastatin 1, axinastatin 2, axinastatin 3, Azabon, Azacitidinie, Azaclorzine Hydrochloride, Azaconazole, azadirachtine, Azalanstat Dihydrochloride, Azaloxan Fumarate, Azanator Maleate, Azanidazole, Azaperone, Azaribine, Azaserine, azasetron, Azatadine Maleate, Azathioprine, Azathioprine Sodium, azatoxin, azatyrosine, azelaic acid, azelastine, azelnidipine, Azepindole, Azetepa, azimilide, Azithromycin, Azlocillin, Azolimine, Azosemide, Azotomycin, Aztreonam, Azumolene Sodium, Bacampicillin Hydrochloride, baccatin III, Bacitracin, Baclofen, bacoside A, bacoside B, bactobolamine, balanol, balazipone, balhimycin, balofloxacin, balsalazide, Bambermycins, bambuterol, Bamethan Sulfate, Bamifylline Hydrochloride, Bamidazole, baohuoside 1, Barmastine, barnidipine, Basifungin, Batanopride Hydrochloride, batebulast, Batelapine Maleate, Batimastat, beauvericin, Becanthone Hydrochloride, becaplermin, becliconazole, Beclomethasone Dipropionate, befloxatone, Beinserazide, Belfosdil, *Belladonna*, Beloxamide, Bemesetron, Bemitradine, Bemoradan, Benapryzine Hydrochloride, Benazepril Hydrochloride, Benazeprilat, Bendacalol Mesylate, Bendazac, Bendroflumethiazide, benflumetol, benidipine, Benorterone, Benoxaprofen, Benoxaprofen, Benoxinate Hydrochloride, Benperidol, Bentazepam, Bentiromide, Benurestat, Benzbromarone, Benzethonium Chloride, Benzetimide Hydrochloride, Benzilonium Bromide, Benzindopyrine Hydrochloride, benzisoxazole, Benzocaine, benzochlorins, Benzoctamine Hydrochloride, Benzodepa, benzoidazoxan, Benzonatate, Benzoyl Peroxide, Benzoylpas Calcium, benzoylstaurosporine, Benzquinamide, Benzthiazide, benztropine, Benztropine Mesylate, Benzydamine Hydrochloride, Benzylpenicilloyl Polylysine, bepridil, Bepridil Hydrochloride, Beractant, Beraprost, Berefrine, berlafenone, bertosamil, Berythromycin, besipirdine, beta-alethine, betaclamycin B, Betamethasone, betamipron, betaxolol, Betaxolol Hydrochloride, Bethanechol Chloride, Bethanidine Sulfate, betulinic acid, bevantolol, Bevantolol Hydrochloride, Bezafibrate, bFGF inhibitor, Bialamicol Hydrochloride, Biapenem, Bicalutamide, Bicifadine Hydrochloride, Biclodil Hydrochloride, Bidisomide, bifemelane, Bifonazole, bimakalim, bimithil, Bindarit, Biniramycin, binospirone, bioxalomycin alpha2, Bipenamol Hydrochloride, Biperiden, Biphenamine Hydrochloride, biriperone, bisantrene, bisaramil, bisaziridinylspermine, bis-benzimidazole A, bis-benzimidazole B, bisnafide, Bisobrin Lactate, Bisoprolol, Bispyrithione Magsulfex, bistramide D, bistramide K, bistratene A, Bithionolate Sodium, Bitolterol Mesylate, Bivalirudin, Bizelesin, Bleomycin Sulfate, Bolandiol Dipropionate, Bolasterone, Boldenone Undecylenate, boldine, Bolenol, Bolmantalate, bopindolol, Bosentan, Boxidine, brefeldin, breflate, Brequinar Sodium, Bretazenil, Bretylium Tosylate, Brifentanil Hydrochloride, brimonidine, Brinolase, Brocresine, Brocrinat, Brofoxine, Bromadoline Maleate, Bromazepam, Bromchlorenone, Bromelains, bromfenac, Brominidione, Bromocriptine, Bromodiphenhydramine Hydrochloride, Bromoxamide, Bromperidol, Bromperidol Decanoate, Brompheniramine Maleate, Broperamole, Bropirimine, Brotizolam, Bucainide Maleate, bucindolol, Buclizine Hydrochloride, Bucromarone, Budesonide, budipine, budotitane, Buformin, Bumetamide, Bunaprolast, bunazosin, Bunolol Hydrochloride, Bupicomide, Bupivacaine Hydrochloride, Buprenorphine Hydrochloride, Bupropion Hydrochloride, Buramate, Buserelin Acetate, Buspirone Hydrochloride, Busulfan, Butabarbital, Butacetin, Butaclamol Hydrochloride, Butalbital, Butamben, Butamirate Citrate, Butaperazine, Butaprost, Butedronate Tetrasodium, butenafine, Buterizine, buthionine sulfoximine, Butikacin, Butilfenin, Butirosin Sulfate, Butixirate, butixocort propionate, Butoconazole Nitrate, Butonate, Butopamine, Butoprozine Hydrochloride, Butorphanol, Butoxamine Hydrochloride, Butriptyline Hydrochloride, Cactinomycin, Cadexomer Iodine, Caffeine, calanolide A, Calcifediol, Calcipotriene, calcipotriol, Calcitonin, Calcitriol, Calcium Undecylenate, calphostin C, Calusterone, Cambendazole, camonagrel, camptothecin derivatives, canagliflozin, canarypox IL-2, candesartan, Candicidin, candoxatril, candoxatrilat, Caniglibose, Canrenoate Potassium, Canrenone, capecitabine, Capobenate Sodium, Capobenic Acid, Capreomycin Sulfate, capromab, capsaicin, Captopril, Capuride, Caracemide, Carbachol, Carbadox, Carbamazepine, Carbamide Peroxide, Carbantel Lauryl Sulfate, Carbaspirin Calcium, Carbazeran, carbazomycin C, Carbenicillin Potassium, Carbenoxolone Sodium, Carbetimer, carbetocin, Carbidopa, Carbidopa-Levodopa, Carbinoxamine Maleate, Carbiphene Hydrochloride, Carbocloral, Carbocysteine, Carbol-Fuchsin, Carboplatin, Carboprost, carbovir, carboxamide-amino-triazo-le, carboxyamidotriazole, carboxymethylated beta-1,3-glucan, Carbuterol Hydrochloride, CaRest M3, Carfentanil Citrate, Carisoprodol, Carmantadine, Carmustine, CARN 700, Camidazole, Caroxazone, carperitide, Carphenazine Maleate, Carprofen, Carsatrin Succinate, Cartazolate, carteolol, Carteolol Hydrochloride, cartilage derived inhibitor, Carubicin Hydrochloride, Carumonam Sodium, carvedilol, carvotroline, Carvotroline Hydrochloride, carzelesin, casein kinase inhibitors (ICOS), castanospermine, caurumonam, cebaracetam, cecropin B, Cedefingol, Cefaclor, Cefadroxil, Cefamandole, Cefaparole, Cefatrizine, Cefazaflur Sodium, Cefazolin, Cefbuperazone, cefcapene pivoxil, cefdaloxime pentexil tosilate, Cefdinir, cefditoren pivoxil, Cefepime, cefetamet, Cefetecol, cefixime, cefluprenam, Cefinenoxime Hydrochloride, Cefinetazole, cefminlox, cefodizime, Cefonicid Sodium, Cefoperazone Sodium, Ceforamide, cefoselis, Cefotaxime Sodium, Cefotetan, cefotiam, Cefoxitin, cefozopran, cefpimizole, Cefpiramide, cefpirome, cefpodoxime proxetil, cefprozil, Cefroxadine, cefsulodin, Ceftazidime, cefteram, ceftibuten, Ceftizoxime Sodium, ceftriaxone, Cefuroxime, celastrol, celikalim, celiprolol, cepacidiine A, Cephacetrile Sodium, Cephalexin, Cephaloglycin, Cephaloridine, Cephalothin Sodium, Cephapirin Sodium, Cephradine, cericlamine, cerivastatin, Ceronapril, certoparin sodium, Ceruletide, Cetaben Sodium, Cetalkonium Chloride, Cetamolol Hydrochloride, cetiedil, cetirizine, Cetophenicol, Cetraxate Hydrochloride, cetrorelix, Cetylpyridinium Chloride, Chenodiol, Chlophedianol Hydrochloride, Chloral Betaine, Chlorambucil, Chloramphenicol, Chlordantoin, Chlordiazepoxide, Chlorhexidine Gluconate, chlorins, Chlormadinone Acetate, chlorooorienticin A, Chloroprocaine Hydrochloride, Chloropropamide, Chloroquine, chloroquinoxaline sulfonamide, Chlorothiazide, Chlorotrianisene, Chloroxine, Chloroxylenol, Chlorphenesin Carbamate, Chlorpheniramine Maleate, Chlorpromazine, Chlorpropamide, Chlorprothixene, Chlortetracycline Bisulfate, Chlorthalidone, Chlorzoxazone, Cholestyramine Resin, Chromonar Hydrochloride, cibenzoline, cicaprost, Ciclafrine Hydrochloride, Ciclazindol, ciclesonide, cicletanine, Ciclopirox, Cicloprofen, cicloprolol, Cidofovir, Cidoxepin Hydrochloride, Cifenline, Ciglitazone, Ciladopa Hydrochloride, cilansetron, Cilastatin Sodium, Cilazapril, cilnidipine, Cilobamine Mesylate, cilobradine, Cilofungin, cilostazol, Cimaterol, Cimetidine, cimetropium bromide, Cinalukast, Cinanserin Hydrochloride, Cinepazet Maleate, Cinflumide, Cingestol, cinitapride, Cinnamedrine, Cinnarizine, cinolazepam, Cinoxacin, Cinperene, Cinromide, Cintazone, Cintriamide, Cioteronel, Cipamfylline, Ciprefadol Succinate, Ciprocinonide, Ciprofibrate, Ciprofloxacin, ciprostene, Ciramadol, Cirolemycin, cisapride, cisatracurium besilate, Cisconazole, Cisplatin, cis-porphyrin, cistinexine, citalopram, Citenamide, citicoline, citreamicin alpha, cladribine, Clamoxyquin Hydrochloride, Clarithromycin, clausenamide, Clavulanate Potassium, Clazolam, Clazolimine, clebopride, Clemastine, Clentiazem Maleate, Clidinium Bromide, clinafloxacin, Clindamycin, Clioquinol, Clioxamide, Cliprofen, clobazam, Clobetasol Propionate, Clobetasone Butyrate, Clocortolone Acetate, Clodanolene, Clodazon Hydrochloride, clodronic acid, Clofazimine, Clofibrate, Clofilium Phosphate, Clogestone Acetate, Clomacran Phosphate, Clomegestone Acetate, Clometherone, clomethiazole, clomifene analogues, Clominorex, Clomiphene, Clomipramine Hydrochloride, Clonazepam, Clonidine, Clonitrate, Clonixeril, Clonixin, Clopamide, Clopenthixol, Cloperidone Hydrochloride, clopidogrel, Clopimozide, Clopipazan Mesylate, Clopirac, Cloprednol, Cloprostenol Sodium, Clorazepate Dipotassium, Clorethate, Clorexolone, Cloroperone Hydrochloride, Clorprenaline Hydrochloride, Clorsulon, Clortermine Hydrochloride, Closantel, Closiramine Aceturate, Clothiapine, Clothixamide Maleate Cloticasone Propionate, Clotrimazole, Cloxacillin Benzathine, Cloxyquin, Clozapine, Cocaine, Coccidioidin, Codeine, Codoxime, Colchicine, colestimide, Colestipol Hydrochloride, Colestolone, Colforsin, Colfosceril Palmitate, Colistimethate Sodium, Colistin Sulfate, collismycin A, collismycin B, Colterol Mesylate, combretastatin A4, combretastatin analogue, complestatin, conagenin, Conorphone Hydrochloride, contignasterol, contortrostatin, Cormethasone Acetate, Corticorelin Ovine Triflutate, Corticotropin, Cortisone Acetate, Cortivazol, Cortodoxone, cosalane, costatolide, Cosyntropin, cotinine, Coumadin, Coumermycin, crambescidin 816, Crilvastatin, crisnatol, Cromitrile Sodium, Cromolyn Sodium, Crotamiton, cryptophycin 8, cucumariosid, Cuprimyxin, curacin A, curdlan sulfate, curiosin, Cyclacillin, Cyclazocine, cyclazosin, cyclic HPMPC, Cyclindole, Cycliramine Maleate, Cyclizine, Cyclobendazole, cyclobenzaprine, cyclobut A, cyclobut G, cyclocapron, Cycloguanil Pamoate, Cycloheximide, cyclopentanthraquinones, Cyclopenthiazide, Cyclopentolate Hydrochloride, Cyclophenazine Hydrochloride, Cyclophosphamide, cycloplatam, Cyclopropane, Cycloserine, cyclosin, Cyclosporine, cyclothialidine, Cyclothiazide, cyclothiazomycin, Cyheptamide, cypemycin, Cypenamine Hydrochloride, Cyprazepam, Cyproheptadine Hydrochloride, Cyprolidol Hydrochloride, cyproterone, Cyproximide, Cysteamine, Cysteine Hydrochloride, Cystine, Cytarabine, Cytarabine Hydrochloride, cytarabine ocfosfate, cytochalasin B, cytolytic factor, cytostatin, Dacarbazine, dacliximab, dactimicin, Dactinomycin, daidzein, Daledalin Tosylate, dalfopristin, Dalteparin Sodium, Daltroban, Dalvastatin, danaparoid, Danazol, Dantrolene, dapagliflozin, daphlnodorin A, dapiprazole, dapitant, Dapoxetine Hydrochloride, Dapsone, Daptomycin, Darglitazone Sodium, darifenacin, darlucin A, Darodipine, darsidomine, Daunorubicin Hydrochloride, Dazadrol Maleate, Dazepinil Hydrochloride, Dazmegrel, Dazopride Fumarate, Dazoxiben Hydrochloride, Debrisoquin Sulfate, Decitabine, deferiprone, deflazacort, Dehydrocholic Acid, dehydrodidemnin B, Dehydroepiandrosterone, delapril, Delapril Hydrochloride, Delavirdine Mesylate, delequamine, delfaprazine, Delmadinone Acetate, delmopinol, delphinidin, Demecarium Bromide, Demeclocycline, Demecycline, Demoxepam, Denofungin, deoxypyridinoline, Depakote, deprodone, Deprostil, depsidomycin, deramciclane, dermatan sulfate, Desciclovir, Descinolone Acetonide, Desflurane, Desipramine Hydrochloride, desirudin, Deslanoside, deslorelin, desmopressin, desogestrel, Desonide, Desoximetasone, desoxoamiodarone, Desoxycorticosterone Acetate, detajmium bitartrate, Deterenol Hydrochloride, Detirelix Acetate, Devazepide, Dexamethasone, Dexamisole, Dexbrompheniramine Maleate, Dexchlorpheniramine Maleate, Dexclamol Hydrochloride, Dexetimide, Dexfenfluramine Hydrochloride, dexifosfamide, Deximafen, Dexivacaine, dexketoprofen, dexloxiglumide, Dexmedetomidine, Dexormaplatin, Dexoxadrol Hydrochloride, Dexpanthenol, Dexpemedolac, Dexpropranolol Hydrochloride, Dexrazoxane, dexsotalol, dextrin 2-sulphate, Dextroamphetamine, Dextromethorphan, Dextrorphan Hydrochloride, Dextrothyroxine Sodium, dexverapamil, Dezaguanine, dezinamide, dezocine, Diacetolol Hydrochloride, Diamocaine Cyclamate, Diapamide, Diatrizoate Meglumine, Diatrizoic Acid, Diaveridine, Diazepam, Diaziquone, Diazoxide, Dibenzepin Hydrochloride, Dibenzothiophene, Dibucaine, Dichliorvos, Dichloralphenazone, Dichlorphenamide, Dicirenone, Diclofenac Sodium, Dicloxacillin, dicranin, Dicumarol, Dicyclomine Hydrochloride, Didanosine, didemnin B, didox, Dienestrol, dienogest, Diethylcarbamazine Citrate, diethylhomospermine, diethylnorspermine, Diethylpropion Hydrochloride, Diethylstilbestrol, Difenoximide Hydrochloride, Difenoxin, Diflorasone Diacetate, Difloxacin Hydrochloride, Difluanine Hydrochloride, Diflucortolone, Diflumidone Sodium, Diflunisal, Difluprednate, Diftalone, *Digitalis*, Digitoxin, Digoxin, Dihexyverine Hydrochloride, dihydrexidine, dihydro-5-azacytidine, Dihydrocodeine Bitartrate, Dihydroergotamine Mesylate, Dihydroestosterone, Dihydrostreptomycin Sulfate, Dihydrotachysterol, dihydrotaxol, 9-, Dilantin, Dilevalol Hydrochloride, Diltiazem Hydrochloride, Dimefadane, Dimefline Hydrochloride, Dimenhydrinate, Dimercaprol, Dimethadione, Dimethindene Maleate, Dimethisterone, dimethyl prostaglandin A1, Dimethyl Sulfoxide, dimethylhomospermine, dimiracetam, Dimoxamine Hydrochloride, Dinoprost, Dinoprostone, Dioxadrol Hydrochloride, dioxamycin, Diphenhydramine Citrate, Diphenidol, Diphenoxylate Hydrochloride, diphenyl spiromustine, Dipivefin Hydrochloride, Dipivefrin, dipliencyprone, diprafenone, dipropylnorspermine, Dipyridamole, Dipyrithione, Dipyrone, dirithromycin, discodermolide, Disobutamide, Disofenin, Disopyramide, Disoxaril, disulfiram, Ditekiren, Divalproex Sodium, Dizocilpine Maleate, Dobutamine, docarpamine, Docebenone, Docetaxel, Doconazole, docosanol, dofetilide, dolasetron, Ebastine, ebiratide, ebrotidine, ebselen, ecabapide, ecabet, ecadotril, ecdisteron, echicetin, echistatin, Echothiophate Iodide, Eclanamine Maleate, Eclazolast, ecomustine, Econazole, ecteinascidin 722, edaravone, Edatrexate, edelfosine, Edifolone Acetate, edobacomab, Edoxudine, edrecolomab, Edrophonium Chloride, edroxyprogesteone Acetate, efegatran, eflornithine, efonidipine, egualcen, Elantrine, eleatonin, elemene, eletriptan, elgodipine, eliprodil, Elsamitrucin, eltenae, Elucaine, emalkalim, emedastine, Emetine Hydrochloride, emiglitate, Emilium Tosylate, emitefur, emoctakin, empagliflozin, Enadoline Hydrochloride, enalapril, Enalaprilat, Enalkiren, enazadrem, Encyprate, Endralazine Mesylate, Endrysone, Enflurane, englitazone, Enilconazole, Enisoprost, Enlimomab, Enloplatin, Enofelast, Enolicam Sodium, Enoxacin, enoxacin, enoxaparin sodium, Enoxaparin Sodium, Enoximone, Enpiroline Phosphate, Enprofylline, Enpromate, entacapone, enterostatin, Enviradene, Enviroxime, Ephedrine, Epicillin, Epimestrol, Epinephrine, Epinephryl Borate, Epipropidine, Epirizole, epirubicin, Epitetracycline Hydrochloride, Epithiazide, Epoetin Alfa, Epoetin Beta, Epoprostenol, Epoprostenol Sodium, epoxymexrenone, episteride, Eprosartan, eptastigmine, equilenin, Equilin, Erbulozole, erdosteine, Ergoloid Mesylates, Ergonovine Maleate, Ergotamine Tartrate, ersentilide, Ersofermin, erythritol, Erythrityl Tetranitrate, Erythromycin, Esmolol Hydrochloride, Esorubicin Hydrochloride, Esproquin Hydrochloride, Estazolam, Estradiol, Estramustine, estramustine analogue, Estrazinol Hydrobromide, Estriol, Estrofurate, estrogen agonists, estrogen antagonists, Estrogens, Conjugated Estrogens, Esterified Estrone, Estropipate, esuprone, Etafedrine Hydrochloride, Etanidazole, etanterol, Etarotene, Etazolate Hydrochloride, Eterobarb, ethacizin, Ethacrynate Sodium, Ethacrynic Acid, Ethambutol Hydrochloride, Ethamivan, Ethanolamine Oleate, Etehlorvynol, Ether, Ethinyl estradiol, Ethiodized Oil, Ethionamide, Ethonam Nitrate, Ethopropazine Hydrochloride, Ethosuximide, Ethotoin, Ethoxazene Hydrochloride, Ethybenztropine, Ethyl Chloride, Ethyl Dibunate, Ethylestrenol, Ethyndiol, Ethynerone, Ethynodiol Diacetate, Etibendazole, Etidocaine, Etidronate Disodium, Etidronic Acid, Etifenin, Etintidine Hydrochloride, etizolam, Etodolac, Etofenamate, Etoformin Hydrochloride, Etomidate, Etonogestrel, Etoperidone Hydrochloride, Etoposide, Etoprine, Etoxadrol Hydrochloride, Etozolin, etrabamine, Etretinate, Etryptamine Acetate, Eucatropine Hydrochloride, Eugenol, Euprocin Hydrochloride, eveminomicin, Exametazime, examorelin, Exaprolol Hydrochloride, exemestane, fadrozole, faeriefungin, Famciclovir, Famotidine, Fampridine, fantofarone, Fantridone Hydrochloride, faropenem, fasidotril, fasudil, fazarabine, fedotozine, felbamate, Felbinac, Felodipine, Felypres sin, Fenalamide, Fenamole, Fenbendazole, Fenbufen, Fencibutirol, Fenclofenac, Fenclonine, Fenclorac, Fendosal, Fenestrel, Fenethylline Hydrochloride, Fenfluramine Hydrochloride, Fengabine, Fenimide, Fenisorex, Fenmetozole Hydrochloride, Fenmetramide, Fenobam, Fenoctimine Sulfate, fenofibrate, fenoldopam, Fenoprofen, Fenoterol, Fenpipalone, Fenprinast Hydrochloride, Fenprostalene, Fenquizone, fenretinide, fenspiride, Fentanyl Citrate, Fentiazac, Fenticlor, fenticonazole, Fenyripol Hydrochloride, fepradinol, ferpifosate sodium, ferristene, ferrixan, Ferrous Sulfate, Dried, Ferumoxides, ferumoxsil, Fetoxylate Hydrochloride, fexofenadine, Fezolamine Fumarate, Fiacitabine, Fialuridine, Fibrinogen 1 125, filgrastim, Filipin, finasteride, Flavodilol Maleate, flavopiridol, Flavoxate Hydrochloride, Flazalone, flecainide, flerobuterol, Fleroxacin, flesinoxan, Flestolol Sulfate, Fletazepam, flezelastine, flobufen, Floctafenine, flomoxef, Flordipine, florfenicol, florifenine, flosatidil, Flosequinan, Floxacillin, Floxuridine, fluasterone, Fluazacort, Flubanilate Hydrochloride, Flubendazole, Flucindole, Flucloronide, Fluconazole, Flucytosine, Fludalanine, Fludarabine Phosphate, Fludazonium Chloride, Fludeoxyglucose F 18, Fludorex, Fludrocortisone Acetate, Flufenamic Acid, Flufenisal, Flumazenil, flumecinol, Flumequine, Flumeridone, Flumethasone, Flumetramide, Flumezapine, Fluminorex, Flumizole, Flumoxonide, flunarizine, Flunidazole, Flunisolide, Flunitrazepam, Flunixin, fluocalcitriol, Fluocinolone Acetonide, Fluocinonide, Fluocortin Butyl, Fluocortolone, Fluorescein, fluorodaunorunicin hydrochloride, Fluorodopa F 18, Fluorometholone, Fluorouracil, Fluotracen Hydrochloride, Fluoxetine, Fluoxymesterone, fluparoxan, Fluperamide, Fluperolone Acetate, Fluphenazine Decanoate, flupirtine, Fluprednisolone, Fluproquazone, Fluprostenol Sodium, Fluquazone, Fluradoline Hydrochloride, Flurandrenolide, Flurazepam Hydrochloride, Flurbiprofen, Fluretofen, flurithromycin, Flurocitabine, Flurofamide, Flurogestone Acetate, Flurothyl, Fluroxene, Fluspiperone, Fluspirilene, Fluticasone Propionate, flutrimazole, Flutroline, fluvastatin, Fluvastatin Sodium, fluvoxamine, Fluzinamide, Folic Acid, Follicle regulatory protein, Folliculostatin, Fomepizole, Fonazine Mesylate, forasartan, forfenimex, forfenirmex, formestane, Formocortal, formoterol, Fosarilate, Fosazepam, Foscarnet Sodium, fosfomycin, Fosfonet Sodium, fosinopril, Fosinoprilat, fosphenyloin, Fosquidone, Fostedil, fostriecin, fotemustine, Fuchsin, Basic, Fumoxicillin, Fungimycin, Furaprofen, Furazolidone, Furazolium Chloride, Furegrelate Sodium, Furobufen, Furodazole, Furosemide, Fusidate Sodium, Fusidic Acid, gabapentin, Gadobenate Dimeglumine, gadobenic acid, gadobutrol, Gadodiamide, gadolinium texaphyrin, Gadopentetate Dimegiumine, gadoteric acid, Gadoteridol, Gadoversetamide, galantamine, galdansetron, Galdansetron Hydrochloride, Gallamine Triethiodide, gallium nitrate, gallopamil, galocitabine, Gamfexine, gamolenic acid, Ganciclovir, ganirelix, gelatinase inhibitors, Gemcadiol, Gemcitabine, Gemeprost, Gemfibrozil, Gentamicin Sulfate, Gentian Violet, gepirone, Gestaclone, Gestodene, Gestonorone Caproate, Gestrinone, Gevotroline Hydrochloride, girisopam, glaspimod, glaucocalyxin A, Glemanserin, Gliamilide, Glibornuride, Glicetanile Sodium, Gliflumide, Glimepiride, Glipizide, Gloximonam, Glucagon, glutapyrone, glutathione inhibitors, Glutethimide, Glyburide, glycopine, glycopril, Glycopyrrolate, Glyhexamide, Glymidine Sodium, Glyoctamide, Glyparamide, Gold Au 198, Gonadoctrinins, Gonadorelin, Gonadotropins, Goserelin, Gramicidin, Granisetron, grepafloxacin, Griseofulvin, Guaiapate, Guaithylline, Guanabenz, Guanabenz Acetate, Guanadrel Sulfate, Guancydine, Guanethidine Monosulfate, Guanfacine Hydrochloride, Guanisoquin Sulfate, Guanoclor Sulfate, Guanoctine Hydrochloride, Guanoxabenz, Guanoxan Sulfate, Guanoxyfen Sulfate, Gusperimus Trihydrochloride, Halazepam, Halcinonide, halichondrin B, Halobetasol Propionate, halofantrine, Halofantrine Hydrochloride, Halofenate, Halofuginone Hydrobromide, halomon, Halopemide, Haloperidol, halopredone, Haloprogesterone, Haloprogin, Halothane, Halquinols, Hamycin, Han memopausal gonadotropins, hatomamicin, hatomarubigin A, hatomarubigin B, hatomarubigin C, hatomarubigin D, Heparin Sodium, hepsulfam, heregulin, Hetacillin, Heteronium Bromide, Hexachlorophene: Hydrogen Peroxide, Hexafluorenium Bromide, hexamethylene bisacetamide, Hexedine, Hexobendine, Hexoprenaline Sulfate, Hexylresorcinol, Histamine Phosphate, Histidine, Histoplasmin, Histrelin, Homatropine Hydrobromide, Hoquizil Hydrochloride, Human chorionic gonadotropin, Hycanthone, Hydralazine Hydrochloride, Hydralazine Polistirex, Hydrochlorothiazide, Hydrocodone Bitartrate, Hydrocortisone, Hydroflumethiazide, Hydromorphone Hydrochloride, Hydroxyamphetamine Hydrobromide, Hydroxychloroquine Sulfate, Hydroxyphenamate, Hydroxyprogesterone Caproate, Hydroxyurca, Hydroxyzine Hydrochloride, Hymecromone, Hyoscyamine, hypericin, Ibafloxacin, ibandronic acid, ibogaine, Ibopamine, ibudilast, Ibufenac, Ibuprofen, Ibutilide Fumarate, Icatibant Acetate, Ichthammol, Icotidine, idarubicin, idoxifene, Idoxuridine, idramantone, lemefloxacin, lesopitron, Ifetroban, Ifosfamide, Ilepeimide, illimaquinone, ilmofosine, ilomastat, Ilonidap, iloperidone, iloprost, Imafen Hydrochloride, Imazodan Hydrochloride, imidapril, imidazenil, imidazoacridones, Imidecyl Iodine, Imidocarb Hydrochloride, Imidoline Hydrochloride, Imidurea, Imiloxan Hydrochloride, Imipenem, Imipramine Hydrochloride, imiquimod, immunostimulant peptides, Impromidine Hydrochloride, Indacrinone, Indapamide, Indecainide Hydrochloride, Indeloxazine Hydrochloride, Indigotindisulfonate Sodium, indinavir, Indocyanine Green, Indolapril Hydrochloride, Indolidan, indometacin, Indomethacin Sodium, Indoprofen, indoramin, Indorenate Hydrochloride, Indoxole, Indriline Hydrochloride, inocoterone, inogatran, inolimomab, Inositol Niacinate, Insulin, interferons, interleukins, Intrazole, Intriptyline Hydrochloride, iobenguane, Iobenzamic Acid, iobitridol, locarmate Meglumine, locarmic Acid, locetamic Acid, Iodamide, Iodine, Iodipamide Meglumine, Iodixanol, iodoamiloride, lodoantipyrine I 131, Iodocholesterol I 131, iododoxorubicin, lodohippurate Sodium I 131, Iodopyracet I 125, Iodoquinol, lodoxamate Meglumine, lodoxamie Acid, loglicic Acid, lofetamine Hydrochloride I 123, iofratol, loglucol, loglucomide, loglycamic Acid, logulamide, Iohexol, iomeprol, lomethin I 125, Iopamidol, lopanoic Acid, iopentol, Iophendylate, loprocemic Acid, iopromide, lopronic Acid, lopydol, lopydone, iopyrol, losefamic Acid, loseric Acid, losulamide Meglumine, losumetic Acid, lotasul, lotetric Acid, Iothalamate Sodium, lothalamic Acid, iotriside, lotrolan, lotroxic Acid, lotyrosine I 131, Ioversol, loxagiate Sodium, Ioxaglate Meglumine, loxaglic Acid, ioxilan, loxotrizoic Acid, ipazilide, ipenoxazone, ipidacrine, Ipodate Calcium, ipomeanol, 4-, Ipratropium Bromide, ipriflavone, Iprindole, Iprofenin, Ipronidazole, Iproplatin, Iproxamine Hydrochloride, ipsapirone, irbesartan, irinotecan, irloxacin, iroplact, irsogladine, Irtemazole, isalsteine, Isamoxole, isbogrel, Isepamicin, isobengazole, Isobutamben, Isocarboxazid, Isoconazole, Isoetharine, isofloxythepin, Isofluoredone Acetate, Isoflurane, Isoflurophate, isohomohalicondrin B, Isoleucine, Isomazole Hydrochloride, Isomylamine Hydrochloride, Isoniazid, Isopropamide Iodide, Isopropyl Alcohol, isopropyl unoprostone, Isoproterenol Hydrochloride, Isosorbide, Isosorbide Mononitrate, Isotiquimide, Isotretinoin, Isoxepac, Isoxicam, Isoxsuprine Hydrochloride, isradipine, itameline, itasetron, Itazigrel, itopride, Itraconazole, Ivermectin, jasplakinolide, Josamycin, kahalalide F, Kalafungin, Kanamycin Sulfate, Ketamine Hydrochloride, Ketanserin, Ketazocine, Ketazolam, Kethoxal, Ketipramine Fumarate, Ketoconazole, Ketoprofen, Ketorfanol, ketorolac, Ketotifen Fumarate, Kitasamycin, Labetalol Hydrochloride, Lacidipine, lacidipine, lactitol, lactivicin, laennec, lafutidine, lamellarin-N triacetate, lamifiban, Lamivudine, Lamotrigine, lanoconazole, Lanoxin, lanperisone, lanreotide, Lansoprazole, latanoprost, lateritin, laurocapram, Lauryl Isoquinolinium Bromide, Lavoltidine Succinate, lazabemide, Lecimibide, leinamycin, lemildipine, leminoprazole, lenercept, Leniquinsin, lenograstim, Lenperone, lentinan sulfate, leptin, leptolstatin, lercanidipine, Lergotrile, lerisetron, Letimide Hydrochloride, letrazuril, letrozole, Leucine, leucomyzin, Leuprolide Acetate, leuprolide+estrogen+progesterone, leuprorelin, Levamfetamine Succinate, levamisole, Levdobutamine Lactobionate, Leveromakalim, levetiracetam, Leveycloserine, levobetaxolol, levobunolol, levobupivacaine, levocabastine, levocarnitine, Levodopa, levodropropizine, levofloxacin, Levofuraltadone, Levoleucovorin Calcium, Levomethadyl Acetate, Levomethadyl Acetate Hydrochloride, levomoprolol, Levonantradol Hydrochloride, Levonordefrin, Levonorgestrel, Levopropoxyphene Napsylate, Levopropylcillin Potassium, levormeloxifene, Levorphanol Tartrate, levosimendan, levosulpiride, Levothyroxine Sodium, Levoxadrol Hydrochloride, Lexipafant, Lexithromycin, liarozole, Libenzapril, Lidamidine Hydrochloride, Lidocaine, Lidofenin, Lidoflazine, Lifarizine, Lifibrate, Lifibrol, Linarotene, Lincomycin, linear polyamine analogue, Linogliride, Linopirdine, linotroban, linsidomine, lintitript, lintopride, Liothyronine I 125, liothyronine sodium, Liotrix, lirexapride, lisinopril, lissoclinamide 7, Lixazinone Sulfate, lobaplatin, Lobenzarit Sodium, Lobucavir, Lodelaben, lodoxamide, Lofemizole Hydrochloride, Lofentanil Oxalate, Lofepramine Hydrochloride, Lofexidine Hydrochloride, lombricine, Lomefloxacin, lomerizine, Lometraline Hydrochloride, lometrexol, Lomofungin, Lomoxicam, Lomustine, Lonapalene, lonazolac, lonidamine, Loperamide Hydrochloride, loracarbef, Lorajmine Hydrochloride, loratadine, Lorazepam, Lorbamate, Lorcainide Hydrochloride, Loreclezole, Loreinadol, lorglumide, Lormetazepam, Lornoxicam, lornoxicam, Lortalamine, Lorzafone, losartan, losigamone, losoxantrone, Losulazine Hydrochloride, loteprednol, lovastatin, loviride, Loxapine, Loxoribine, lubeluzole, Lucanthone Hydrochloride, Lufironil, Lurosetron Mesylate, lurtotecan, luteinizing hormone, lurasidone, lutetium, Lutrelin Acetate, luzindole, Lyapolate Sodium, Lycetamine, lydicamycin, Lydimycin, Lynestrenol, Lypressin, Lysine, lysofylline, lysostaphin, lytic peptides, Maduramicin, Mafenide, magainin 2 amide, Magnesium Salicylate, Magnesium Sulfate, magnolol, maitansine, Malethamer, mallotochromene, mallotojaponin, Malotilate, malotilate, mangafodipir, manidipine, maniwamycin A, Mannitol, mannostatin A, manumycin E, manumycin F, mapinastine, Maprotiline, marimastat, Martek 8708, Martek 92211, Masoprocol, maspin, massetolide, matrilysin inhibitors, Maytansine, Mazapertine Succiniate, Mazindol, Mebendazole, Mebeverine Hydrochloride, Mebrofenin, Mebutamate, Mecamylamine Hydrochloride, Mechlorethamine Hydrochloride, Meclocycline, Meclofenamate Sodium, Mecloqualone, Meclorisone Dibutyrate, Medazepam Hydrochloride, Medorinone, Medrogestone, Medroxalol, Medroxyprogesterone, Medrysone, Meelizine Hydrochloride, Mefenamic Acid, Mefenidil, Mefenorex Hydrochloride, Mefexamide, Mefloquine Hydrochloride, Mefruside, Megalomicin Potassium Phosphate, Megestrol Acetate, Meglumine, Meglutol, Melengestrol Acetate, Melitracen Hydrochloride, Melphalan, Memotine Hydrochloride, Menabitan Hydrochloride, Menoctone, menogaril, Menotropins, Meobentine Sulfate, Mepartricin, Mepenzolate Bromide, Meperidine Hydrochloride, Mephentermine Sulfate, Mephenyloin, Mephobarbital, Mepivacaine Hydrochloride, Meprobamate, Meptazinol Hydrochloride, Mequidox, Meralein Sodium, merbarone, Mercaptopurine, Mercufenol Chloride, Mercury, Ammoniated, Merisoprol Hg 197, Meropenem, Mesalamine, Meseclazone, Mesoridazine, Mesterolone, Mestranol, Mesuprine Hydrochloride, Metalol Hydrochloride, Metaproterenol Polistirex, Metaraminol Bitartrate, Metaxalone, Meteneprost, meterelin, Metformin, Methacholine Chloride, Methacycline, Methadone Hydrochloride, Methadyl Acetate, Methalthiazide, Methamphetamine Hydrochloride, Methaqualone, Methazolamide, Methdilazine, Methenamine, Methenolone Acetate, Methetoin, Methicillin Sodium, Methimazole, methioninase, Methionine, Methisazone, Methixene Hydrochloride, Methocarbamol, Methohexital Sodium, Methopholine, Methotrexate, Methotrimeprazine, methoxatone, Methoxyflurane, Methsuximide, Methyclothiazide, Methyl Palmoxirate, Methylatropine Nitrate, Methylbenzethonium Chloride, Methyldopa, Methyldopate Hydrochloride, Methylene Blue, Methylergonovine Maleate, methylhistamine, R-alpha, methylinosine monophosphate, Methylphenidate Hydrochloride, Methylprednisolone, Methyltestosterone, Methynodiol Diacetate, Methysergide, Methysergide Maleate, Metiamide, Metiapine, Metioprim, metipamide, Metipranolol, Metizoline Hydrochloride, Metkephamid Acetate, metoclopramide, Metocurine Iodide, Metogest, Metolazone, Metopimazine, Metoprine, Metoprolol, Metoquizine, metrifonate, Metrizamide, Metrizoate Sodium, Metronidazole, Meturedepa, Metyrapone, Metyrosine, Mexiletine Hydrochloride, Mexrenoate Potassium, Mezlocillin, mfonelic Acid, Mianserin Hydrochloride, mibefradil, Mibefradil Dihydrochloride, Mibolerone, michellamine B, Miconazole, microcolin A, Midaflur, Midazolam Hydrochloride, midodrine, mifepristone, Mifobate, miglitol, milacemide, milameline, mildronate, Milenperone, Milipertine, milnacipran, Milrinone, miltefosine, Mimbane Hydrochloride, minaprine, Minaxolone, Minocromil, Minocycline, Minoxidil, Mioflazine Hydrochloride, miokamycin, mipragoside, mirfentanil, mirimostim, Mirincamycin Hydrochloride, Mirisetron Maleate, Mirtazapine, mismatched double stranded RNA, Misonidazole, Misoprostol, Mitindomide, Mitocarcin, Mitocromin, Mitogillin, mitoguazone, mitolactol, Mitomalcin, Mitomycin, mitonafide, Mitosper, Mitotane, mitoxantrone, mivacurium chloride, mivazerol, mixanpril, Mixidine, mizolastine, mizoribine, Moclobemide, modafinil, Modaline Sulfate, Modecainide, moexipril, mofarotene, Mofegiline Hydrochloride, mofezolac, molgramostim, Molinazone, Molindone Hydrochloride, Molsidomine, mometasone, Monatepil Maleate, Monensin, Monoctanoin, Montelukast Sodium, montirelin, mopidamol, moracizine, Morantel Tartrate, Moricizine, Morniflumate, Morphine Sulfate, Morrhuate Sodium, mosapramine, mosapride, motilide, Motretinide, Moxalactam Disodium, Moxazocine, moxiraprine, Moxnidazole, moxonidine, Mumps Skin Test Antigen, mustard anticancer agent, Muzolimine, mycaperoxide B, Mycophenolic Acid, myriaporone, Nabazenil, Nabilone, Nabitan Hydrochloride, Naboctate Hydrochloride, Nabumetone, N-acetyldinaline, Nadide, nadifloxacin, Nadolol, nadroparin calcium, nafadotride, nafamostat, nafarelin, Nafcillin Sodium, Nafenopin, Nafimidone Hydrochloride, Naflocort, Nafomine Malate, Nafoxidine Hydrochloride, Nafronyl Oxalate, Naftifine Hydrochloride, naftopidil, naglivan, nagrestip, Nalbuphine Hydrochloride, Naldemedine, Nalidixate Sodium, Nalidixic Acid, nalmefene, Nalmexone Hydrochloride, naloxone+pentazocine, Naltrexone, Namoxyrate, Nandrolone Phenpropionate, Nantradol Hydrochloride, Napactadine Hydrochloride, napadisilate, Napamezole Hydrochloride, napaviin, Naphazoline Hydrochloride, naphterpin, Naproxen, Naproxol, napsagatran, Naranol Hydrochloride, Narasin, naratriptan, nartograstim, nasaruplase, Natamycin, nateplase, Naxagolide Hydrochloride, Nebivolol, Nebramycin, nedaplatin, Nedocromil, Nefazodone Hydrochloride, Neflumozide Hydrochloride, Nefopam Hydrochloride, Nelezaprine Maleate, Nemazoline Hydrochloride, nemorubicin, Neomycin Palmitate, Neostigmine Bromide, neridronic acid, Netilmicin Sulfate, neutral endopeptidase, Neutramycin, Nevirapine, Nexeridine Hydrochloride, Niacin, Nibroxane, Nicardipine Hydrochloride, Nicergoline, Niclosamide, Nicorandil, Nicotinyl Alcohol, Nifedipine, Nifirmerone, Nifluridide, Nifuradene, Nifuraldezone, Nifuratel, Nifuratrone, Nifurdazil, Nifurimide, Nifurpirinol, Nifurquinazol, Nifurthiazole, nilutamide, Nilvadipine, Nimazone, Nimodipine, niperotidine, niravoline, Niridazole, nisamycin, Nisbuterol Mesylate, nisin, Nisobamate, Nisoldipine, Nisoxetine, Nisterime Acetate, Nitarsone, nitazoxamide, nitecapone, Nitrafudam Hydrochloride, Nitralamine Hydrochloride, Nitramisole Hydrochloride, Nitrazepam, Nitrendipine, Nitrocycline, Nitrodan, Nitrofurantoin, Nitrofurazone, Nitroglycerin, Nitromersol, Nitromide, Nitromifene Citrate, Nitrous Oxide, nitroxide antioxidant, nitrullyn, Nivazol, Nivimedone Sodium, Nizatidine, Noberastine, Nocodazole, Nogalamycin, Nolinium Bromide, Nomifensine Maleate, Noracymethadol Hydrochloride, Norbolethone, Norepinephrine Bitartrate, Norethindrone, Norethynodrel, Norfloxacin, Norflurane, Norgestimate, Norgestomet, Norgestrel, Nortriptyline Hydrochloride, Noscapine, Novobiocin Sodium, N-substituted benzaimides, Nufenoxole, Nylestriol, Nystatin, O6-benzylguanine, Obidoxime Chloride, Ocaperidone, Ocfentanil Hydrochloride, Ocinaplon, Octanoic Acid, Octazamide, Octenidine Hydrochloride, Octodrine, Octreotide, Octriptyline Phosphate, Ofloxacin, Oformine, okicenone, Olanzapine, oligonucleotides, olopatadine, olprinone, olsalazine, Olsalazine Sodium, Olvanil, omeprazole, onapristone, ondansetron, Ontazolast, Oocyte maturation inhibitor, Opipramol Hydrochloride, oracin, Orconazole Nitrate, Orgotein, Orlislat, Ormaplatin, Ormetoprim, Ornidazole, Orpanoxin, Orphenadrine Citrate, osaterone, otenzepad, Oxacillin Sodium, Oxagrelate, oxaliplatin, Oxamarin Hydrochloride, oxamisole, Oxamniquine, oxandrolone, Oxantel Pamoate, Oxaprotiline Hydrochloride, Oxaprozin, Oxarbazole, Oxatomide, oxaunomycin, Oxazepam, oxcarbazepine, Oxendolone, Oxethazaine, Oxetorone Fumarate, Oxfendazole, Oxfenicine, Oxibendazole, oxiconazole, Oxidopamine, Oxidronic Acid, Oxifungin Hydrochloride, Oxilorphan, Oximonam, Oximonam Sodium, Oxiperomide, oxiracetam, Oxiramide, Oxisuran, Oxmetidine Hydrochloride, oxodipine, Oxogestone Phenpropionate, Oxolinic Acid, Oxprenolol Hydrochloride, Oxtriphylline, Oxybutynin Chloride, Oxychlorosene, Oxycodone, Oxymetazoline Hydrochloride, Oxymetholone, Oxymorphone Hydrochloride, Oxypertine, Oxyphenbutazone, Oxypurinol, Oxytetracycline, Oxytocin, ozagrel, Ozolinone, Paclitaxel, palauamine, Paldimycin, palinavir, palmitoylrhizoxin, Palmoxirate Sodium, pamaqueside, Pamatolol Sulfate, pamicogrel, Pamidronate Disodium, pamidronic acid, Panadiplon, panamesine, panaxytriol, Pancopride, Pancuronium Bromide, panipenem, pannorin, panomifene, pantethine, pantoprazole, Papaverine Hydrochloride, parabactin, Parachlorophenol, Paraldehyde, Paramethasone Acetate, Paranyline Hydrochloride, Parapenzolate Bromide, Pararosaniline Pamoate, Parbendazole, Parconazole Hydrochloride, Paregoric, Pareptide Sulfate, Pargyline Hydrochloride, parnaparin sodium, Paromomycin Sulfate, Paroxetine, parthenolide, Partricin, Paulomycin, pazelliptine, Pazinaclone, Pazoxide, pazufloxacin, pefloxacin, pegaspargase, Pegorgotein, Pelanserin Hydrochloride, peldesine, Peliomycin, Pelretin, Pelrinone Hydrochloride, Pemedolac, Pemerid Nitrate, pemirolast, Pemoline, Penamecillin, Penbutolol Sulfate, Penciclovir, Penfluridol, Penicillin G Benzathine, Penicillin G Potassium, Penicillin G Procaine, Penicillin G Sodium, Penicillin V, Penicillin V Benzathine, Penicillin V Hydrabamine, Penicillin V Potassium, Pentabamate, Pentaerythritol Tetranitrate, pentafuside, pentamidine, pentamorphone, Pentamustine, Pentapiperium Methylsulfate, Pentazocine, Pentetic Acid, Pentiapine Maleate, pentigetide, Pentisomicin, Pentizidone Sodium, Pentobarbital, Pentomone, Pentopril, pentosan, pentostatin, Pentoxifylline, Pentrinitrol, pentrozole, Peplomycin Sulfate, Pepstatin, perflubron, perfofamide, Perfosfamide, pergolide, Perhexiline Maleate, perillyl alcohol, Perindopril, perindoprilat, Perlapine, Permethrin, perospirone, Perphenazine, Phenacemide, phenaridine, phenazinomycin, Phenazopyridine Hydrochloride, Phenbutazone Sodium Glycerate, Phencarbamide, Phencyclidine Hydrochloride, Phendimetrazine Tartrate, Phenelzine Sulfate, Phenmetrazine Hydrochloride, Phenobarbital, Phenoxybenzamine Hydrochloride, Phenprocoumon, phenserine, phensuccinal, Phensuximide, Phentermine, Phentermine Hydrochloride, phentolamine mesilate, Phentoxifylline, Phenyl Aminosalicylate, phenylacetate, Phenylalanine, phenylalanyl ketoconazole, Phenylbutazone, Phenylephrine Hydrochloride, Phenylpropanolamine Hydrochloride, Phenylpropanolamine Polistirex, Phenyramidol Hydrochloride, Phenyloin, phosphatase inhibitors, Physostigmine, picenadol, picibanil, Picotrin Diolamine, picroliv, picumeterol, pidotimod, Pifamine, Pilocarpine, pilsicainide, pimagedine, Pimetine Hydrochloride, pimilprost, Pimobendan, Pimozide, Pinacidil, Pinadoline, Pindolol, pinnenol, pinocebrin, Pinoxepin Hydrochloride, pioglitazone, Pipamperone, Pipazethate, pipecuronium bromide, Piperacetazine, Piperacillin Sodium, Piperamide Maleate, piperazine, Pipobroman, Piposulfan, Pipotiazine Palmitate, Pipoxolan Hydrochloride, Piprozolin, Piquindone Hydrochloride, Piquizil Hydrochloride, Piracetam, Pirandamine Hydrochloride, pirarubicin, Pirazmonam Sodium, Pirazolac, Pirbenicillin Sodium, Pirbuterol Acetate, Pirenperone, Pirenzepine Hydrochloride, piretamide, Pirfenidone, Piridicillin Sodium, Piridronate Sodium, Piriprost, piritrexim, Pirlimycin Hydrochloride, pirlindole, pirmagrel, Pirmenol Hydrochloride, Pirnabine, Piroctone, Pirodavir, pirodomast, Pirogliride Tartrate, Pirolate, Pirolazamide, Piroxantrone Hydrochloride, Piroxicam, Piroximone, Pirprofen, Pirquinozol, Pirsidomine, Prenylamine, Pituitary, Posterior, Pivampicillin Hydrochloride, Pivopril, Pizotyline, placetin A, platinum compounds, platinum-triamine complex, Plicamycin, Plomestane, Pobilukast Edamine, Podofilox, Poisonoak Extract, Poldine Methylsulfate, Poliglusam, Polignate Sodium, Polymyxin B Sulfate, Polythiazide, Ponalrestat, Porfimer Sodium, Porfiromycin, Potassium Chloride, Potassium Iodide, Potassium Permanganate, Povidone-Iodine, Practolol, Pralidoxime Chloride, Pramiracetam Hydrochloride, Pramoxine Hydrochloride, Pranolium Chloride, Pravadoline Maleate, Pravastatin (Pravachol), Prazepam, Prazo sin, Prazosin Hydrochloride, Prednazate, Prednicarbate, Prednimustine, Prednisolone, Prednisone, Prednival, Pregnenolone Succiniate, Prenalterol Hydrochloride, Pridefine Hydrochloride, Prifelone, Prilocalne Hydrochloride, Prilosec, Primaquine Phosphate, Primidolol, Primidone, Prinivil, Prinomide Tromethamine, Prinoxodan, Prizidilol Hydrochloride, Proadifen Hydrochloride, Probenecid, Probicromil Calcium, Probucol, Procainamide Hydrochloride, Procaine Hydrochloride, Procarbazine Hydrochloride, Procaterol Hydrochloride, Prochlorperazine, Procinonide, Proclonol, Procyclidine Hydrochloride, Prodilidine Hydrochloride, Prodolic Acid, Profadol Hydrochloride, Progabide, Progesterone, Proglumide, Proinsulin Human, Proline, Prolintane Hydrochloride, Promazine Hydrochloride, Promethazine Hydrochloride, Propafenone Hydrochloride, propagermanium, Propanidid, Propantheline Bromide, Proparacaine Hydrochloride, Propatyl Nitrate, propentofylline, Propenzolate Hydrochloride, Propikacin, Propiomazine, Propionic Acid, propionylcarnitine, L-, propiram, propiram+paracetamol, propiverine, Propofol, Propoxycaine Hydrochloride, Propoxyphene Hydrochloride, Propranolol Hydrochloride, Propulsid, propyl bis-acridone, Propylhexedrine, Propyliodone, Propylthiouracil, Proquazone, Prorenoate Potassium, Proroxan Hydrochloride, Proscillaridin, Prostalene, prostratin, Protamine Sulfate, protegrin, Protirelin, protosufloxacin, Protriptyline Hydrochloride, Proxazole, Proxazole Citrate, Proxicromil, Proxorphan Tartrate, prulifloxacin, Pseudoephedrine Hydrochloride, Puromycin, purpurins, Pyrabrom, Pyrantel Pamoate, Pyrazinamide, Pyrazofurin, pyrazoloacridine, Pyridostigmine Bromide, Pyrilamine Maleate, Pyrimethamine, Pyrinoline, Pyrithione Sodium, Pyrithione Zinc, Pyrovalerone Hydrochloride, Pyroxamine Maleate, Pyrrocaine, Pyrroliphene Hydrochloride, Pyrrolnitrin, Pyrvinium Pamoate, Quadazocine Mesylate, Quazepam, Quazinone, Quazodine, Quazolast, quetiapine, quiflapon, quinagolide, Quinaldine Blue, quinapril, Quinaprilat, Quinazosin Hydrochloride, Quinbolone, Quinctolate, Quindecamine Acetate, Quindonium Bromide, Quinelorane Hydrochloride, Quinestrol, Quinfamide, Quingestanol Acetate, Quingestrone, Quinidine Gluconate, Quinielorane Hydrochloride, Quinine Sulfate, Quinpirole Hydrochloride, Quinterenol Sulfate, Quinuclium Bromide, Quinupristin, Quipazine Maleate, Rabeprazole Sodium, Racephenicol, Racepinephrine, raf antagonists, Rafoxamide, Ralitoline, raloxifene, raltitrexed, ramatroban, Ramipril, Ramoplanin, ramosetron, ranelic acid, Ranimycin, Ranitidine, ranolazine, Rauwolfia *Serpentina*, recainam, Recainam Hydrochloride, Reclazepam, regavirumab, Regramostim, Relaxin, Relomycin, Remacemide Hydrochloride, Remifentanil Hydrochloride, Remiprostol, Remoxipride, Repirinast, Repromicin, Reproterol Hydrochloride, Reserpine, resinferatoxin, Resorcinol, retelliptine demethylated, reticulon, reviparin sodium, revizinone, rhenium Re 186 etidronate, rhizoxin, Ribaminol, Ribavirin, Riboprine, ribozymes, ricasetron, Ridogrel, Rifabutin, Rifametane, Rifamexil, Rifamide, Rifampin, Rifapentine, Rifaximin, RII retinamide, rilopirox, Riluzole, rimantadine, Rimcazole Hydrochloride, Rimexolone, Rimiterol Hydrobromide, rimoprogin, riodipine, Rioprostil, Ripazepam, ripisartan, Risedronate Sodium, risedronic acid, Risocaine, Risotilide Hydrochloride, rispenzepine, Risperdal, Risperidone, Ritanserin, ritipenem, Ritodrine, Ritolukast, ritonavir, rizatriptan benzoate, Rocastine Hydrochloride, Rocuronium Bromide, Rodocaine, Roflurane, Rogletimide, rohitukine, rokitamycin, Roletamicide, Rolgamidine, Rolicyprine, Rolipram, Rolitetracycline, Rolodine, Romazarit, romurtide, Ronidazole, ropinirole, Ropitoin Hydrochloride, ropivacaine, Ropizine, roquinimex, Rosaramicin, rosiglitazone, Rosoxacin, Rotoxamine, roxaitidine, Roxarsone, roxindole, roxithromycin, rubiginone B1, ruboxyl, rufloxacin, rupatidine, Rutamycin, ruzadolane, Sabeluzole, safingol, safironil, saintopin, salbutamol, R-Salcolex, Salethamide Maleate, Salicyl Alcohol, Salicylamide, Salicylate Meglumine, Salicylic Acid, Salmeterol, Salnacediin, Salsalate, sameridine, sampatrilat, Sancycline, sanfetrinem, Sanguinarium Chloride, Saperconazole, saprisartan, sapropterin, saquinavir, Sarafloxacin Hydrochloride, Saralasin Acetate, SarCNU, sarcophytol A, sargramostim, Sarmoxicillin, Sarpicillin, sarpogrelate, saruplase, saterinone, satigrel, satumomab pendetide, Schick Test Control, Scopafungin, Scopolamine Hydrobromide, Scrazaipine Hydrochloride, Sdi 1 mimetics, Secalciferol, Secobarbital, Seelzone, Seglitide Acetate, selegiline, Selegiline Hydrochloride, Selenium Sulfide, Selenomethionine Se 75, Selfotel, sematilide, semduramicin, semotiadil, semustine, sense oligonucleotides, Sepazonium Chloride, Seperidol Hydrochloride, Seprilose, Seproxetine Hydrochloride, Seractide Acetate, Sergolexole Maleate, Serine, Sermetacin, Sermorelin Acetate, sertaconazole, sertindole, sertraline, setiptiline, Setoperone, sevirumab, sevoflurane, sezolamide, Sibopirdine, Sibutramine Hydrochloride, signal transduction inhibitors, Silandrone, silipide, silteplase, Silver Nitrate, simendan, Simtrazene, Simvastatin, Sincalide, Sinefungin, sinitrodil, sinnabidol, sipatrigine, sirolimus, Sisomicin, Sitogluside, sizofiran, sobuzoxane, Sodium Amylosulfate, Sodium Iodide I 123, Sodium Nitroprusside, Sodium Oxybate, sodium phenylacetate, Sodium Salicylate, solverol, Solypertine Tartrate, Somalapor, Somantadine Hydrochloride, somatomedin B, somatomedin C, somatrem, somatropin, Somenopor, Somidobove, sonermin, Sorbinil, Sorivudine, sotalol, Soterenol Hydrochloride, Sparfloxacin, Sparfosate Sodium, sparfosic acid, Sparsomycin, Sparteine Sulfate, Spectinomycin Hydrochloride, spicamycin D, Spiperone, Spiradoline Mesylate, Spiramycin, Spirapril Hydrochloride, Spiraprilat, Spirogermanium Hydrochloride, Spiromustine, Spironolactone, Spiroplatin, Spiroxasone, splenopentin, spongistatin 1, Sprodiamide, squalamine, Stallimycin Hydrochloride, Stannous Pyrophosphate, Stannous Sulfur Colloid, Stanozolol, Statolon, staurosporine, stavudine, Steffimycin, Stenbolone Acetate, stepronin, Stilbazium Iodide, Stilonium Iodide, stipiamide, Stiripentol, stobadine, Streptomycin Sulfate, Streptonicozid, Streptonigrin, Streptozocin, stromelysin inhibitors, Strontium Chloride Sr 89, succibun, Succimer, Succinylcholine Chloride, Sucralfate, Sucrosofate Potassium, Sudoxicam, Sufentanil, Sufotidine, Sulazepam, Sulbactam Pivoxil, Sulconazole Nitrate, Sulfabenz, Sulfabenzamide, Sulfacetamide, Sulfacytine, Sulfadiazine, Sulfadoxine, Sulfalene, Sulfamerazine, Sulfameter, Sulfamethazine, Sulfamethizole, Sulfamethoxazole, Sulfamonomethoxine, Sulfamoxole, Sulfanilate Zinc, Sulfanitran, sulfasalazine, Sulfasomizole, Sulfazamet, Sulfinalol Hydrochloride, sulfinosine, Sulfinpyrazone, Sulfisoxazole, Sulfomyxin, Sulfonterol Hydrochloride, sulfoxamine, Sulinldac, Sulmarin, Sulnidazole, Suloctidil, Sulofenur, sulopenem, Suloxifen Oxalate, Sulpiride, Sulprostone, sultamicillin, Sulthiame, sultopride, sulukast, Sumarotene, sumatriptan, Suncillin Sodium, Suproclone, Suprofen, suradista, suramin, Surfomer, Suricainide Maleate, Suritozole, Suronacrine Maleate, Suxemerid Sulfate, swainsonine, symakalim, Symclosene, Symetine Hydrochloride, synthetic glycosaminoglycans, Taciamine Hydrochloride, Tacrine Hydrochloride, Tacrolimus, Talampicillin Hydrochloride, Taleranol, Talisomycin, tallimustine, Talmetacin, Talniflumate, Talopram Hydrochloride, Talosalate, Tametraline Hydrochloride, Tamoxifen, Tampramine Fumarate, Tamsulosin Hydrochloride, Tandamine Hydrochloride, tandospirone, tapgen, taprostene, Tasosartan, tauromustine, Taxane, Taxoid, Tazadolene Succinate, tazanolast, tazarotene, Tazifylline Hydrochloride, Tazobactam, Tazofelone, Tazolol Hydrochloride, Tebufelone, Tebuquine, Technetium Tc 99 m Bicisate, Teclozan, Tecogalan Sodium, Teecleukin, Teflurane, Tegafur, Tegretol, Teicoplanin, telenzepine, tellurapyrylium, telmesteine, telmisartan, telomerase inhibitors, Teloxantrone Hydrochloride, Teludipine Hydrochloride, Temafloxacin Hydrochloride, Tematropium Methyl sulfate, Temazepam, Temelastine, temocapril, Temocillin, temoporfin, temozolomide, Tenidap, Teniposide, tenosal, tenoxicam, tepirindole, Tepoxalin, Teprotide, terazosin, Terbinafine, Terbutaline Sulfate, Terconazole, terfenadine, terflavoxate, terguride, Teriparatide Acetate, terlakiren, terlipressin, terodiline, Teroxalene Hydrochloride, Teroxirone, tertatolol, Tesicam, Tesimide, Testolactone, Testosterone, Tetracaine, tetrachlorodecaoxide, Tetracycline, Tetrahydrozoline Hydrochloride, Tetramisole Hydrochloride, Tetrazolast Meglumine, tetrazomine, Tetrofosmin, Tetroquinone, Tetroxoprim, Tetrydamine, thaliblastine, Thalidomide, Theofibrate, Theophylline, Thiabendazole, Thiamiprine, Thiamphenicol, Thiamylal, Thiazesim Hydrochloride, Thiazinamium Chloride, Thiethylperazine, Thimerfonate Sodium, Thimerosal, thiocoraline, thiofedrine, Thioguanine, thiomarinol, Thiopental Sodium, thioperamide, Thioridazine, Thiotepa, Thiothixene, Thiphenamil Hydrochloride, Thiphencillin Potassium, Thiram, Thozalinone, Threonine, Thrombin, thrombopoietin, thrombopoietin mimetic, thymalfasin, thymopoietin receptor agonist, thymotrinan, Thyromedan Hydrochloride, Thyroxine 1 125, Thyroxine 1 131, Tiacrilast, Tiacrilast Sodium, tiagabine, Tiamenidine, tianeptine, tiapafant, Tiapamil Hydrochloride, Tiaramide Hydrochloride, Tiazofurin, Tibenelast Sodium, Tibolone, Tibric Acid, Ticabesone Propionate, Ticarbodine, Ticarcillin Cresyl Sodium, Ticlatone, ticlopidine, Ticrynafen, tienoxolol, Tifurac Sodium, Tigemonam Dicholine, Tigestol, Tiletamine Hydrochloride, Tilidine Hydrochloride, tilisolol, tilnoprofen arbamel, Tilorone Hydrochloride, Tiludronate Disodium, tiludronic acid, Timefurone, Timobesone Acetate, Timolol, tin ethyl etiopurpurin, Tinabinol, Timidazole, Tinzaparin Sodium, Tioconazole, Tiodazosin, Tiodonium Chloride, Tioperidone Hydrochloride, Tiopinac, Tiospirone Hydrochloride, Tiotidine, tiotropium bromide, Tioxidazole, Tipentosin Hydrochloride, Tipredane, Tiprenolol Hydrochloride, Tiprinast Meglumine, Tipropidil Hydrochloride, Tiqueside, Tiquinamide Hydrochloride, tirandalydigin, Tirapazamine, tirilazad, tirofiban, tiropramide, titanocene dichloride, Tixanox, Tixocortol Pivalate, Tizanidine Hydrochloride, Tobramycin, Tocainide, Tocamphyl, Tofenacin Hydrochloride, Tolamolol, Tolazamide, Tolazoline Hydrochloride, Tolbutamide, Tolcapone, Tolciclate, Tolfamide, Tolgabide, lamotrigine, Tolimidone, Tolindate, Tolmetin, Tolnaftate, Tolpovidone 1 131, Tolpyrramide, Tolrestat, Tomelukast, Tomoxetine Hydrochloride, Tonazocine Mesylate, Topiramate, topotecan, Topotecan Hydrochloride, topsentin, Topterone, Toquizine, torasemide, toremifene, Torsemide, Tosifen, Tosufloxacin, totipotent stem cell factor, Tracazolate, trafermin, Tralonide, Tramadol Hydrochloride, Tramazoline Hydrochloride, trandolapril, Tranexamic Acid, Tranilast, Transcainide, translation inhibitors, traxanox, Trazodone Hydrochloride, Trazodone-HCL, Trebenzomine Hydrochloride, Trefentanil Hydrochloride, Treloxinate, Trepipam Maleate, Trestolone Acetate, tretinoin, Triacetin, triacetyluridine, Triafungin, Triamcinolone, Triampyzine Sulfate, Triamterene, Triazolam, Tribenoside, tricaprilin, Tricetamide, Trichlormethiazide, trichohyalin, triciribine, Tricitrates, Triclofenol piperazine, Triclofos Sodium, Triclonide, trientine, Trifenagrel, triflavin, Triflocin, Triflubazam, Triflumidate, Trifluoperazine Hydrochloride, Trifluperidol, Triflupromazine, Triflupromazine Hydrochloride, Trifluridine, Trihexyphenidyl Hydrochloride, Trilostane, Trimazosin Hydrochloride, trimegestone, Trimeprazine Tartrate, Trimethadione, Trimethaphan Camsylate, Trimethobenzamide Hydrochloride, Trimethoprim, Trimetozine, Trimetrexate, Trimipramine, Trimoprostil, Trimoxamine Hydrochloride, Triolein 1 125, Triolein 1 131, Trioxifene Mesylate, Tripamide, Tripelennamine Hydrochloride, Triprolidine Hydrochloride, Triptorelin, Trisulfapyrimidines, Troclosene Potassium, troglitazone, Trolamine, Troleandomycin, trombodipine, trometamol, Tropanserin Hydrochloride, Tropicamide, tropine ester, tropisetron, trospectomycin, trovafloxacin, trovirdine, Tryptophan, Tuberculin, Tubocurarine Chloride, Tubulozole Hydrochloride, tucarcsol, tulobuterol, turosteride, Tybamate, tylogenin, Tyropanoate Sodium, Tyrosine, Tyrothricin, tyrphostins, ubenimex, Uldazepam, Undecylenic Acid, Uracil Mustard, urapidil, Urea, Uredepa, uridine triphosphate, Urofollitropin, Urokinase, Ursodiol, valaciclovir, Valine, Valnoctamide, Valproate Sodium, Valproic Acid, valsartan, vamicamide, vanadeine, Vancomycin, vaninolol, Vapiprost Hydrochloride, Vapreotide, variolin B, Vasopressin, Vecuronium Bromide, velaresol, Velnacrine Maleate, venlafaxine, Veradoline Hydrochloride, veramine, Verapamil Hydrochloride, verdins, Verilopam Hydrochloride, Verlukast, Verofylline, veroxan, verteporfin, Vesnarinone, vexibinol, Vidarabine, vigabatrin, Viloxazine Hydrochloride, Vinblastine Sulfate, vinburnine citrate, Vincofos, vinconate, Vincristine Sulfate, Vindesine, Vindesine Sulfate, Vinepidine Sulfate, Vinglycinate Sulfate, Vinleurosine Sulfate, vinorelbine, vinpocetine, vintoperol, vinxaltine, Vinzolidine Sulfate, Viprostol, Virginiamycin, Viridofulvin, Viroxime, vitaxin, Volazocine, voriconazole, vorozole, voxergolide, Warfarin Sodium, Xamoterol, Xanomeline, Xanoxate Sodium, Xanthinol Niacinate, xemilofiban, Xenalipin, Xenbucin, Xilobam, ximoprofen, Xipamide, Xorphanol Mesylate, Xylamidine Tosylate, Xylazine Hydrochloride, Xylometazoline Hydrochloride, Xylose, yangambin, zabicipril, zacopride, zafirlukast, Zalcitabine, zaleplon, zalospirone, Zaltidine Hydrochloride, zaltoprofen, zanamivir, zankiren, zanoterone, Zantac, Zarirlukast, zatebradine, zatosetron, Zatosetron Maleate, zenarestat, Zenazocine Mesylate, Zeniplatin, Zeranol, Zidometacin, Zidovudine, zifrosilone, Zilantel, zilascorb, zileuton, Zimeldine Hydrochloride, Zinc Undecylenate, Zindotrine, Zinoconazole Hydrochloride, Zinostatin, Zinterol Hydrochloride, Zinviroxime, ziprasidone, Zobolt, Zofenopril Calcium, Zofenoprilat, Zolamine Hydrochloride, Zolazepam Hydrochloride, zoledronie acid, Zolertine Hydrochloride, zolmitriptan, zolpidem, Zomepirac Sodium, Zometapine, Zoniclezole Hydrochloride, Zonisamide, zopiclone, Zopolrestat, Zorbamyciin, Zorubicin Hydrochloride, zotepine, Zucapsaicin.

Another pharmaceutical active acceptable for use herein is lumateperone, as disclosed in U.S. Pat. Nos. 9,745,300, 9,708,322, 7,183,282, 7,071,186, 6,552,017, 8,648,077, 8,598,119, 9,751,883, 9,371,324, 9,315,504, 9,428,506, 8,993,572, 8,309,722, 6,713,471, 8,779,139, 9,168,258, RE039680E1, 9616061, 9586960, and in U.S. Patent Publication Nos. 2017114037, 2017183350, 2015072964, 2004034015, 2017189398, 2016310502, 2015080404, the aforementioned contents of which are incorporated by reference herein in their entirety.

Further examples of antidiabetic actives include but not limited to JTT-501 (PNU-182716) (Reglitazar), AR-H039242, MCC-555 (Netoglitazone), AR-H049020 Tesaglitazar), CS-011 (CI-1037), GW-409544x, KRP-297, RG-12525, BM-15.2054, CLX-0940, CLX-0921, DRF-2189, GW-1929, GW-9820, LR-90, LY-510929, NIP-221, NIP-223, JTP-20993, LY 29311 Na, FK 614, BMS 298585, R 483, TAK 559, DRF 2725 (Ragaglitazar), L-686398, L-168049, L-805645, L-054852, Demethyl asteriquinone B1 (L-783281), L-363586, KRP-297, P32/98, CRE-16336 and EML-16257.

Erectile dysfunction therapies useful herein include, but are not limited to, agents for facilitating blood flow to the penis, and for effecting autonomic nervous activities, such as increasing parasympathetic (cholinergic) and decreasing sympathetic (adrenersic) activities. Useful actives for treatment of erectile dysfunction include, for example, but are not limited to, alprostadil, tadalafil, vardenafil, apomorphine, yohimbine hydrochloride, sildenafil citrate, and any combination thereof. In an embodiment, the active is tadalafil.

Actives or medications for the treatment of headaches and/or migraines may also be used herein. Examples of specific actives include, but are not limited to, triptans, such as eletriptan, naratriptan, rizatriptan (rizatriptan benzoate), sumatriptan, and zolmitriptan. In an embodiment, the active is rizatriptan, optionally in combination with an NSAID.

In an embodiment, the active may be clobazam, diazepam, tadalafil, riluzole, buprenorphine, naloxone, or buprenorphine in combination with naloxone.

The active may be diazepam. When the active is diazepam, each individual unit dose may contain about 1 mg, about 2 mg, about 2.5 mg, about 5 mg, about 10 mg, about 15 mg or about 20 mg of diazepam. In certain embodiments, the oral film contains about 5 mg, about 10 mg, or about 15 mg of diazepam.

The active may be riluzole. When the active is riluzole, each individual unit dose may contain about 10 mg, about 20 mg, about 25 mg, about 30 mg, or about 50 mg of riluzole. In an embodiment, the oral film contains about 50 mg of riluzole.

The active may be clobazam. When the active is clobazam, each individual unit dose may contain about 1 mg, about 2 mg, about 2.5 mg, about 5 mg, about 10 mg, about 15 mg or about 20 mg of clobazam. In certain embodiments, the oral film contains about 5 mg, or about 20 mg of clobazam.

Micronized

The active used in the oral films disclosed herein may be micronized. The active may be micronized by any means known in the art.

The active may have an average particle size D90 of less than about 160 microns, less than about 120 microns, less than about 100 microns, less than about 80 microns, less than about 50 microns, less than about 20 microns, less than about 10 microns, or of about 8 microns. The active may have an average particle size D50 of less than about 30, less than about 20, less than about 10, less than about 5 microns, less than about 4, or a D50 of about 3. The active may have an average particle size D10 of less than about 10, less than about 5, less than about 3, less than about 2, or D10 of about 1. The active may have an average particle size D90 of less than about 15 microns, D50 of less than about 4 microns, and D10 of less than about 2 micron. The active may have an average particle size D90 of about 8 microns, D50 of about 3 microns, and D10 of about 1 micron.

Particle size is most commonly measured utilizing Laser Diffraction Light Scattering for particles ranging from 0.02-2000 μm/0.01-3500 μm. In this technique, particles pass through the path of the laser and diffract the light. The angle of the diffracted light is then correlated to the particle size using the differences in refractive index between the particles and the media. The output of this measurement is the Volume distribution and often expressed as $D_x$, where x is an expression of the distribution. For example, a $D_{90}$ would be reflective of the volume distribution of the analyzed particles that captures 90% of the observed diffraction; therefore 90% of the particles would fall below this size. Other descriptions of particle size are commonly used such as "Number distribution" which will correlate the number the particles that have this size, as the volume impact of larger particles can be disproportionate weighted. However, these alternative statistical descriptions of particle size based of Laser Diffraction Light Scattering are mathematical calculations based on the Volume distribution; therefore, unless specifically noted otherwise, the particle size description of $D_x$, is volume distribution.

It was known that an average particle size of less than 200 microns is preferred to obtain a smooth oral film. However, further development showed that improved film aesthetics and dissolution are possible with a finer average particle size, i.e., finely divided particulate. It was further found that dissolution testing results for lower film doses (e.g., 5 mg and 10 mg) showed that micronized active performed better than films comprising milled active (for example, having an average particle size D90 of about 100 microns).

Dissolution Profile

The PION apparatus, such as the PION Rainbow Dynamic Dissolution Monitor (RDDM®)("PION technology"), is a powerful analytical instrument that accurately and efficiently measures percent dissolved data in real time. PION technology utilizes advanced fiber optics for in situ kinetic solubility and supersaturation UV monitoring for dissolution testing to determine the rate of release of a drug substance and its dissolution over time. PION technology uses individual diode array spectrophotometers and has 6-8 acquisition channels, dip-style probes, and interchangeable pathlength tips. PION technology has a real time data display, thereby delivering fast and reproducible results for testing of actives, formulations, and drug products. These measurements are accurate, even with small volumes and complex matrices.

Fiber Optic based dissolution systems, such as PION technology, have previously been used with dosage forms other than oral films. However, because of the size and density of oral films, these systems could not properly be utilized; e.g., the films would dissolve and release the active before any measurements were even taken. To overcome this, a custom film introduction system/holder had to be designed and developed. The custom film introduction system/holder prevents the films from floating and being stirred around in the dissolution vessel. It also allows for simultaneous introduction of multiple films at the same time. This is critical for rapid data collection. Further, the sample holder, its distance from the paddle, and both distance and angle from the fiber optic probe play a significant role in consistent accurate data collection, while ensuring the flow dynamic requirements of the USP. A non-limiting exemplary configuration of an apparatus used for PION technology is shown in FIG. 1. As shown in this figure, the system is configured with multiple systems set up in parallel to run simultaneous tests on different samples. The system includes a probe, dissolution paddle and custom sample holder. There are options for placement of the custom sample holder (height and angle relative to flow). The size of the holder can also be changed to accommodate the size of the film. In addition, as readily understood by one of ordinary skill in the art, the path length of the probe may be varied. If the path length is too wide, the signal will be overloaded. If it is too narrow, the signal will be too weak.

Figure 2:
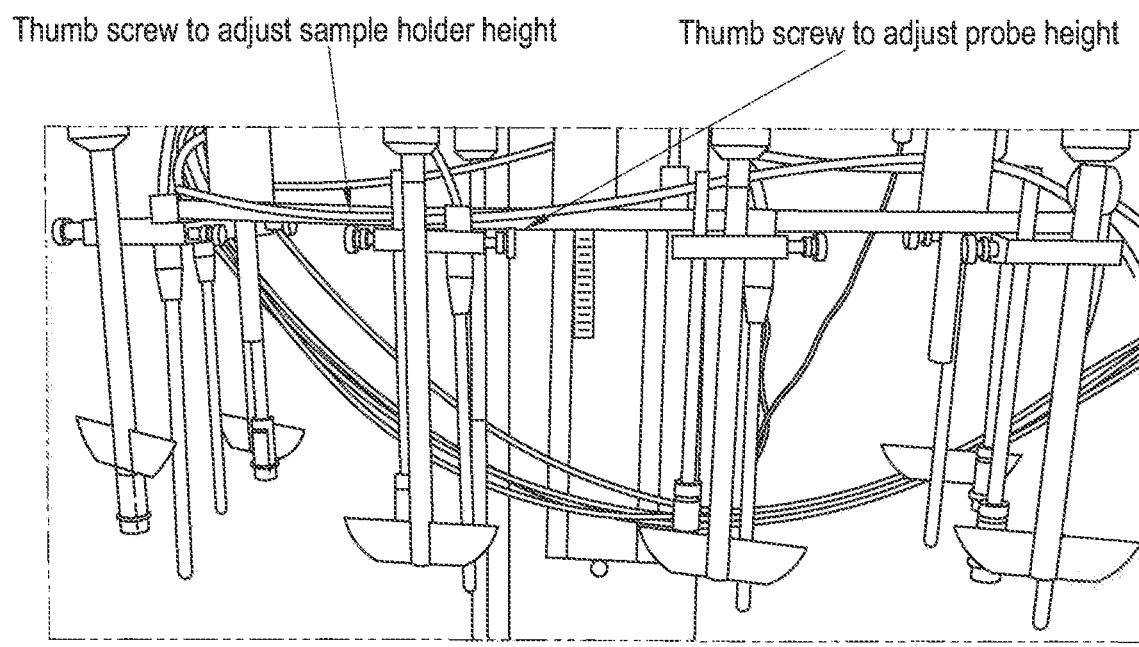

FIG. 2 is another exemplary configuration of paddles, holders, and means to adjust the heights of the probe and holder used in obtaining dissolution profiles by PION technology. With sufficient paddle agitation, the probe height is not predicted to impact results, but the orientation of the sample holder can impact disintegration of the film, and impact active dissolution rate. As shown in FIGS. 1 and 2, for example, the sample holder is placed perpendicular to the wall of the dissolution vessel to maximize exposure. The angle of the holder relative to the dissolution vessel may be changed by repositioning the holder orientation (twisting the holder from perpendicular to another desired angle). The size of the holder may be increased to accommodate larger films, but may limit the allowable angle range, e.g., if the holder is large for a larger film then it will have less freedom for adjustment. If twisted too far, the holder or film will either contact the side wall of the vessel or contact the spinning paddle-negatively impacting the test.

It was found that PION technology could be used to test dissolution of the oral films disclosed herein by customizing the sample holders, and sampling manifold. By using PION technology, there are a number of advantages, such as:
1. No offline analysis is required,
2. Availability of more sampling points,
3. Ability to evaluate multiple wavelengths,
4. Ability to evaluate rate of change (e.g., inflection point acceptance criteria),
5. Profile comparison shows potential discriminating ability between strengths and storage conditions.

It was found that the active dissolution profiles and rates of the oral films disclosed herein measured by PION technology were generally comparable to dissolution profiles and rates measured by traditional dissolution except that the curves were more precise and more accurate and because of this, inflection points are determinable. Using a fiber optic UV monitoring system, such as PION technology, more accurate and precise dissolution profiles for oral films are possible. A dissolution profile is an average collection of data points showing percent dissolution of the dosage form or active over time, from t=0 until the time past the point when 100% of the dosage form or active is dissolved. The "active dissolution profile" refers to the dissolution profile of the active after it has been released from the film. The film itself and the carriers therein have some affect on the dissolution rate of the active as the active dissolves after it has been released from the oral film dosage form.

Figure 8:
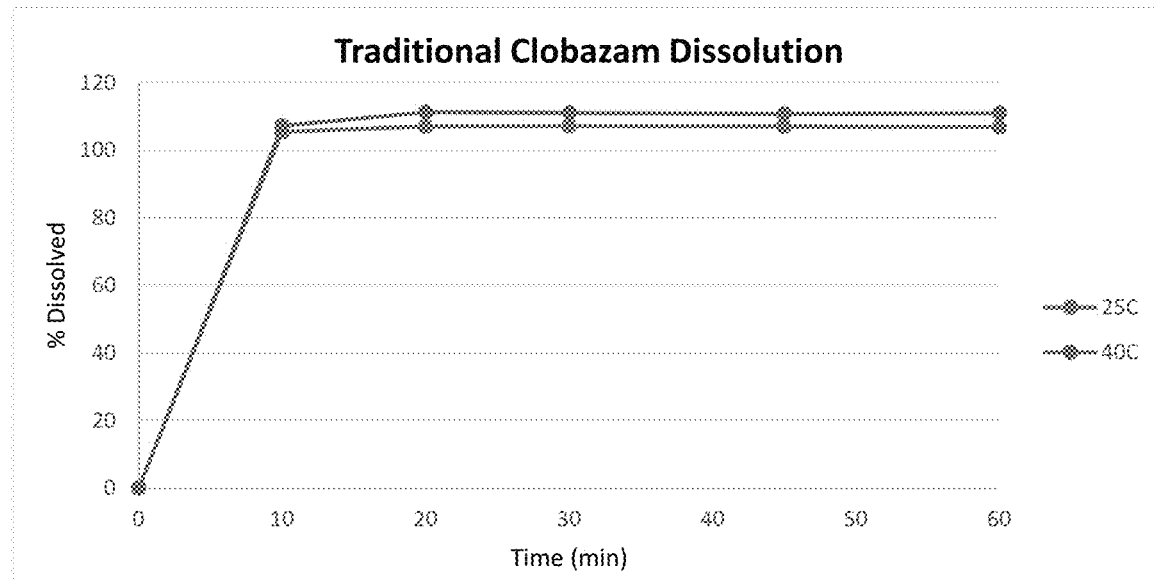
FIG. 8 is a graph showing average active dissolution profiles for oral films containing 5 mg of clobazam after storage for about 24 months and 60 RH at about 25° C. and about 40° C. measured by traditional dissolution.
Figure 9:
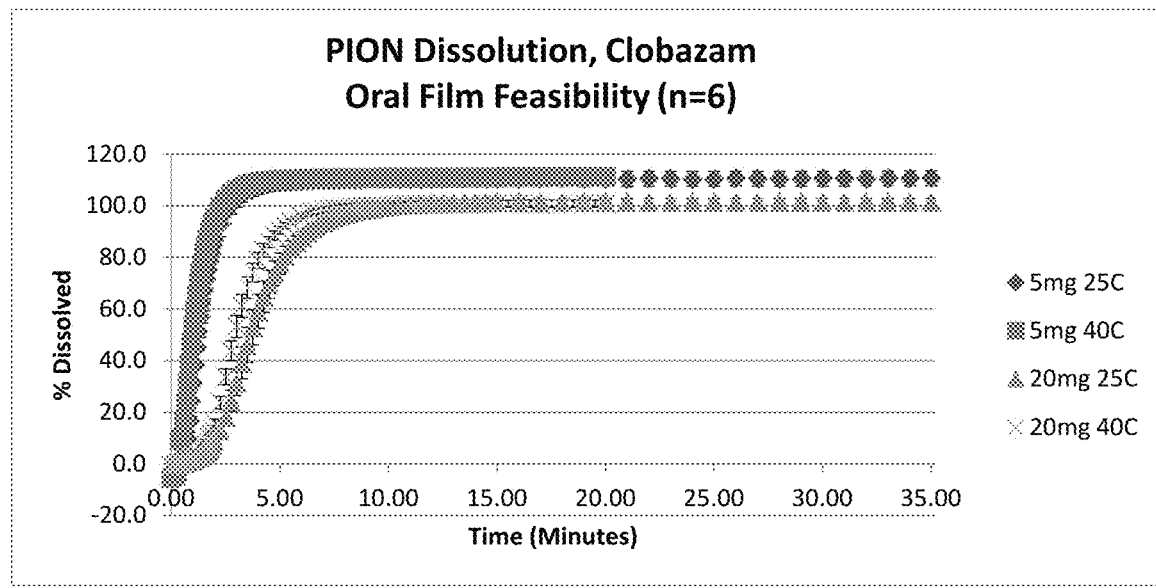
FIG. 9 is a graph of average active dissolution profiles for oral films containing 5 mg and 20 mg of clobazam after storage at about 25° C. and about 40° C. measured by PION technology.
Figure 10:
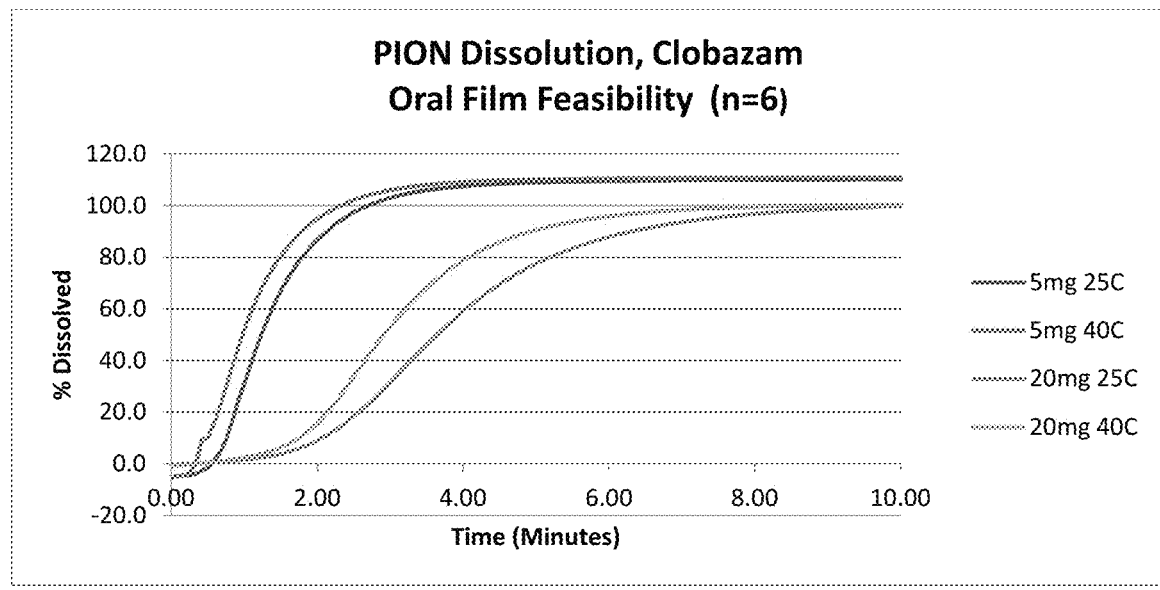
FIG. 10 is an enhanced view of the graph of FIG. 9 showing the curve of the active dissolution profile from 1 to 10 minutes for oral films containing 5 mg and 20 mg of clobazam after storage at about 25° C. and about 40° C.

For example, FIGS. 9 and 10 show active dissolution profiles and also FIGS. 13-23 show improved and more precise data and derivatives possible with PION technology. In contrast, FIG. 8 shows active dissolution profiles measured by traditional dissolution which lacks any discriminating ability at the critical early time points for fast releasing dosage forms.

Figure 19:
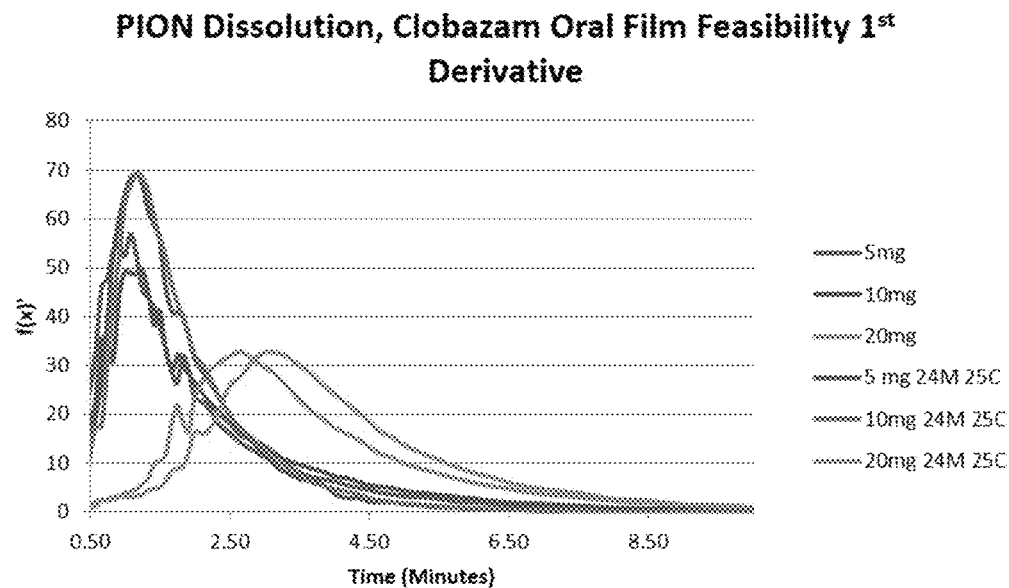
FIG. 19 is the $1^{st}$ derivative graph of the active dissolution profile of FIG. 18.
Figure 21:
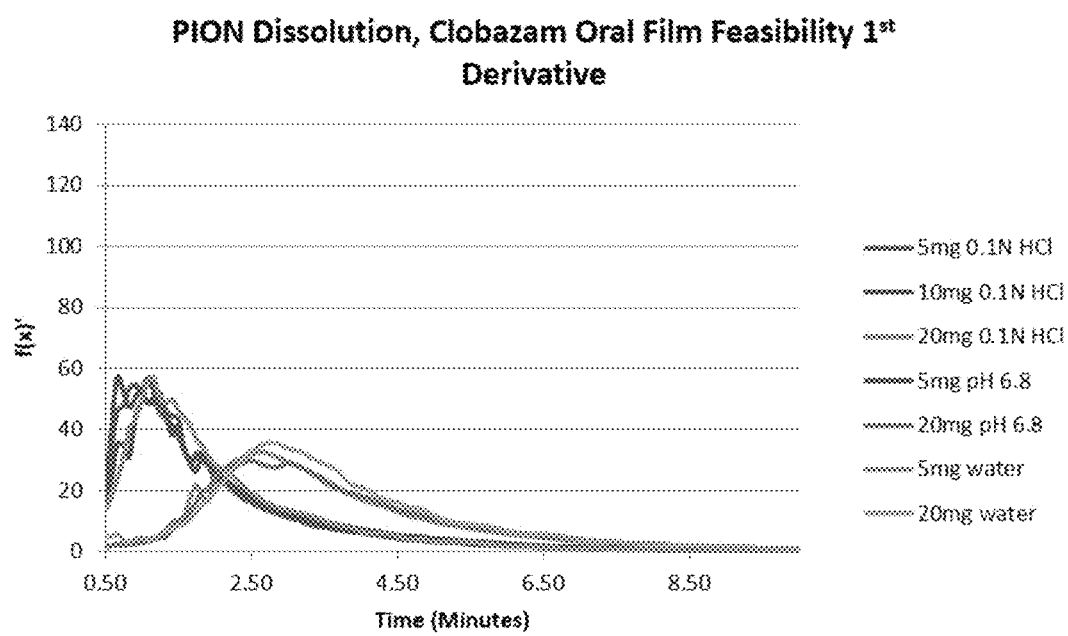
FIG. 21 is the $1^{st}$ derivative graph of the active dissolution profile of FIG. 20.
Figure 23:
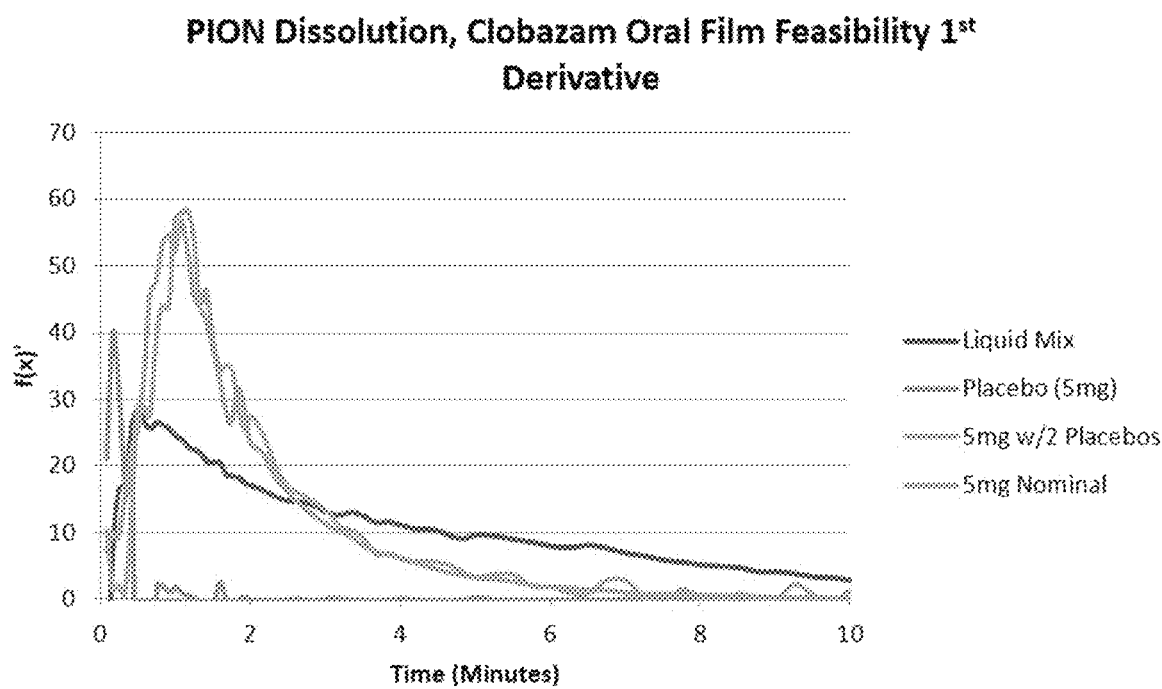
FIG. 23 is the $1^{st}$ derivative graph of the active dissolution profile of FIG. 22.

When using PION technology, the first derivative (or "1st derivative") of an oral film's active dissolution profile may be graphed, for example, as shown in FIGS. 19, 21 and 23. The first derivative graph provides insight into the rate of release of the active from the film. The intensity and width of the first derivative is proportional to the rate of release. For example, by charting these derivatives, one can learn that oral films containing 5 mg and 10 mg release faster and more fully within the first minute than a similar oral film containing 20 mg of the active, as indicated by the height and width of the first derivative curve. In such a showing, the oral film containing 20 mg of the active would have a wider curve demonstrating a slower release. For all curves, the first derivative approaches 0 as the release completes, and the concentration of drug in the vessel plateaus.

One would expect that if the active has the same particle size distribution in different film dosage forms, the active dissolution profile would be the same. However, this is not always the case. By using PION technology, discernable differences are visible between the dosage forms demonstrating that the film and the carriers affect the rate of dissolution of the active.

A second derivative (or "$2^{nd}$ derivative") graph offers a qualitative assessment of the curve. Both the $1^{st}$ and $2^{nd}$ derivative curves provide maxima, minima, and inflection points; providing the ability to determine when the curve is increasing/decreasing and the rate.

Upon placing the film in a medium, the active may have an average dissolution of more than about 2%, more than about 5%, more than about 10%, more than about 15%, more than about 20%, more than about 25%, more than about 30%, more than about 35%, more than about 40%, more than about 45%, more than about 50%, or more than about 55%, at about 2 minutes, optionally measured by PION technology. The active may have an average dissolution of more than about 2%, more than about 5%, more than about 10%, more than about 15%, more than about 20%, more than about 25%, more than about 30%, more than about 35%, more than about 40%, more than about 45%, more than about 50%, more than about 55%, more than about 60%, about 65%, or more than about 70%, at about 3 minutes, optionally measured by PION technology. The active may have an average dissolution of more than about 10%, more than about 15%, more than about 20%, more than about 25%, more than about 30%, more than about 35%, more than about 40%, more than about 45%, more than about 50%, more than about 55%, more than about 60%, about 65%, or more than about 70%, at about 5 minutes, optionally measured by PION technology. The active may have an average dissolution of more than more than about 20%, more than about 25%, more than about 30%, more than about 35%, more than about 40%, more than about 45%, more than about 50%, more than about 55%, more than about 60%, more than about 65%, more than about 70%, more than about 75%, more than about 80%, more than about 85%, or more than about 90%, at about 10 minutes, optionally measured by PION technology. The active may have an average dissolution of more than more than about 30%, more than about 35%, more than about 40%, more than about 45%, more than about 50%, more than about 55%, more than about 60%, more than about 65%, more than about 70%, more than about 75%, more than about 80%, more than about 85%, more than about 90%, more than about 95%, or more than about 98%, at about 15 minutes, optionally measured by PION technology. The active may have an average dissolution of more than about 60%, more than about 65%, more than about 70%, more than about 75%, more than about 80%, more than about 85%, more than about 90%, more than about 95%, more than about 98%, or more than about 99% at about 20 minutes, optionally measured by PION technology. Dissolution of the active, as measured herein, is after the film has been placed in a medium. Upon being placed in the medium, the film dissolves releasing the active into the medium.

Dissolution rate is the rate at which the oral film or active dissolves, which is a calculated amount of % released at a point in time. The dissolution rate is obtained by performing dissolution testing in a selected apparatus, and is measured according to certain dissolution parameters. The dissolution parameters include storage conditions, such as time, temperature, and relative humidity, and testing parameters, such things as the apparatus, rotation speed, media, media temperature, sampling time points, sample volume, sample filter, HPLC column, mobile phase, flow rate, column temperature, injection volume, detection wavelength, and run time.

"Active dissolution rate" is the rate at which the active dissolves, which is a calculated amount of % released at a point in time. In the case of an oral film dosage form, as disclosed herein, the oral film dissolves and releases the active, which then undergoes dissolution at a precise rate (i.e., the active dissolution rate). Dissolution of the active may also be expressed as % active dissolved (average) at a point in time.

Unless otherwise noted, dissolution of the active is measured under storage conditions of the oral film of about 0 months to about 36 months, more than 0 to about 36 months, about 6 to about 36 months, about 6 to about 24 months, about 9 months to about 18 months, or about 12 months, at about 20° C. to about 60° C., about 25° C. to about 40° C., or about 25° C., and up to about 75% relative humidity (RH), e.g., at about 60% RH.

The dissolution tests may be conducted under "sink" conditions, defined by USP <1092>"as the volume of medium at least three times that required in order to form a saturated solution of drug substance. When sink conditions are present, it is more likely that dissolution results will reflect the properties of the dosage form." Different media may be required for different drug products, based upon the characteristics of the active, such as solubility, and route of administration. As readily understood by one of ordinary skill in the art, in developing a dissolution method, the above factors may be considered. With that, USP <1092> also defines a range of media to evaluate: "Typical media for dissolution may include the following (not listed in order of preference): dilute hydrochloric acid, buffers (phosphate or acetate) in the physiologic pH range of 1.2 to 7.5, simulated gastric or intestinal fluid (with or without enzymes), water, and surfactants (with or without acids or buffers)." The surfactant may be, but is not limited to, polysorbate 80, sodium lauryl sulfate, and bile salts. For some drugs, incompatibility of the drug with certain buffers or salts may influence the choice of buffer. The molarity of the buffers and acids used can influence the solubilizing effect, and this factor may be evaluated. Aqueous solutions (acidic or buffer solutions) may contain a percentage of a surfactant, e.g., sodium dodecyl sulfate (SDS), polysorbate, or lauryldimethylamine oxide, to enhance the solubility of the drug.

In an embodiment, dissolution of the active is measured in dilute hydrochloric acid, a buffer (e.g., phosphate or acetate) in the physiologic pH range of 1.2 to 7.5, (including but not limited to, 0.05 molar monobasic potassium phosphate buffer of pH 6.8) simulated gastric or intestinal fluid (with or without enzymes) (e.g., 0.1N HCL), water, and surfactants (e.g., polysorbate 80, sodium lauryl sulfate, and bile salts). In another embodiment, dissolution of the active is measured in dilute hydrochloric acid, 0.05 molar monobasic potassium phosphate buffer of pH 6.8, 0.1N HCL), water, or 0.5% sodium lauryl sulfate.

For an oral film containing diazepam, upon placing the film in a medium, more than about 2% of the diazepam may be dissolved after about 3 minutes, more than about 10% of the diazepam may be dissolved after about 5 minutes, more than about 15% of the diazepam may be dissolved after about 5 minutes, or about 20% to about 25% of the diazepam may be dissolved after about 5 minutes, optionally measured by PION technology. More than about 25%, more than about 30%, or about 35% to about 40% of the diazepam may be dissolved after about 10 minutes, optionally measured by PION technology. More than about 42%, more than about 48%, or about 50% to about 55% of the diazepam may be dissolved after about 15 minutes, optionally measured by PION technology. More than about 55%, more than about 60%, or about 60% to about 70% of the diazepam may be dissolved after about 20 minutes, optionally measured by PION technology. More than about 85%, more than about 90%, or about 92% to about 98% of the diazepam may be dissolved after about 30 minutes, optionally measured by PION technology. Any combination of the above-noted dissolutions at different time points is within the scope of the invention.

For an oral film containing about 5 mg diazepam, more than about 2% of the diazepam may be dissolved after about 3 minutes, more than about 15% of the diazepam may be dissolved after about 5 minutes, or about 21% of the diazepam may be dissolved after about 5 minutes, optionally measured by PION technology. For the oral film containing about 5 mg diazepam, more than about 30%, less than about 38%, or about 36% of the diazepam may be dissolved after about 10 minutes, optionally measured by PION technology. For the film containing about 5 mg diazepam, less than about 55%, more than about 45%, or about 50% of the diazepam may be dissolved after about 15 minutes, optionally measured by PION technology. For the film containing about 5 mg diazepam, less than about 70%, more than about 60%, or about 64% of the diazepam may be dissolved after about 20 minutes, optionally measured by PION technology. Any combination of the above-noted dissolutions at different time points is within the scope of the invention.

For an oral film containing about 15 mg diazepam, more than about 2% of the diazepam may be dissolved after about 3 minutes, more than about 20% of the diazepam may be dissolved after about 5 minutes, more than about 25% of the diazepam may be dissolved after about 5 minutes, and/or about 27% of the diazepam may be dissolved after about 5 minutes, optionally measured by PION technology. For the film containing about 15 mg diazepam, more than about 35%, less than about 45%, or about 41% of the diazepam may be dissolved after about 10 minutes, optionally measured by PION technology. For the film containing about 15 mg diazepam, less than about 60%, more than about 45%, more than about 50%, or about 55% of the diazepam may be dissolved after about 15 minutes, optionally measured by PION technology. For the film containing about 15 mg diazepam, less than about 70%, more than about 60%, more than about 65%, or about 68% of the diazepam is dissolved after about 20 minutes, optionally measured by PION technology. Any combination of the above-noted dissolutions at different time points is within the scope of the invention.

For an oral film containing riluzole, more than about 2% of the riluzole may be dissolved after about 3 minutes, more than about 30% of the riluzole may be dissolved after about 5 minutes, and/or more than about 35% of the riluzole may be dissolved after about 5 minutes, optionally measured by PION technology. For the film containing riluzole, less than about 75%, less than about 73%, more than about 60%, more than about 65%, and/or more than about 68% of the riluzole may be dissolved after about 10 minutes, optionally measured by PION technology. For the film containing riluzole, less than 98%, less than about 95%, more than 75%, and/or more than about 80% of the riluzole may be dissolved after about 15 minutes, optionally measured by PION technology. Any combination of the above-noted dissolutions at different time points is within the scope of the invention.

For an oral film containing about 50 mg riluzole, more than about 2% of the riluzole may be dissolved after about 3 minutes, more than 10% of the riluzole may be dissolved after about 5 minutes, more than 20% of the riluzole may be dissolved after about 5 minutes, more than 30% of the riluzole may be dissolved after about 5 minutes, less than about 45% of the riluzole may be dissolved after about 5 minutes, or about 40% of the riluzole may be dissolved after about 5 minutes, optionally measured by PION technology. For the film containing about 50 mg riluzole, more than 30%, more than 40%, more than 50%, less than about 75%, or about 71% of the riluzole may be dissolved after about 10 minutes, optionally measured by PION technology. For the film containing about 50 mg riluzole, more than 85%, less than 93%, less than about 91%, or about 89% to about 90% of the riluzole may be dissolved after about 15 minutes, optionally measured by PION technology. Any combination of the above-noted dissolutions at different time points is within the scope of the invention.

For an oral film containing clobazam, more than about 3%, more than about 5%, more than about 10%, or more than about 15% of the clobazam may be dissolved after about 1 minute, optionally measured by PION technology. More than about 5%, more than about 10%, more than about 30%, or more than about 40% of the clobazam may be dissolved after about 1.5 minutes, optionally measured by PION technology. More than about 15%, more than about 20%, more than about 40%, or more than about 60% of the clobazam may be dissolved after about 2.5 minutes, optionally measured by PION technology. More than about 20%, more than about 30%, more than about 35%, more than about 40%, or more than about 45% of the clobazam may be dissolved after about 3 minutes, optionally measured by PION technology. More than about 55%, more than about 65%, more than about 70%, or more than about 75% of the clobazam may be dissolved after about 5 minutes, optionally measured by PION technology. More than about 85%, more than about 90%, or more than about 91% of the clobazam may be dissolved after about 6.5 minutes, optionally measured by PION technology. More than about 95%, or more than about 99% of the clobazam may be dissolved after about 10 minutes, optionally measured by PION technology. Any combination of the above-noted dissolutions at different time points is within the scope of the invention.

For an oral film containing about 5 mg clobazam, more than about 25%, more than about 30%, or of about 38% of the clobazam may be dissolved after about 1 minute, measured after storage of the film at about 25° C., optionally measured by PION technology, and more than about 45%, more than about 50%, or about 59% of the clobazam may be dissolved after about 1 minute, measured after storage of the film at about 40° C., optionally measured by PION technology. For the film containing about 5 mg clobazam, more than about 60%, or more than about 65% of the clobazam may be dissolved after about 1.5 minutes, measured after storage of the film at about 25° C., optionally measured by PION technology, and more than about 75%, or more than about 80% of the clobazam may be dissolved after about 1.5 minutes, measured after storage of the film at about 40° C., optionally measured by PION technology. For the film containing 5 mg clobazam, more than about 80%, or more than about 85% of the clobazam may be dissolved after about 2 minutes, measured after storage of the film at about 25° C., optionally measured by PION technology, and more than about 85%, or more than about 90% of the clobazam may be dissolved after about 2 minutes, measured after storage of the film about 40° C., optionally measured by PION technology. For the film containing about 5 mg clobazam, more than about 95%, or of about 97% of the clobazam may be dissolved after about 2.5 minutes, measured after storage of the film at about 25° C., optionally measured by PION technology, and more than about 95%, or more than about 100% of the clobazam may be dissolved after about 2.5 minutes, measured after storage of the film at about 40° C., optionally measured by PION technology. Any combination of the above-noted dissolutions at different time points is within the scope of the invention.

For an oral film containing about 10 mg clobazam, more than about 15%, or more than about 20% of the clobazam may be dissolved after about 1 minute, measured after storage of the film at about 25° C., optionally measured by PION technology, and more than about 35%, or more than about 40% of the clobazam may be dissolved after about 1 minute, measured after storage of the film at about 40° C., optionally measured by PION technology. For the film containing about 10 mg clobazam, more than about 50%, or more than about 55% of the clobazam may be dissolved after about 1.5 minutes, measured after storage of the film at about 25° C., optionally measured by PION technology, and more than about 65%, or more than about 70% of the clobazam may be dissolved after about 1.5 minutes, measured after storage of the film at about 40° C., optionally measured by PION technology. For the film containing about 10 mg clobazam, more than about 70%, or more than about 75% of the clobazam may be dissolved after about 2 minutes, measured after storage of the film at about 25° C., optionally measured by PION technology, and more than about 80%, or more than about 85% of the clobazam may be dissolved after about 2 minutes, measured after storage of the film at about 40° C., optionally measured by PION technology. Any combination of the above-noted dissolutions at different time points is within the scope of the invention.

For an oral film containing about 20 mg clobazam, more than about 2%, or of about 4% of the clobazam may be dissolved after about 1.5 minutes measured after storage of the film at about 25° C., optionally measured by PION technology, and more than about 5%, or about 6% of the clobazam may be dissolved after about 1.5 minutes measured after storage of the film at about 40° C., optionally measured by PION technology. For the film containing about 20 mg clobazam, more than about 10%, or more than about 15% of the clobazam may be dissolved after about 2.5 minutes measured after storage of the film at about 25° C., optionally measured by PION technology, and more than about 25%, or more than about 30% of the clobazam may be dissolved after about 2.5 minutes measured after storage of the film at about 40° C., optionally measured by PION technology. For the film containing about 20 mg clobazam, more than about 40%, or about 46% of the clobazam may be dissolved after about 3.5 minutes measured after storage of the film at about 25° C., optionally measured by PION technology, and more than about 65%, or about 68% of the clobazam may be dissolved after about 3.5 minutes measured after storage of the film at about 40° C., optionally measured by PION technology. For the film containing about 20 mg clobazam, more than about 80%, or about 83% of the clobazam may be dissolved after about 5.5 minutes measured after storage of the film at about 25° C., optionally measured by PION technology, and more than about 90%, or about 94% of the clobazam may be dissolved after about 5.5 minutes measured after storage of the film at about 40° C., optionally measured by PION technology. Any combination of the above-noted dissolutions at different time points is within the scope of the invention.

The rate of dissolution of the active may contribute to organoleptic properties of the oral film. There is a balance between the amount of active that is dispersed in the film and the amount that is dissolved in the film. If too much of the active is dissolved rather than dispersed in the film, then, upon placing the film in the oral cavity, the patient will taste the active, which often has a very unpleasant flavor. In an embodiment, less than about 10% by weight of the active is dissolved (also referred to as, solubilized) and more than about 90% is dispersed in the oral film. In other embodiments, less than about 8%, less than about 5%, less than about 2%, about 0.1% to about 10%, about 0.5% to about 5%, about 0.5% to about 2.5%, about 1.0% to about 2.0%, about 0.5%, about 0.8%, about 1.0%, about 1.2%, about 1.5%, about 1.8%, or about 2.0% by weight of the active is dissolved in the oral film.

Dissolution Profile Comparisons

For more major changes in drug products, a dissolution profile comparison performed under identical conditions for the reference product and the changed product is recommended. ("Guidance for Industry, Dissolution Testing of Immediate Release Solid Oral Dosage Forms," U.S. Department of Health and Human Services, Food and Drug Administration, Center for Drug Evaluation and Research (CDER), August 1997 (available at: http://www.fda.gov/cder/guidance.htm)). Dissolution profiles may be considered similar by virtue of (1) overall profile similarity and (2) similarity at every dissolution sample time point.

One means of conducting a dissolution profile comparison is by using a model independent method using similarity factors. A simple model independent approach uses a difference factor ($f_1$) and a similarity factor ($f_2$) to compare dissolution profiles (Moore, J. W. and H. H. Flanner, 1996, "Mathematical Comparison of Dissolution Profiles," *Pharmaceutical Technology*, 20 (6):64-74). The difference factor ($f_1$) calculates the percent (%) difference between the two curves at each time point and is a measurement of the relative error between the two curves:

$$f_1 = \{[\Sigma_{t=1}^{n}|R_t-T_t|]/[\Sigma_{t=1}^{n}R_t]\} \cdot 100$$

where n is the number of time points, $R_t$ is the dissolution value of the reference (prechange) batch at time t, and $T_t$ is the dissolution value of the test (postchange) batch at time t.

The similarity factor ($f_2$) is a logarithmic reciprocal square root transformation of the sum of squared error and is a measurement of the similarity in the percent (%) dissolution between the two curves.

$$f_2 = 50 * \log\{[1+(1/n)\Sigma_{t=1}^{n}(R_t-T_t)^2]^{-0.5} \cdot 100\}$$

A specific procedure to determine difference and similarity factors is as follows:
a. Determine the dissolution profile of two products of the test (postchange) and reference (prechange) products.
b. Using the mean dissolution values from both curves at each time interval, calculate the difference factor ($f_1$) and similarity factor ($f_2$) using the above equations.
c. The curves are considered similar thus ensuring sameness of the products, when the $f_i$ value is equal to or less than 15 (0-15) and the $f_2$ value is greater than 50 (i.e., 50-100).

With the improved precision and enhancement of PION technology, active dissolution profiles may be compared at a higher degree of accuracy and for variables that were not previously understood to provide any calculatable difference in dissolution.

Polymer

A film and/or its components may be water-soluble, water swellable, water-insoluble, or a combination of one or more of these. The term "water-soluble" may refer to substances that are at least partially dissolvable in an aqueous solvent, including but not limited to water. The term "water-soluble" may not necessarily mean that the substance is 100% dissolvable in the aqueous solvent. The term "water-insoluble" refers to substances that are not dissolvable in an aqueous solvent, including but not limited to water. A solvent can include water, or alternatively can include other solvents (preferably, polar solvents) by themselves or in combination with water.

A film can be produced by a combination of at least one polymer and a solvent, optionally including other components. The solvent may be water, a polar organic solvent including, but not limited to, ethanol, isopropanol, acetone, or any combination thereof. In some embodiments, the solvent may be a non-polar organic solvent, such as methylene chloride. The film may be prepared by utilizing a selected casting or deposition method and a controlled drying process. For example, the film may be prepared through controlled drying processes, which include application of heat and/or radiation energy to the wet film matrix to form a visco-elastic structure, thereby controlling the uniformity of content of the film. The controlled drying processes can include air alone, heat alone, or heat and air together contacting the top of the film, bottom of the film, or the substrate supporting the cast, or deposited or extruded film, or contacting more than one surface at the same time or at different times during the drying process. Some of such processes are described in more detail in U.S. Pat. Nos. 8,765,167 and 8,652,378, which are incorporated by reference herein. Alternatively, the films may be extruded as described in U.S. Patent Publication No. 2005/0037055 A1, which is incorporated by reference herein.

A polymer matrix included in the films may be water-soluble, water swellable, or a combination thereof.

The polymer matrix includes a polymer. The polymer may be a polyethylene oxide. The polymer may include cellulose, cellulose derivatives or gums. The polymer may include polyethylene oxide, cellulose, cellulose derivatives, such as cellulose ether, or a combination thereof. The polymer may be a cellulosic polymer. In certain embodiments, the cellulosic polymer can be hydroxypropylmethyl cellulose, hydroxyethyl cellulose, hydroxyethylmethyl cellulose, hydroxypropyl cellulose, methylcellulose, carboxymethyl cellulose and/or sodium carboxymethylcellulose. In certain embodiments, the polymer can include hydroxypropyl methylcellulose. In certain embodiments, the polymer can include polyethylene oxide and a cellulose ether, such as hydroxypropyl methylcellulose. In certain embodiments, the polymer can include polyethylene oxide and/or polyvinyl pyrrolidone. In certain embodiments, the polymer matrix can include polyethylene oxide and/or a polysaccharide. In certain embodiments, the polymer matrix can include polyethylene oxide, hydroxypropyl methylcellulose and/or a polysaccharide. In certain embodiments, the polymer matrix can include polyethylene oxide, a cellulosic polymer, polysaccharide and/or polyvinylpyrrolidone. In certain embodiments, the polymer matrix can include at least one polymer selected from the group of: pullulan, polyvinyl pyrrolidone, polyvinyl alcohol, sodium alginate, polyethylene glycol, xanthan gum, tragancanth gum, guar gum, acacia gum, arabic gum, polyacrylic acid, methylmethacrylate copolymer, carboxyvinyl copolymers, starch, gelatin, ethylene oxide, propylene oxide co-polymers, collagen, albumin, poly-amino acids, polyphosphazenes, polysaccharides, chitin, chitosan, and derivatives thereof. Other examples of useful water-soluble polymers include, but are not limited to, polyethylene oxide, pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, xanthan gum, tragancanth gum, guar gum, acacia gum, arabic gum, polyacrylic acid, methylmethacrylate copolymer, carboxyvinyl copolymers, starch, gelatin, polysaccharides, and combinations thereof.

As used herein the phrase "water-soluble polymer" and variants thereof refer to a polymer that is at least partially soluble in water, and desirably fully or predominantly soluble in water, or absorbs water. Polymers that absorb water are often referred to as being water-swellable polymers. The materials useful with the present invention may be water-soluble or water-swellable at room temperature and other temperatures, such as temperatures exceeding room temperature. Moreover, the materials may be water-soluble or water-swellable at pressures less than atmospheric pressure. Desirably, the water soluble polymers are water soluble or water swellable having at least 20 percent by weight water uptake. Water swellable polymers having a 25 or greater percent by weight water uptake are also useful. In some embodiments, films formed from such water-soluble polymers may be sufficiently water-soluble to be dissolvable upon contact with bodily fluids.

Other polymers useful for incorporation into the films include biodegradable polymers, copolymers, block polymers or combinations thereof. It is understood that the term "biodegradable" is intended to include materials that chemically degrade, as opposed to materials that physically break apart (i.e., bioerodable materials). The polymers incorporated in the films can also include a combination of biodegradable or bioerodable materials. Among the known useful polymers or polymer classes which meet the above criteria are: poly(glycolic acid) (PGA), poly(lactic acid) (PLA), polydioxanes, polyoxalates, poly(alpha-esters), polyanhydrides, polyacetates, polycaprolactones, poly(orthoesters), polyamino acids, polyaminocarbonates, polyurethanes, polycarbonates, polyamides, poly(alkyl cyanoacrylates), and mixtures and copolymers thereof. Additional useful polymers include, stereopolymers of L- and D-lactic acid, copolymers of bis(p-carboxyphenoxy)propane acid and sebacic acid, sebacic acid copolymers, copolymers of caprolactone, poly(lactic acid)/poly(glycolic acid)/polyethyleneglycol copolymers, copolymers of polyurethane and (poly(lactic acid), copolymers of alpha-amino acids, copolymers of alpha-amino acids and caproic acid, copolymers of alpha-benzyl glutamate and polyethylene glycol, copolymers of succinate and poly(glycols), polyphosphazene, polyhydroxy-alkanoates or mixtures thereof. Binary and ternary systems are contemplated. The polymer matrix can include one, two, three, four or more components.

Other specific polymers useful include those marketed under the Medisorb and Biodel trademarks. The Medisorb materials are marketed by the Dupont Company of Wilmington, Del. and are generically identified as a "lactide/glycolide co-polymer" containing "propanoic acid, 2-hydroxy-polymer with hydroxy-polymer with hydroxyacetic acid." Four such polymers include lactide/glycolide 100 L, believed to be 100% lactide having a melting point within the range of 338°–347° F. (170°–175° C.); lactide/glycolide 100 L, believed to be 100% glycolide having a melting point within the range of 437°–455° F. (225°–235° C.); lactide/glycolide 85/15, believed to be 85% lactide and 15% glycolide with a melting point within the range of 338°–347° F. (170°–175° C.); and lactide/glycolide 50/50, believed to be a copolymer of 50% lactide and 50% glycolide with a melting point within the range of 338°–347° F. (170°–175° C.). The Biodel materials represent a family of various polyanhydrides which differ chemically.

Although a variety of different polymers may be used, it is desired to select polymers that provide mucoadhesive properties to the film, as well as a desired dissolution and/or disintegration rate. In particular, the time period for which it is desired to maintain the film in contact with the mucosal tissue depends on the type of pharmaceutical active contained in the composition. Some pharmaceutical actives may only require a few minutes for delivery via the mucosal membrane, whereas other pharmaceutical actives may require up to several hours or even longer. Accordingly, in some embodiments, one or more water-soluble polymers, as described above, may be used to form the film. In other embodiments, however, it may be desirable to use combinations of water-soluble polymers and polymers that are water-swellable, water-insoluble and/or biodegradable. The inclusion of one or more polymers that are water-swellable, water-insoluble and/or biodegradable may provide films with slower dissolution or disintegration rates than films formed from water-soluble polymers alone. As such, the film may adhere to the mucosal membrane for longer periods of time, such as up to several hours, which may be desirable for delivery of certain pharmaceutical actives.

The polymer matrix may include a dendritic polymer which can include highly branched macromolecules with various structural architectures. The dendritic polymers can include dendrimers, dendronised polymers (dendrigrafted polymers), linear dendritic hybrids, multi-arm star polymers, or hyperbranched polymers.

The polymer matrix may include a hyperbranched polymer, which are highly branched polymers with imperfections in their structure. However they can be synthesized in a single step reaction which can be an advantage over other dendritic structures and are therefore suitable for bulk volume applications. The properties of these polymers apart from their globular structure are the abundant functional groups, intramolecular cavities, low viscosity and high solubility. Dendritic polymers have been used in several drug delivery applications. See, e.g., Dendrimers as Drug Carriers: Applications in Different Routes of Drug Administration. J Pharm Sci, VOL. 97, 2008, 123-143, which is incorporated by reference herein.

The dendritic polymers can have internal cavities which can encapsulate drugs. The steric hindrance caused by the highly dense polymer chains might prevent the crystallization of the drugs. Thus, branched polymers can provide additional advantages in formulating crystallizable drugs in a polymer matrix.

Examples of suitable dendritic polymers include but are not limited to poly(ether) based dendrons, dendrimers and hyperbranched polymers, poly(ester) based dendrons, dendrimers and hyperbranched polymers, poly(thioether) based dendrons, dendrimers and hyperbranched polymers, poly (amino acid) based dendrons dendrimers and hyperbranched polymers, poly(arylalkylene ether) based dendrons, dendrimers and hyperbranched polymers, poly(alkyleneimine) based dendrons, dendrimers and hyperbranched polymers, poly(amidoamine) based dendrons, dendrimers or hyperbranched polymers.

Other examples of hyperbranched polymers include poly (amines), polycarbonates, poly(ether ketone)s, polyurethanes, polycarbosilanes, polysiloxanes, poly(ester amines, poly(sulfone amine)s, poly(urea urethane)s and polyether polyols such as polyglycerols.

For instance, in some embodiments, the self-supporting film may include polyethylene oxide alone or in combination with a second polymer component. The second polymer may be another water-soluble polymer, a water-swellable polymer, a water-insoluble polymer, a biodegradable polymer or any combination thereof. Suitable water-soluble polymers include, without limitation, any of those provided above. In an embodiment, the water-soluble polymer may be a hydrophilic cellulosic polymer, such as hydroxypropyl cellulose and/or hydroxypropylmethyl cellulose. In another embodiment, one or more water swellable, water-insoluble and/or biodegradable polymers also may be included in polyethylene oxide-based film. Any of the water-swellable, water-insoluble or biodegradable polymers provided above may be employed. The second polymer may be employed in amounts of about 0% to about 80% by weight of the polymer matrix, more specifically about 30% to about 70% by weight, and even more specifically about 40% to about 60% by weight, including greater than about 5%, greater than about 10%, greater than about 15%, greater than about 20%, greater than about 30%, greater than about 40%, greater than about 50%, greater than about 60%, and greater than about 70%, about 70%, less than about 70%, less than about 60%, less than about 50%, less than about 40%, less than about 30%, less than about 20%, less than about 10% or less than about 5% by weight.

The polymer plays an important role in affecting the viscosity of the film. Viscosity is one property of a liquid that controls the stability of the active in an emulsion, a colloid or a suspension. Generally, the viscosity of the matrix will vary from about 400 cps to about 100,000 cps, preferably from about 800 cps to about 60,000 cps, and most preferably from about 1,000 cps to about 40,000 cps. Desirably, the viscosity of the film-forming matrix will rapidly increase upon initiation of the drying process.

The viscosity may be adjusted based on the selected active depending on the other components within the matrix. For example, if the component is not soluble within the selected solvent, a proper viscosity may be selected to prevent the component from settling which would adversely affect the uniformity of the resulting film. The viscosity may be adjusted in different ways. To increase viscosity of the film matrix, the polymer may be chosen of a higher molecular weight or crosslinkers may be added, such as salts of calcium, sodium and potassium. The viscosity may also be adjusted by adjusting the temperature or by adding a viscosity increasing component. Components that will increase the viscosity or stabilize the emulsion/suspension include higher molecular weight polymers and polysaccharides and gums, which include without limitation, alginate, carrageenan, hydroxypropyl methyl cellulose, locust bean gum, guar gum, xanthan gum, dextran, gum arabic, gellan gum and combinations thereof.

It has also been observed that certain polymers which when used alone would ordinarily require a plasticizer to achieve a flexible film, can be combined without a plasticizer and yet achieve flexible films. For example, HPMC and HPC when used in combination provide a flexible, strong film with the appropriate plasticity and elasticity for manufacturing and storage. No additional plasticizer or polyalcohol is needed for flexibility.

The polymer may be water soluble, water swellable, water insoluble, or a combination of one or more either water soluble, water swellable or water insoluble polymers. The polymer may include cellulose or a cellulose derivative. Specific examples of useful water soluble polymers include, but are not limited to, polyethylene oxide (PEO), pullulan, hydroxypropylmethyl cellulose (HPMC), hydroxyethyl cellulose, hydroxypropyl cellulose (HPC), polyvinyl pyrrolidone. carboxymethyl cellulose polyethylene glycol, xanthan gum tragancanth gum, guar gum, acacia gum, arabic gum, polyacrylic acid, methyl-methacrylate copolymer carboxyvinyl copolymers, starch, gelatin, and combinations thereof. Specific examples of useful water insoluble polymers include, but are not limited to, ethyl cellulose, hydroxypropyl ethyl cellulose cellulose acetate phthalate, hydroxypropyl methyl cellulose phthalate and combinations thereof.

Additionally, polyethylene oxide (PEO), when used alone or in combination with a hydrophilic cellulosic polymer, achieves flexible, strong films. Additional plasticizers or polyalcohols are not needed for flexibility. Non-limiting examples of suitable cellulosic polymers for combination with PEO include HPC and HPMC. PEO and HPC have essentially no gelation temperature, while HPMC has a gelation temperature of 58-64° C. (Methocel EF available from Dow Chemical Co.). Moreover, these films are sufficiently flexible even when substantially free of organic solvents, which may be removed without compromising film properties. As such, if there is no solvent present, then there is no plasticizer in the films. PEO based films also exhibit good resistance to tearing, little or no curling, and fast dissolution rates when the polymer component contains appropriate levels of PEO.

To achieve the desired film properties, the level and/or molecular weight of PEO in the polymer component may be varied. Modifying the PEO content affects properties such as tear resistance, dissolution rate, and adhesion tendencies. Thus, one method for controlling film properties is to modify the PEO content. For instance, in some embodiments rapid dissolving films are desirable. By modifying the content of the polymer component, the desired dissolution characteristics can be achieved.

In accordance with the present invention, PEO desirably ranges from about 20% to 100 by weight in the polymer component. In some embodiments, the amount of PEO desirably ranges from about 1 mg to about 200 mg. The hydrophilic cellulosic polymer ranges from about 0% to about 80 by weight, or in a ratio of up to about 4:1 with the PEO, and desirably in a ratio of about 1:1. In some embodiments, it may be desirable to vary the PEO levels to promote certain film properties. To obtain films with high tear resistance and fast dissolution rates, levels of about 50% or greater of PEO in the polymer component are desirable. To achieve adhesion prevention, i.e., preventing the film from adhering to the roof of the mouth, PEO levels of about 20% to 75% are desirable. In some embodiments, however, adhesion to the roof of the mouth may be desired, such as for administration to animals or children. In such cases, higher levels of PEO may be employed. More specifically, structural integrity and dissolution of the film can be controlled such that the film can adhere to mucosa and be readily removed, or adhere more firmly and be difficult to remove, depending on the intended use.

The molecular weight of the PEO may also be varied. High molecular weight PEO, such as about 4 million, may be desired to increase mucoadhesivity of the film. More desirably, the molecular weight may range from about 100,000 to 900,000, more desirably from about 100,000 to 600,000, and most desirably from about 100,000 to 300,000. In some embodiments, it may be desirable to combine high molecular weight (600,000 to 900,000) with low molecular weight (100,000 to 300,000) PEOs in the polymer component. For instance, certain film properties, such as fast dissolution rates and high tear resistance, may be attained by combining small amounts of high molecular weight PEOs with larger amounts of lower molecular weight PEOs. Desirably, such compositions contain about 60% or greater levels of the lower molecular weight PEO in the PEO-blend polymer component.

To balance the properties of adhesion prevention, fast dissolution rate, and good tear resistance, desirable film compositions may include about 50% to 75% low molecular weight PEO, optionally combined with a small amount of a higher molecular weight PEO, with the remainder of the polymer component containing a hydrophilic cellulosic polymer (HPC or HPMC).

Additive

An additive may be added the films disclosed herein. A variety of additives that can be incorporated into the inventive films may provide a variety of different functions. Examples of classes of additives include excipients, lubricants, buffering agents, stabilizers, blowing agents, pigments, coloring agents, fillers, bulking agents, sweetening agents, flavoring agents, fragrances, release modifiers, adjuvants, plasticizers, flow accelerators, mold release agents, polyols, granulating agents, diluents, binders, buffers, absorbents, glidants, adhesives, anti-adherents, acidulants, softeners, resins, demulcents, solvents, surfactants, emulsifiers, elastomers and mixtures thereof. These additives may be added prior to or along with the active(s). The amount of additives in the film can range up to about 80%, about 0.005% to about 50%, about 1% to about 20%, or about 3% to about 20% based on the weight of the film composition (which is the totaled weight of all components therein) including greater than about 1%, greater than about 5%, greater than about 10%, greater than about 20%, greater than about 30%, greater than about 40%, greater than about 50%, greater than about 60%, less than about 80%, less than about 70%, less than about 60%, less than about 50%, less than about 40%, less than about 30%, less than about 20%, less than about 10%, less than about 5%, about 3%, or less than about 1%.

The additive may be selected from the group consisting of a sweetener, a flavor, a flavor enhancer, a filler, a plasticizer, a coloring agent, such as a dye or a pigment, a permeation enhancer, a buffer, a preservative, silicon dioxide, an anti-tacking agent, and any combination thereof.

Flavors may be chosen from natural and synthetic flavoring liquids. An illustrative list of such agents includes volatile oils, synthetic flavor oils, flavoring aromatics, oils, liquids, oleoresins or extracts derived from plants, leaves, flowers, fruits, stems and combinations thereof. A non-limiting representative list of examples includes mint oils, cocoa, and citrus oils such as lemon, orange, grape, lime and grapefruit, and fruit essences including apple, pear, peach, grape, strawberry, raspberry, lemon, lime, orange, cherry, plum, pineapple, apricot or other fruit flavors.

Useful flavors or flavoring agents include natural and artificial flavors. These flavorings may be chosen from synthetic flavor oils and flavoring aromatics, and/or oils, oleo resins and extracts derived from plants, leaves, flowers, fruits and so forth, and combinations thereof. Non-limiting flavor oils include: spearmint oil, cinnamon oil, peppermint oil, clove oil, bay oil, thyme oil, cedar leaf oil, oil of nutmeg, oil of sage, and oil of bitter almonds. Also useful are artificial, natural or synthetic fruit flavors such as vanilla, chocolate, coffee, cocoa and citrus oil, including lemon, orange, grape, lime and grapefruit, and fruit essences including apple, pear, peach, strawberry, raspberry, cherry, plum, pineapple, apricot and the like. These flavorings can be used individually or in combination. Commonly used flavors include mints such as peppermint, artificial vanilla, cinnamon derivatives, and various fruit flavors, whether employed individually or in combination. Flavorings such as aldehydes and esters including cinnamylacetate, cinnamaldehyde, citral, diethylacetal, dihydrocarvyl acetate, eugenyl formate, p-methylanisole, and the like may also be used. Further examples of aldehyde flavorings include, but are not limited to acetaldehyde (apple); benzaldehyde (cherry, almond); cinnamicaldehyde (cinnamon); citral, i.e., alpha citral (lemon, lime); neral, i.e. beta citral (lemon, lime); decanal (orange, lemon); ethyl vanillin (vanilla, cream); heliotropine, i.e., piperonal (vanilla, cream); vanillin (vanilla, cream); alpha-amyl cinnamaldehyde (spicy fruity flavors); butyraldehyde (butter, cheese); valeraldehyde (butter, cheese); citronellal (modifies, many types); decanal (citrus fruits); aldehyde C-8 (citrus fruits); aldehyde C-9 (citrus fruits); aldehyde C-12 (citrus fruits); 2-ethyl butyraldehyde (berry fruits); hexenal, i.e. trans-2 (berry fruits); tolyl aldehyde (cherry, almond); veratraldehyde (vanilla); 12,6-dimethyl-5-heptenal, i.e. melonal (melon); 2 dimethyloctanal (greenfruit); and 2-dodecenal (citrus, mandarin); cherry; grape; mixtures thereof; and the like.

Other useful flavorings include aldehydes and esters such as benzaldehyde (cherry, almond), citral i.e., alphacitral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanol (green fruit), and 2-dodecenal (citrus, mandarin), combinations thereof and the like.

The amount of flavoring employed is normally a matter of preference, subject to such factors as flavor type, individual flavor, and strength desired. The amount may be varied in order to obtain the result desired in the final product. Such variations are within the capabilities of those skilled in the art without the need for undue experimentation. In general, amounts of about 0.1 to about 30 wt % are useful with the practice of the present invention.

In an embodiment, the film includes berry flavoring. The berry flavoring may be raspberry, strawberry, blueberry, boysenberry, blackberry, or a combination thereof. In another embodiment, the film includes raspberry flavoring. The berry, raspberry, strawberry, blueberry, boysenberry, or blackberry flavoring may be natural or artificial and purchased and/or made by any means known in the art. For example, raspberry favoring, including aroma, may be achieved by incorporating the mix of volatile compounds disclosed in "Volatile Compounds of Raspberry Fruit: From Analytical Methods to Biological Role and Sensory Impact," by E. Aprea et al., Molecules 2015, 20, 2445-2474, which is incorporated by reference herein in its entirety. When used, the berry flavoring may be present in about 0.1% to about 15% by weight of the composition. In certain embodiments thereof, the berry flavoring is present in about 0.5% to about 10%, about 1% to about 8%, about 2% to about 7%, about 3%, about 4%, about 5%, about 6%, or about 7% by weight of the composition.

Suitable sweeteners include both natural and artificial sweeteners. Non-limiting examples of suitable sweeteners include, e.g.: water-soluble sweetening agents such as monosaccharides, disaccharides and polysaccharides such as xylose, ribose, glucose (dextrose), mannose, galactose, fructose (levulose), sucrose (sugar), high fructose corn syrup, maltose, invert sugar (a mixture of fructose and glucose derived from sucrose), partially hydrolyzed starch, corn syrup solids, and dihydrochalcones; water-soluble artificial sweeteners such as the soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin and the like; dipeptide based sweeteners, such as L-aspartic acid derived sweeteners, such as L-aspartyl-L-phenylalanine methyl ester (aspartame), L-alpha-aspartyl-N-(2,2,4,4-tetramethyl-3-thietanyl)-D-alaninamide hydrate, methyl esters of L-aspartyl-L-phenylglycerin and L-aspartyl-L-2,5, dihydrophenylglycine, L-aspartyl-2,5-dihydro-L-phenylalanine, L-aspartyl-L-(1-cyclohexyen)-alanine, and the like; water-soluble sweeteners derived from naturally occurring water-soluble sweeteners, such as a chlorinated derivatives of ordinary sugar (sucrose), known, for example, as sucralose; and protein based sweeteners such as thaurnatoccous danielli (Thaurnatin I and II). Naturally occurring high intensity sweeteners, such as Lo Han Kuo, *stevia*, steviosides, monellin, and glycyrrhizin, may also be used.

In general, an effective amount of sweetener is utilized to provide the level of sweetness desired for a particular composition, and this amount will vary with the sweetener selected. This amount will normally be 0.01% to about 10% by weight of the composition. These amounts may be used to achieve a desired level of sweetness independent from the flavor level achieved from any optional flavor oils used. In certain embodiments, the sweetener is present in about 0.5% to about 5%, about 1% to about 5%, about 1.5% to about 4%, about 1.5%, about 2%, about 2.5%, about 3%, about 3.5%, about 4%, or about 5% by weight of the composition.

The sweetener may be selected from the group consisting of: sucralose, *stevia*, acesulfame potassium, saccharin, fructose, aspartame, and any combination thereof, and may be present in about 0.5% to about 5%, about 1% to about 5%, about 1.5% to about 4%, about 1.5%, about 2%, about 2.5%, about 3%, about 3.5%, about 4%, or about 5% by weight of the composition. In an embodiment, about 3% to about 4%, about 3%, or about 3.5% by weight of the composition of sucralose, saccharin, aspartame, and any combination thereof is present in the film.

Color additives useful in this invention include food, drug and cosmetic colors (FD&C), drug and cosmetic colors (D&C), or external drug and cosmetic colors (Ext. D&C). These colors are dyes, their corresponding lakes, and certain natural and derived colorants. Lakes are dyes absorbed on aluminum hydroxide.

Other examples of coloring agents include known azo dyes, organic or inorganic pigments, or coloring agents of natural origin. Inorganic pigments are preferred, such as the oxides or iron or titanium, these oxides, being added in concentrations ranging from about 0.001 to about 10%, and preferably about 0.5 to about 3%, based on the weight of all the components. The films may be any color, including but not limited to, white, clear, blue, green, red, pink, purple, orange, or yellow. In an embodiment, the film is clear and translucent.

The film further desirably contains a buffer so as to control the pH. Any desired level of buffer tray be incorporated into the polymer matrix so as to provide the desired pH level encountered as the pharmaceutical active is released from the film. The buffer is preferably provided in an amount sufficient to control the release from the film and/or the absorption into the body of the active. The buffer may include sodium citrate, citric acid, bitartrate salt, or any combination thereof.

In certain embodiments, the film may include plasticizers, which can include polyalkylene oxides, such as polyethylene glycols, polypropylene glycols, polyethylene-propylene glycols, organic plasticizers with low molecular weights, such as glycerol, glycerol monoacetate, diacetate or triacetate, triacetin, polysorbate, cetyl alcohol, propylene glycol, sugar alcohols sorbitol, sodium diethylsulfosuccinate, triethyl citrate, tributyl citrate, phytoextracts, fatty acid esters, fatty acids, oils and the like. Plasticizers may be added in concentrations ranging from about 0.1% to about 40%, or about 0.5% to about 20% based on the weight of the film composition, including greater than about 0.5%, greater than about 1%, greater than about 1.5%, greater than about 2%, greater than about 4%, greater than about 5%, greater than about 10%, greater than about 15%, about 20%, greater than about 20%, less than about 20%, less than about 15%, less than about 10%, less than about 5%, less than about 4%, less than about 2%, less than about 1%, and less than about 0.5%. There may further be added compounds to improve the texture properties of the film material such as animal or vegetable fats, desirably in their hydrogenated form, especially those which are solid at room temperature. These fats desirably have a melting point of 50° C. or higher. Preferred are tri-glycerides with $C_{12}$-, $C_{14}$-, $C_{16}$-, $C_{18}$-, $C_{20}$- and $C_{22}$-fatty acids. These fats can be added alone without adding extenders or plasticizers and can be advantageously added alone or together with mono- and/or di-glycerides or phosphatides, especially lecithin. The mono- and di-glycerides are desirably derived from the types of fats described above, i.e. with $C_{12}$-, $C_{14}$-, $C_{16}$-, $C_{18}$-, $C_{20}$- and $C_{22}$-fatty acids. The total amounts used of the fats, mono-, di-glycerides and/or lecithins are up to about 5% or within the range of about 0.5% to about 2% based on the weight of the film composition.

A variety of other components and fillers may also be added to the films disclosed herein. These may include, without limitation, surfactants; other anti-foaming agents; such as simethicone, which promote a smoother film surface by releasing oxygen from the film; thermo-setting gels such as pectin, carageenan, and gelatin, which help in maintaining the dispersion of components; and inclusion compounds, such as cyclodextrins and caged molecules, which improve the solubility and/or stability of certain active components.

Further additives may be inorganic fillers, such as the oxides of magnesium aluminum, silicon, titanium, etc. desirably in a concentration range of about 0.02% to about 3% by weight and desirably about 0.02% to about 1% based on the weight of the film composition.

It may be useful to add silicon dioxide, calcium silicate, or titanium dioxide in a concentration of about 0.02% to about 1% by weight of the total composition. These compounds act as texturizing agents.

These additives are to be used in amounts sufficient to achieve their intended purpose. Generally, the combination of certain of these additives will alter the overall release profile of the active ingredient and can be used to modify, i.e., impede or accelerate the release.

An anti-tacking agent may be incorporated into the oral films of the disclosure. The anti-tacking agent may be selected from the group consisting of lubricants, antiadherants, glidants and combinations thereof. Anti-tacking agents assist in the flow characteristics of the material, for example, by reducing sticking to the die in extrusion processes and reducing sticking to the roof of the mouth during administration of the dosage form. During consumption of films, particles tend to adhere to the roof of the mouth. This is undesirable for films containing bitter drugs, such as, for example, dextromethorphan, because the adhered particles elude drug, which increases the amount of bitterness detected by the user. Addition of an anti-tacking agent to the films reduces adherence to the roof of the mouth, thereby effectively reducing the bitterness that may be detected by a user during consumption.

Anti-taking agents also may impart reduced film-to-film coefficient of friction, thereby reducing the problem of film dosage units, i.e., strips, adhering to one another. More specifically, in many types of film packaging, strips are stacked against one another. The incorporation of anti-tacking agents may permit the individual strips to slide smoothly against one another as each unit is removed from the packaging.

Examples of suitable lubricants for use as an anti-tacking agent include, but are not limited to: stearates, such as magnesium stearate, calcium stearate, and sodium stearate; stearic acid; vegetable oil (commercially available as sterotex); talc; waxes; a blend of magnesium stearate and sodium lauryl sulfate (commercially available as stearowet); boric acid; sodium benzoate; sodium acetate; sodium chloride; DL-Leucine; polyethylene glycol having a molecular weight of 4000 (commercially available as Carbowax 4000); polyethylene glycol having a molecular weight of 6000 (commercially available as Carbowax 6000); sodium oleate; sodium lauryl sulfate; magnesium lauryl sulfate; and combinations thereof.

Examples of suitable antiadherants include, but are not limited to: talc; cornstarch; synthetic amorphous silicon dioxide, crystalline-free (commercially available as Cab-O—Sil; syloid); DL-Leucine; sodium lauryl sulfate; metallic stearates; and combinations thereof. Examples of suitable glidants include, but are not limited to: talc; cornstarch;

synthetic amorphous silicon dioxide, crystalline-free (commercially available as Cab-O-Sil); syloid; aerosol; and combinations thereof.

Vitamin E is another suitable anti-tacking agent for use in some embodiments of the present invention. Vitamin E may serve as both an anti-tacking agent and an active component in the film. Desirably, Vitamin E TPGS (d-alpha tocopheryl polyethylene glycol 1000 succinate) is employed. Vitamin E TPGS is a water-soluble form of Vitamin E derived from natural sources. As compared to other forms, Vitamin E TPGS is easily absorbed. Further, Vitamin E TPGS imparts practically no taste to film. Vitamin E TPGS may be employed in solution, such as, for example 10% or 20% solution with water. Vitamin E TPGS is particularly useful in reducing the stickiness of the films and the tendency to adhere to the roof of the user's mouth. Vitamin E may be present in amounts of about 0.01% to about 20% by weight of the composition.

When present, the anti-tacking agent may be included in about 0.01% to about 20% by weight of the film composition. More specifically, anti-tacking agents may be present in amounts of about 0.01% to about 10% by weight of the film composition, and even more specifically, about 0.25% to about 5% by weight of the film composition.

Combinations of anti-tacking agents also may be employed. For instance, a combination of a stearate, such as magnesium stearate, and silica may be used. SIPERNAT ABOUT 500LS, which is a silica product having a 4.5 μm mean average particle size, is suitable for use herein (commercially available from Degussa). Combinations of magnesium stearate and silica may provide improved glidant properties, i.e., assist film strips in sliding smoothly against one another in packaging. Accordingly, magnesium stearate may be present in about 0.1% to about 2.5% by weight of the film composition and silica may be present in about 0.1% to about 1.5% by weight of the film composition. Such combination of anti-tacking agents may be useful in a variety of films containing different flavors and/or actives.

Anti-tacking agents may be included in the film composition itself. For example, single or multi-layer films including anti-tacking agents may be formed. Multi-layer films, for example, may include two, three or more layers of film substantially in contact with one another. The film layers may be laminated to one another. Anti-tacking agents may be present in one or more of the layers of the multi-layer film. For example, some embodiments may include a bi-layer film in which anti-tacking agents are present in one of the two film layers. Some embodiments may include a three-layer film in which anti-tacking agents are present in each of the outer layers but not in the inner, or middle, layer of the three-layer film. In accordance therewith, a variety of different combinations of layers may be formed.

Alternatively, anti-tacking agents may be included in a composition that is used to coat the external surfaces of the film. For instance, anti-tacking agents may be applied to the film in the form of a wet or dry coating, such as, for example, a sugared or sugar-free coating. The film may be coated with the anti-tacking agents in any conventional manner, such as, but not limited to, dip coating, spray coating, dusting, or fluidized bed. One or more film surfaces may be coated. In some embodiments, the anti-tacking coating may be applied to a substrate, such as a backing for the film, rather than directly to the film itself. When the film is removed from the backing, the anti-tacking coating may adhere to the film.

Some embodiments of the may include fats and/or waxes as anti-tacking agents.

Any other optional components described in commonly assigned U.S. Pat. Nos. 7,425,292 and 8,765,167, referred to above, also may be included in the films described herein.

Permeation Enhancer

The film disclosed herein may a permeation enhancer. An active may be combined, with a permeation active enhancer in a single layer of a film, each contained in separate layers, or can each be otherwise contained in discrete regions of the same dosage form. In certain embodiments, the active contained in the polymer matrix can be dispersed in the matrix. In certain embodiments, the permeation enhancer being contained in the polymer matrix can be dispersed in the matrix.

Any permeation enhancer known for use in the art may be incorporated into the films of the present disclosure. The term "permeation enhancer" is interchangeable with absorption enhancer and penetration enhancer. When delivered to the mouth via a film, a permeation enhancer is a component that can improve the permeability of the pharmaceutical active through the mucosa and into the blood stream of the subject.

The permeation enhancer may a nonionic alkyl glycoside having a hydrophobic alkyl group joined by a linkage to a hydrophilic saccharide. The permeation enhancer may be selected from the group consisting of a maltoside or maltoside derivative, a sucroside or sucroside derivative, and an essential oil or a component of an essential oil. The permeation enhancer may be selected from the group consisting of alkyl thiomaltoside, maltoside, maltotrioside, maltopyranoside, dodecyl maltoside, tridecyl maltoside, tetradecyl maltoside, tetradecyl-β-D-maltoside, dodecyl-β-D-maltoside, tridecyl-β-D-maltoside, sucroside, sucrose mono-dodecanoate, sucrose mono-tridecanoate, sucrose mono-tetradecanoate and combinations thereof.

The permeation enhancer can improve absorption rate and amount of the pharmaceutical active by more than 5%, more than 10%, more than 20%, more than 30%, more than 40%, more than 50%. more than 60%, more than 70%, more than 80%, more than 90%, more than 100%, more than 150%, about 200% or more, or less than 200%, less than 150%, less than 100%, less than 90%, less than 80%, less than 70%, less than 60%, less than 50%, less than 40%, less than 30%, less than 20%, less than 10%, or less than 5%, or a combination of these ranges, depending on the other components in the composition.

In certain embodiments, the film comprises a pharmaceutically acceptable nontoxic, nonionic alkyl glycoside having a hydrophobic alkyl group joined by a linkage to a hydrophilic saccharide in combination with a mucosal delivery-enhancing agent selected from: (a) an aggregation inhibitory agent; (b) a charge-modifying agent; (c) a pH control agent; (d) a degradative enzyme inhibitory agent; (e) a mucolytic or mucus clearing agent; (f) a ciliostatic agent; (g) a membrane penetration-enhancing agent selected from: (i) a surfactant; (ii) a bile salt; (ii) a phospholipid additive, mixed micelle, liposome, or carrier; (iii) an alcohol; (iv) an enamine; (v) an NO donor compound; (vi) a long chain amphipathic molecule; (vii) a small hydrophobic penetration enhancer; (viii) sodium or a salicylic acid derivative; (ix) a glycerol ester of acetoacetic acid; (x) a cyclodextrin or beta-cyclodextrin derivative; (xi) a medium-chain fatty acid; (xii) a chelating agent; (xiii) an amino acid or salt thereof; (xiv) an N-acetylamino acid or salt thereof; (xv) an enzyme degradative to a selected membrane component; (ix) an inhibitor of fatty acid synthesis; (x) an inhibitor of cholesterol synthesis; and (xi) any combination of the membrane penetration enhancing agents recited in (i)-(x); (h) a modulatory agent of epithelial junction physiology; (i) a vasodilator agent; (j) a selective transport-enhancing agent; and (k) a stabilizing delivery vehicle, carrier, mucoadhesive, support or complex-forming species with which the compound is effectively combined, associated, contained, encapsulated or bound resulting in stabilization of the compound for enhanced transmucosal delivery, wherein the formulation of the compound with the transmucosal delivery-enhancing agents provides for increased bioavailability of the compound in blood plasma of a subject. Penetration enhancers have been described in J. Nicolazzo, et al., J. of Controlled Disease, 105 (2005) 1-15, which is incorporated by reference herein.

Surfactants and bile salts have been shown to enhance the permeability of various compounds across the buccal mucosa, both in vitro and in vivo. The data obtained from these studies strongly suggest that the enhancement in permeability is due to an effect of the surfactants on the mucosal intercellular lipids.

Fatty acids have been shown to enhance the permeation of a number of drugs through the skin, and this has been shown by differential scanning calorimetry and Fourier transform infrared spectroscopy to be related to an increase in the fluidity of intercellular lipids.

Additionally, pretreatment with ethanol has been shown to enhance the permeability of tritiated water and albumin across ventral tongue mucosa, and to enhance caffeine permeability across porcine buccal mucosa. There are also several reports of the enhancing effect of Azone® on the permeability of compounds through oral mucosa. Further, chitosan, a biocompatible and biodegradable polymer, has been shown to enhance drug delivery through various tissues, as including the intestine and nasal mucosa.

It has been shown that buccal penetration can be improved by using various classes of transmucosal and transdermal penetration enhancers such as bile salts, surfactants, fatty acids and their derivatives, chelators, cyclodextrins and chitosan. Among these chemicals used for the drug permeation enhancement, bile salts are the most common.

In vitro studies on enhancing effect of bile salts on the buccal permeation of compounds is discussed in Sevda Senel, Drug permeation enhancement via buccal route: possibilities and limitations, Journal of Controlled Release 72 (2001) 133-144, which is incorporated by reference herein. That article also discusses recent studies on the effects of buccal epithelial permeability of dihydroxy bile salts, sodium glycodeoxycholate (SGDC) and sodium taurodeoxycholate (TDC) and tri-hydroxy bile salts, sodium glycocholate (GC) and sodium taurocholate (TC) at about 100 mM concentration including permeability changes correlated with the histological effects. Fluorescein isothiocyanate (FITC), morphine sulfate were each used as the model compound.

Chitosan has also been shown to promote absorption of small polar molecules and peptide/protein drugs through nasal mucosa in animal models and human volunteers. Other studies have shown an enhancing effect on penetration of compounds across the intestinal mucosa and cultured Caco-2 cells.

The permeation enhancer can be a phytoextract. A phytoextract can be an essential oil or composition including essential oils extracted by distillation of the plant material. In certain circumstances, the phytoextract can include synthetic analogues of the compounds extracted from the plant material (i.e., compounds made by organic synthesis). The phytoextract can include a phenylpropanoid, for example, phenyl alanine, eugenol, eugenol acetate, a cinnamic acid, a cinnamic acid ester, a cinnamic aldehyde, a hydrocinnamic acid, chavicol, or safrole, or a combination thereof. The phytoextract can be an essential oil extract of a clove plant, for example, from the leaf, stem or flower bud of a clove plant. The clove plant can be Syzygium aromaticum. The phytoextract can include about 20 to about 95% eugenol, including about 40 to about 95% eugenol, including about 60 to about 95% eugenol, and for example, about 80-95% eugenol. The extract can also include about 5% to about 15% eugenol acetate. The extract can also include caryophyllene. The extract can also include up to about 2.1% α-humulen. Other volatile compounds included in lower concentrations in clove essential oil can be β-pinene, limonene, farnesol, benzaldehyde, 2-heptanone or ethyl hexanoate. Other permeation enhancers may be added to the composition to improve absorption of the drug. Suitable permeation enhancers include natural or synthetic bile salts such as sodium fusidate; glycocholate or deoxycholate and their salts; fatty acids and derivatives such as sodium laurate, oleic acid, oleyl alcohol, monoolein, or palmitoylcarnitine; chelators such as disodium EDTA, sodium citrate and sodium laurylsulfate, atone, sodium cholate, sodium 5-methoxysalicylate, sorbitan laurate, glyceryl monolaurate, octoxynonyl-9, laureth-9, polysorbates, sterols, or glycerides, such as caprylocaproyl polyoxylglycerides, e.g., Labrasol. The permeation enhancer can include phytoextract derivatives and/or monolignols. The permeation enhancer can also be a fungal extract.

Some natural products of plant origin have been known to have a vasodilatory effect. For review, see McNeill J. R. and Jurgens, T. M., Can. J. Physiol. Pharmacol. 84:803-821 (2006), which is incorporated by reference herein. Specifically, vasorelaxant effects of eugenol have been reported in a number of animal studies. See, e.g., Lahlou, S., et at., J. Cardiovasc. Pharmacol. 43:250-57 (2004), Damiani, C. E. N., et al., Vascular Pharmacol. 40:59-66 (2003), Nishijima, H., et al., Japanese J. Pharmacol. 79:327-334 (1998), and Hume W. R., J. Dent Res. 62(9):1013-15 (1983), each of which is incorporated by reference herein. Calcium channel blockade was suggested to be responsible for vascular relaxation induced by a plant essential oil, or its main constituent, eugenol. See, Interaminense L. R. L. et al., Fundamental & Clin. Pharmacol. 21: 497-506 (2007), which is incorporated by reference herein.

Fatty acids can be used as inactive ingredients in drug preparations or drug vehicles. Fatty acids can also be used as formulation ingredients due to their certain functional effects and their biocompatible nature. Fatty acid, both free and as part of complex lipids, are major metabolic fuel (storage and transport energy), essential components of all membranes and gene regulators. For review, see Rustan A. C. and Drevon, C. A., Fatty Acids: Structures and Properties, Encyclopedia of Life Sciences (2005), which is incorporated by reference herein. There are two families of essential fatty acids that are metabolized in the human body: Ω-3 and Ω-6 polyunsaturated fatty acids (PUFAs). If the first double bond is found between the third and the fourth carbon atom from the Ω carbon, they are called Ω-3 fatty acids. If the first double bond is between the sixth and seventh carbon atom, they are called Ω-6 fatty acids. PUFAs are further metabolized in the body by the addition of carbon atoms and by desaturation (extraction of hydrogen). Linoleic acid, which is a Ω-6 fatty acid, is metabolized to γ-linolenic acid, dihomo-γ-linolinic acid, arachidonic acid, adrenic acid, tetracosatetraenoic acid, tetracosapentaenoic acid and docosapentaenoic acid. α-linolenic acid, which is Ω-3 fatty acid is metabolized to octadecatetraenoic acid, eicosatetraenoic acid, eicosapentaenoic acid (EPA), docosapentaenoic acid, tetracosapentaenoic acid, tetracosahexaenoic acid and docosahexaenoic acid (DHA).

It has been reported that fatty acids, such as palmitic acid, oleic acid, linoleic acid and eicosapentaenoic acid, induced relaxation and hyperpolarization of porcine coronary artery smooth muscle cells via a mechanism involving activation of the Na.sup.+K.sup.+-APTase pump and the fatty acids with increasing degrees of cis-unsaturation had higher potencies. See, Pomposiello, S. I. et al., Hypertension 31:615-20 (1998), which is incorporated by reference herein. Interestingly, the pulmonary vascular response to arachidonic acid, a metabolite of linoleic acid, can be either vasoconstrictive or vasodilative, depending on the dose, animal species, the mode of arachidonic acid administration, and the tones of the pulmonary circulation. For example, arachidonic acid has been reported to cause cyclooxygenase-dependent and -independent pulmonary vasodilation. See, Peddersen, C. O. et al., J. Appl. Physiol. 68(5):1799-808 (1990); and see, Sparwhake, E. W., et al., J. Appl. Physiol. 44:397-495 (1978) and Wicks, T. C. et al., Circ. Res, 38:167-71 (1976), each of which is incorporated by reference herein.

Many studies have reported effects of eicosapentaenoic acid (EPA) and docosahexaenoic acid (DHA) on vascular reactivity after being administered as ingestible forms. Some studies found that EPA-DHA or EPA alone suppressed the vasoconstrictive effect of norepinephrine or increased vasodilatory responses to acetylcholine in the forearm microcirculation. See, Chin, J. P. F., et al., Hypertension 21:22-8 (1993), and Tagawa, H, et al., J Cardiovasc Pharmacol 33:633-40 (1999), each of which is incorporated by reference herein. Another study found that both EPA and DHA increased systemic arterial compliance and tended to reduce pulse pressure and total vascular resistance. See, Nestel, P. et al., Am J. Clin. Nutr. 76:326-30 (2002), which is incorporated by reference herein. Meanwhile, a study found that DHA, but not EPA, enhanced vasodilator mechanisms and attenuates constrictor responses in forearm microcirculation in hyperlipidemic overweight men. See, Mori, T. A., et al., Circulation 102:1264-69 (2000), which is incorporated by reference herein. Another study found vasodilator effects of DHA on the rhythmic contractions of isolated human coronary arteries in vitro. See Wu, K.-T. et al., Chinese J. Physiol. 50(4):164-70 (2007), which is incorporated by reference herein.

The adrenergic receptors (or adrenoceptors) are a class of G protein-coupled receptors that are a target of catecholamines, especially norepinephrine (noradrenaline) and epinephrine (adrenaline). Epinephrine (adrenaline) interacts with both α- and β-adrenoceptors, causing vasoconstriction and vasodilation, respectively. Although areceptors are less sensitive to epinephrine, when activated, they override the vasodilation mediated by β-adrenoceptors because there are more peripheral al receptors than β-adrenoceptors. The result is that high levels of circulating epinephrine cause vasoconstriction. At lower levels of circulating epinephrine, β-adrenoceptor stimulation dominates, producing vasodilation followed by decrease of peripheral vascular resistance. The α1-adrenoreceptor is known for smooth muscle contraction, mydriasis, vasoconstriction in the skin, mucosa and abdominal vicera and sphincter contraction of the gastrointestinal (GI) tract and urinary bladder. The α1-adrenergic receptors are member of the $G_q$ protein-coupled receptor superfamily. Upon activation, a heterotrimeric G protein, $G_q$, activates phospholipase C (PLC). The mechanism of action involves interaction with calcium channels and changing the calcium content in a cell. For review, see Smith R. S. et al., Journal of Neurophysiology, 102(2): 1103-14 (2009), which is incorporated by reference herein. Many cells possess these receptors.

α1-adrenergic receptors can be a main receptor for fatty acids. For example, saw palmetto is extract (SPE), widely used for the treatment of benign prostatic hyperplasia (BPH), has been reported to bind.alpha.1-adrenergic, muscarinic and 1,4-dihydropyridine (1,4-DH P) calcium channel antagonist receptors. See, Abe M., et al., Biol. Pharm. Bull. 32(4) 646-650 (2009), and Suzuki M. et al., Acta Pharmacologica *Sinica* 30:271-81 (2009), each of which is incorporated by reference herein. SPE includes a variety of fatty acids including lauric acid, oleic acid, myristic acid, palmitic acid and linoleic acid. Lauric acid and oleic acid can bind noncompetitively to a 1-adrenergic, muscarinic and 1,4-DHP calcium channel antagonist receptors.

In certain embodiments, a permeation enhancer can be an adrenergic receptor interacter. An adrenergic receptor interacter refers to a compound or substance that modifies and/or otherwise alters the action of an adrenergic receptor. For example, an adrenergic receptor interacter can prevent stimulation of the receptor by increasing, or decreasing their ability to bind. Such interacters can be provided in either short-acting or long-acting forms. Certain short-acting interacters can work quickly, but their effects last only a few hours. Certain long-acting interacters can take longer to work, but their effects can last longer. The interacter can be selected and/or designed based on, e.g., one or more of the desired delivery and dose, active pharmaceutical ingredient, permeation modifier, permeation enhancer, matrix, and the condition being treated. An adrenergic receptor interacter can be an adrenergic receptor blocker. The adrenergic receptor interacter can be a terpene (e.g. volatile unsaturated hydrocarbons found in the essential oils of plants, derived from units of isoprenes) or a C3-C22 alcohol or acid, preferably a C7-C18 alcohol or acid. In certain embodiments, the adrenergic receptor interacter can include farnesol, linoleic acid, arachidonic acid, docosahexanoic acid, eicosapentanoic acid, and/or docosapentanoic acid. The acid can be a carboxylic acid, phosphoric acid, sulfuric acid, hydroxamic acid, or derivatives thereof. The derivative can be an ester or amide. For example, the adrenergic receptor interacter can be a fatty acid or fatty alcohol.

The C3-C22 alcohol or acid can be an alcohol or acid having a straight C3-C22 hydrocarbon chain, for example a C3-C22 hydrocarbon chain optionally containing at least one double bond, at least one triple bond, or at least one double bond and one triple bond; said hydrocarbon chain being optionally substituted with $C_{1-4}$ alkyl, $C_{2-4}$ alkenyl, $C_{2-4}$ alkynyl, $C_{1-4}$ alkoxy, hydroxyl, halo, amino, nitro, cyano. $C_{3-5}$ cycloalkyl, 3-5 membered heterocycloalkyl, monocyclic aryl, 5-6 membered heteroaryl, $C_{1-4}$ alkylcarbonyloxy, $C_{1-4}$ alkylcyloxycarbonyl, $C_{1-4}$ alkylcarbonyl, or formyl; and further being optionally interrupted by —$O_m$—N($R^a$)—, —N($R^a$)—C(O)—O—, —O—C(O)—N($R^a$)—, —N($R^a$)—C(O)—N($R^b$)—, or —O—C(O)—O—. Each of $R^a$ and $R^b$, independently, is hydrogen, alkyl, alkenyl, alkynyl, alkoxy, hydroxylalkyl, hydroxyl, or haloalkyl.

Fatty acids with a higher degree of unsaturation are effective candidates to enhance the permeation of drugs. Unsaturated fatty acids showed higher enhancement than saturated fatty acids, and the enhancement increased with the number of double bonds. See, A. Mittal, et al, Status of Fatty Acids as Skin Penetration Enhancers—A Review, Current Drug Delivery, 2009, 6, pp. 274-279, which is incorporated by reference herein. Position of double bond also affects the enhancing activity of fatty acids. Differences in the physicochemical properties of fatty acid which originate from differences in the double bond position most likely determine the efficacy of these compounds as skin penetration enhancers. Skin distribution increases as the position of the double bond is shifted towards the hydrophilic end. It has also been reported that fatty acid which has a double bond at an even number position more rapidly effects the perturbation of the structure of both the stratum corneum and the dermis than a fatty acid which has double bond at an odd number position. Cis-unsaturation in the chain can tend to increase activity.

An adrenergic receptor interacter can be a terpene. Hypotensive activity of terpenes in essential oils has been reported. See, Menezes I. A. et al., Z. Naturforsch. 65c:652-66 (2010), which is incorporated by reference herein. In certain embodiments, the permeation enhancer can be a sesquiterpene. Sesquiterpenes are a class of terpenes that consist of three isoprene units and have the empirical formula $C_{15}H_{124}$. Like monoterpenes, sesquiterpenes may be acyclic or contain rings, including many unique combinations. Biochemical modifications such as oxidation or rearrangement produce the related sesquiterpenoids.

An adrenergic receptor interacter can be an unsaturated fatty acid such as linoleic acid. In certain embodiments, the permeation enhancer can be farnesol. Farnesol is a 15-carbon organic compound which is an acyclic sesquiterpene alcohol, which is a natural dephosphorylated form of farnesyl pyrophosphate. Under standard conditions, it is a colorless liquid. It is hydrophobic, and thus insoluble in water, but miscible with oils. Farnesol can be extracted from oils of plants such as citronella, neroli, cyclamen, and tuberose. It is an intermediate step in the biological synthesis of cholesterol from mevalonic acid in vertebrates. It has a delicate floral or weak citrus-lime odor and is used in perfumes and flavors. It has been reported that farnesol selectively kills acute myeloid leukemia blasts and leukemic cell lines in preference to primary hemopoietic cells, See, Rioja A. et al., FEBS Lett 467 (2-3): 291-5 (2000), which is incorporated by reference herein. Vasoactive properties of farnesyl analogues have been reported. See, Roullet, J.-B., et al., J. Clin. Invest., 1996, 97:2384-2390, which is incorporated by reference herein. Both Farnesol and N-acetyl-S-trans, trans-famesyl-L-cysteine (AFC), a synthetic mimic of the carboxyl terminus of farnesylated proteins inhibited vasoconstriction in rat aortic rings.

In an embodiment, the film comprises a permeation enhancer that includes one or more of a phenylpropanoid, farnesol, Labrasol, and linoleic acid. In an embodiment, the permeation enhancer is a phenylpropanoid that is selected from the group consisting of: eugenol; eugenol acetate; a cinnamic acid; a cinnamic acid ester; a cinnamic aldehyde; a hydrocinnamic acid; chavicol; safrole; or a combination thereof.

In an embodiment, the film comprises a permeation enhancer that is a phytoextract. The phytoextract may be an essential oil extract of a clove plant, an essential oil extract of a leaf of a clove plant, an essential oil extract of a flower bud of a clove plant, an essential oil extract of a stem of a clove plant, or a combination thereof. In an embodiment, the phytoextract can be synthetic. The phytoextract may include about 20% to about 95% eugenol, about 40% to about 95% eugenol, about 60% to about 95% eugenol, or about 80% to about 95% eugenol.

Uniformity and Manufacture

For the purposes of the present invention the term non-self-aggregating uniform heterogeneity refers to the ability of the films of the present invention, which are formed from one or more components in addition to a polar solvent, to provide a substantially reduced occurrence of, i.e. little or no, aggregation or conglomeration of components within the film as is normally experienced when films are formed by conventional drying methods such as a high-temperature air-bath using a drying oven, drying tunnel, vacuum drier, or other such drying equipment. The term heterogeneity, as used in the present invention, includes films that will incorporate a single component, such as a polymer, as well as combinations of components, such as a polymer and an active. Uniform heterogeneity includes the substantial absence of aggregates or conglomerates as is common in conventional mixing and heat drying methods used to form films.

Furthermore, the films disclosed herein have a substantially uniform thickness, which is also not provided by the use of conventional drying methods used for drying water-based polymer systems. The absence of a uniform thickness may detrimentally affect uniformity of component distribution throughout the area or region of a given film.

The films disclosed herein are produced by a combination of a properly selected polymer and a polar solvent, optionally including an active ingredient as well as other fillers known in the art. These films provide a non-self-aggregating uniform heterogeneity of the components within them by utilizing a selected casting or deposition method and a controlled drying process. Examples of controlled drying processes include, but are not limited to, the use of the apparatus disclosed in U.S. Pat. Nos. 7,425,292; 7,357,891; 7,666,337; 8,603,514; 8,017,150; 8,663,667; 8,652,378; 8.900,497; 8,900,498; 9,108,340; 9,855,221; and 9,931,305 all assigned to Aquestive Therapeutics, Inc., and all of which are incorporated herein in their entirety. Another drying technique for obtaining the films is controlled radiation drying, in the absence of uncontrolled air currents, such as infrared and radio frequency radiation (i.e. microwaves).

The objective of the drying process is to provide a method of drying the films that avoids complications, such as the noted "rippling" and mass transfer effect, that are associated with conventional drying methods and which initially dry the upper surface of the film, trapping moisture inside. In conventional oven drying methods, as the moisture trapped inside subsequently evaporates, the top surface is altered by being ripped open and then reformed. Such surface disruption by continued surface skinning and then reopening the skinned surface to allow evaporation causes non-uniformity in the film and uneven thickness. Additionally, excessive air currents, e.g., hot air currents, may cause mass transfer, i.e., waves in the flowable matrix prior to the matrix obtaining sufficient solidity during the drying process. Such rippling effects, whether caused by surface skinning/rupture/reformation or mass transfer, produce non-uniformity of the active content in the film as particles are subjected to these uncontrolled mechanical and thermal forces and move within the film as a consequence. Such movement destroys the substantial uniformity of active throughout the film achieved during the mixing process and which is required to be maintained in order to produce dosage units of substantially the same size cut from the cast film, each having an amount of active per dosage unit which does not vary more than 10% from the desired amount (labelled amount) of active.

These complications are avoided by the present invention, and a uniform film is provided by preventing skinning/rupture/reformation or mass transfer of the film matrix prior to developing sufficient solidification of the flowable film matrix to prevent active particles from moving and agglomerating or aggregating. The present disclosure provides several methods of controlling the drying process, thereby preventing the deleterious effects present in conventional drying methods and maintaining the substantial uniformity of active in the matrix which was achieved during mixing. Drying is also desirably performed rapidly in order to "lock-in" the active by rapidly developing the viscosity to achieve a sufficiently solid matrix to prevent substantial movement.

The cast and dried film can then be cut into individual dosage units of substantially equal size (length, width and thickness) and those dosage units will have an active content that does not vary more than 10% from the desired amount (labelled) amount of active.

Methods of controlling the undesirable effects of conventional drying include controlling oven air-flow to prevent rippling, prevent mass movement and prevent premature skinning of the surface before the matrix is dry beneath the skin. The air currents are desirably directed at the film from the top and from distances, angles and at speeds such that the force created when they strike the film does not overcome the yield values of the film matrix, i.e., below any force level that can move, or otherwise cause rippling and non-uniformity of the film forming compositions which form the matrix.

Controlled drying may also include directing heat to the bottom surface of the film first to begin the drying from the depth of the film upwards. This may be achieved by applying heat to the bottom surface of the film with substantially no top air flow, or by applying heat to the bottom and the top simultaneously without causing rippling of premature skinning.

Alternatively, drying may be accomplished by the introduction of controlled microwaves to evaporate the water or other polar solvent within the film. When applying microwaves, care must be taken to ensure the temperature of the matrix does not get so high that boiling of the matrix occurs, which would result in non-uniformity of the actives therein.

Yet a further alternative method for controlled drying may include, drying using balanced fluid flow, such as balanced air flow, where the bottom and top air flows are controlled to provide a uniform film and avoid the rippling and premature skinning as described herein. In such a case, the air flow directed at the top of the film should not create a condition which would cause movement of particles present in the wet film, due to forces generated by the air currents. Additionally, air currents directed at the bottom of the film should desirably be controlled such that the film does not lift up due to forces from the air. Uncontrolled air currents, either above or below the film, can create non-uniformity in the final film products. The humidity level of the area surrounding the top surface may also be appropriately adjusted to prevent premature closure or skinning of the polymeric matrix surface.

This manner of drying the films provides several advantages. Among these are the faster drying times and a more uniform surface of the film, as well as uniform distribution of components for any given area in the film. In addition, the faster drying time allows viscosity to quickly build within the film, further encouraging a uniform distribution of components and decrease in aggregation of components in the final film product. Desirably, the drying of the film will occur within about ten minutes or fewer, or more desirably within about five minutes or fewer.

The present invention yields exceptionally uniform film products when attention is paid to reducing the aggregation of the compositional components. Moreover, avoiding the introduction of and eliminating excessive air in the mixing process is desirable in promoting uniformity in the film and dosages cut therefrom; additionally, selecting polymers and solvents to provide a controllable viscosity and by drying the film in a rapid manner as discussed above, while avoiding rippling or mass movement of the film, are desirable in maintaining and providing films and dosage units cut therefrom which have the desired uniformity of active content when pared to the labelled amount. Such uniformity of active content in the dosage units is thus achieved through attention to these parameters.

The products and processes of the present disclosure rely on the interaction among various steps of the production of the films in order to provide films that substantially reduce the self-aggregation of the components within the films. Specifically, these steps include the particular method used to form the film, making the composition mixture to prevent air bubble inclusions, controlling the viscosity of the film forming composition and the method of drying the film. More particularly, a greater viscosity of components in the mixture is particularly useful when the active is not soluble in the selected polar solvent in order to prevent the active from settling out. However, the viscosity must not be too great as to hinder or prevent the chosen method of casting, which desirably includes reverse roll coating due to its ability to provide a film of substantially consistent thickness.

In addition to the viscosity of the film or film-forming components or matrix, there are other considerations taken into account for achieving desirable film uniformity. For example, stable suspensions are achieved which prevent solid (such as drug particles) sedimentation in non-colloidal applications. One approach provided by the present invention is to balance the density of the particulate ($\rho_p$) and the liquid phase ($\rho_l$) and increase the viscosity of the liquid phase ($\mu$). For an isolated particle, Stokes law relates the terminal settling velocity (Vo) of a rigid spherical body of radius (r) in a viscous fluid, as follows:

$$V_o = (2gr^2)(\rho_p - \rho_l)/9\mu.$$

At high particle concentrations, however, the local particle concentration will affect the local viscosity and density. The viscosity of the suspension is a strong function of solids volume fraction, and particle-particle and particle-liquid interactions will further hinder settling velocity.

Stokian analyses has shown that the incorporation of a third phase, dispersed air or nitrogen, for example, promotes suspension stability. Further, increasing the number of particles leads to a hindered settling effect based on the solids volume fraction. In dilute particle suspensions, the rate of sedimentation, v, can be expressed as:

$$v/V_o = 1/(1+\kappa\varphi)$$

where $\kappa$=a constant, and $\varphi$ is the volume fraction of the dispersed phase. More particles suspended in the liquid phase results in decreased velocity. Particle geometry is also an important factor since the particle dimensions will affect particle-particle flow interactions.

Similarly, the viscosity of the suspension is dependent on the volume fraction of dispersed solids. For dilute suspensions of non-interaction spherical particles, an expression for the suspension viscosity can be expressed as:

$$\mu/\mu_o = 1 + 2.5\varphi$$

where $\mu_o$ is the viscosity of the continuous phase and $\varphi$ is the solids volume fraction. At higher volume fractions, the viscosity of the dispersion can be expressed as $$\mu/\mu_o=1+2.5\varphi+C_{1\varphi}{}^2+C_{2\varphi}{}^3+$$

where C is a constant.

The viscosity of the liquid phase is critical and is desirably modified by customizing the liquid composition to a viscoelastic non-Newtonian fluid with low yield stress values. This is the equivalent of producing a high viscosity continuous phase at rest. Formation of a viscoelastic or a highly structured fluid phase provides additional resistive forces to particle sedimentation. Further, flocculation or aggregation can be controlled minimizing particle-particle interactions. The net effect would be the preservation of a homogeneous dispersed phase.

The addition of hydrocolloids to the aqueous phase of the suspension increases viscosity, may produce viscoelasticity and can impart stability depending on the type of hydrocolloid, its concentration and the particle composition, geometry, size, and volume fraction. The average particle size distribution of the dispersed phase needs to be controlled by selecting the smallest realistic average particle size in the high viscosity medium, i.e., <500 µm. The presence of a slight yield stress or elastic body at low shear rates may also induce permanent stability regardless of the apparent viscosity. The critical particle diameter can be calculated from the yield stress values. In the case of isolated spherical particles, the maximum shear stress developed in settling through a medium of given viscosity can be given as $$\tau_{max}=3V\mu/2r.$$

For pseudoplastic fluids, the viscosity in this shear stress regime may well be the zero shear rate viscosity at the Newtonian plateau.

A stable suspension is an important characteristic for the manufacture of a pre-mix composition which is to be fed into the film casting machinery film, as well as the maintenance of this stability in the wet film stage until sufficient drying has occurred to lock-in the particles and matrix into a sufficiently solid form such that uniformity is maintained. For viscoelastic fluid systems, a rheology that yields stable suspensions for extended time period, such as 24 hours, must be balanced with the requirements of high-speed film casting operations. A desirable property for the films is shear thinning or pseudoplasticity, whereby the viscosity decreases with increasing shear rate. Time dependent shear effects such as thixotropy are also advantageous. Structural recovery and shear thinning behavior are important properties, as is the ability for the film to self-level as it is formed.

The rheology requirements for the inventive compositions and films are quite severe. This is due to the need to produce a stable suspension of particles, for example 30-60 wt %, in a viscoelastic fluid matrix with acceptable viscosity values throughout a broad shear rate range. During mixing, pumping, and film casting, shear rates in the range of $10-10^5$ sec.$^{-1}$ may be experienced and pseudoplasticity is the preferred embodiment.

In film casting or coating, rheology is also a defining factor with respect to the ability to form films with the desired uniformity. Shear viscosity, extensional viscosity, viscoelasticity, structural recovery will influence the quality of the film. As an illustrative example, the leveling of shear-thinning pseudoplastic fluids has been derived as $$\alpha^{(n-1/n)}=\alpha_o{}^{(n-1/n)}-((n-1)/(2n-1))(\Sigma/K)^{1/n}$$
$$(2\pi/\lambda)^{(3+n)/n}h^{(2n+1)/n}t$$

where $\alpha$ is the surface wave amplitude, $\alpha_o$ is the initial amplitude, $\lambda$ is the wavelength of the surface roughness, and both "n" and "K" are viscosity power law indices. In this example, leveling behavior is related to viscosity, increasing as n decreases, and decreasing with increasing K.

Desirably, the films or film-forming compositions of the present disclosure have a very rapid structural recovery, i.e., as the film is formed during processing, it doesn't fall apart or become discontinuous in its structure and compositional uniformity. Such very rapid structural recovery retards particle settling and sedimentation. Moreover, the films or film-forming compositions are desirably shear-thinning pseudoplastic fluids. Such fluids with consideration of properties, such as viscosity and elasticity, promote thin film formation and uniformity.

Thus, uniformity in the mixture of components depends upon numerous variables. As described herein, viscosity of the components, the mixing techniques and the rheological properties of the resultant mixed composition and wet casted film are important aspects of the present invention. Additionally, control of average particle size and particle shape are further considerations. Desirably, the average particle size may be 200 microns or less, 150 microns or less, or 100 microns or less. Moreover, such particles may be spherical, substantially spherical, or non-spherical, such as irregularly shaped particles or ellipsoidally shaped particles. Ellipsoidally shaped particles or ellipsoids are desirable because of their ability to maintain uniformity in the film forming matrix as they tend to settle to a lesser degree as compared to spherical particles.

A number of techniques may be employed in the mixing stage to prevent bubble inclusions in the final film. To provide a composition mixture with substantially no air bubble formation in the final product, anti-foaming or surface-tension reducing agents are employed. Additionally, the speed of the mixture is desirably controlled to prevent cavitation of the mixture in a manner which pulls air into the mix. Finally, air bubble reduction can further be achieved by allowing the mix to stand for a sufficient time for bubbles to escape prior to drying the film. Desirably, the inventive process first forms a masterbatch of film-forming components without active ingredients such as drug particles or volatile materials such as flavor oils. The actives are added to smaller mixes of the masterbatch just prior to casting. Thus, the masterbatch pre-mix can be allowed to stand for a longer time without concern for instability in drug or other ingredients.

When the matrix is formed including the film-forming polymer and polar solvent in addition to any additives and the active ingredient, this may be done in a number of steps. For example, the ingredients may all be added together or a pre-mix may be prepared. The advantage of a pre-mix is that all ingredients except for the active may be combined in advance, with the active added just prior to formation of the film. This is especially important for actives that may degrade with prolonged exposure to water, air or another polar solvent.

An apparatus for the preparation of the films of the invention is disclosed, for example in U.S. Pat. No. 8,765,167, the entire contents of which are incorporated herein in its entirety.

Moreover, the films disclosed herein may contain particles that are sensitive to temperature, such as flavors, which may be volatile, or drugs, which may have a low degradation temperature. In such cases, the drying temperature may be decreased while increasing the drying time to adequately dry the uniform films of the present invention.

Furthermore, bottom drying also tends to result in a lower internal film temperature as compared to top drying. In bottom drying, the evaporating vapors more readily carry heat away from the film as compared to top drying which lowers the internal film temperature. Such lower internal film temperatures often result in decreased drug degradation and decreased loss of certain volatiles, such as flavors.

Furthermore, particles or particulates may be added to the film-forming composition or matrix after the composition or matrix is cast into a film. For example, particles may be added to the film prior to the drying of the film. Particles may be controllably metered to the film and disposed onto the film through a suitable technique, such as through the use of a doctor blade (not shown) which is a device which marginally or softly touches the surface of the film and controllably disposes the particles onto the film surface. Other suitable, but non-limiting, techniques include the use of an additional roller to place the particles on the film surface, spraying the particles onto the film surface, and the like. The particles may be placed on either or both of the opposed film surfaces, i.e., the top and/or bottom film surfaces. Desirably, the particles are securely disposed onto the film, such as being embedded into the film. Moreover, such particles are desirably not fully encased or fully embedded into the film, but remain exposed to the surface of the film, such as in the case where the particles are partially embedded or partially encased.

The particles may be any useful organoleptic agent, cosmetic agent, pharmaceutical agent, or combinations thereof. Desirably, the pharmaceutical agent is a taste-masked or a controlled-release pharmaceutical agent. Useful organoleptic agents include flavors and sweeteners. Useful cosmetic agents include breath freshening or decongestant agents, such as menthol, including menthol crystals.

Monitoring and control of the thickness of the film also contributes to the production of a uniform film by providing a film of uniform thickness. The thickness of the film may be monitored with gauges such as Beta Gauges. A gauge may be coupled to another gauge at the end of the drying apparatus, i.e. drying oven or tunnel, to communicate through feedback loops to control and adjust the opening in the coating apparatus, resulting in control of uniform film thickness.

The film products are generally formed by combining a properly selected polymer and polar solvent, as well as any active ingredient or filler as desired. Desirably, the solvent content of the combination is at least about 30% by weight of the total combination. The matrix formed by this combination is formed into a film, desirably by roll coating, and then dried, desirably by a rapid and controlled drying process to maintain the uniformity of the film, more specifically, a non-self-aggregating uniform heterogeneity. The resulting film will desirably contain less than about 10% by weight solvent, more desirably less than about 8% by weight solvent, even more desirably less than about 6% by weight solvent and most desirably less than about 2%. The solvent may be water, a polar organic solvent including, but not limited to, ethanol, isopropanol, acetone, methylene chloride, or any combination thereof.

Consideration of the above discussed parameters, such as but not limited to rheology properties, viscosity, mixing method, casting method and drying method, also impact material selection for the different components of the present invention. Furthermore, such consideration with proper material selection provides the compositions of the present invention, including a pharmaceutical and/or cosmetic dosage form or film product which has a substantially uniform distribution of the active(s) within the cast wet film and which retains this substantially uniform distribution during the drying process, such that equal sized dosage units can be cut from the continuously cast and dried film, which dosage units have a substantially uniform amount of active present when compared to the desired amount of active, i.e., the labelled amount of active for each dosage unit. Desirably, the uniformity of the continuously cast self-supporting film is measured by substantially equally sized individual unit doses cut from a self-supporting continuously cast film which do not vary by more than 10% of the desired amount of said at least one active. For clarity, assume the desired amount of a unit dosage of film may be, for example, 10 mg of a given drug(s). The films of the present invention require a uniformity such that substantially equal unit dosages of film cut from the continuously cast and dried film will not vary more than 10% of the desired amount, i.e. unit doses will vary no more than +/−1 mg or in other words 9 mg-11 mg.

Forming the Film

The films disclosed herein must be formed into a continuously cast wet film or wet sheet prior to drying. The term "continuously cast" is intended to refer to relatively high speed manufacturing processes using conveyor substrates onto which the wet film matrix is cast and formed and which is then continued into an a drying apparatus, such as an oven, and then further conveyed continuously either onto a roll-up mandrel for storage or directly into a cutting and packaging station. The term continuously is intended to distinguish processes such as those performed in a laboratory setting, e.g., wherein a wet film matrix is cast onto a tray.

After the desired components are combined to form a multi-component substantially uniform matrix, including the polymer, water, and an active or other components as desired, the combination is formed into a wet sheet or film, by any method known in the art such as extrusion, coating, spreading, casting or drawing the multi-component matrix. If a multi-layered film is desired, this may be accomplished by co-extruding more than one combination of components which may be of the same or different composition. A multi-layered film may also be achieved by continuously coating, continuously spreading, or continuously casting a wet film matrix onto an already formed, and desirably already dried, film layer.

Although a variety of different continuous film-forming techniques may be used, it is desirable to select a method that will provide a flexible film, such as reverse roll coating. The flexibility of the film allows for the sheets of film to be rolled and transported for storage or prior to being cut into individual dosage forms. Desirably, the films will also be self-supporting or in other words able to maintain their integrity and structure in the absence of a separate support. Furthermore, the films of the present invention may be selected of materials that are edible or ingestible.

Continuous coating or continuous casting methods are particularly useful for the purpose of forming the films of the present invention. Specific examples include reverse roll coating, gravure coating, immersion or dip coating, metering rod or meyer bar coating, slot die or extrusion coating, gap or knife over roll coating, air knife coating, curtain coating, or combinations thereof, especially when a multi-layered film is desired.

Continuous roll coating, or more specifically reverse roll coating, is particularly desired when forming films in accordance with the present invention. This procedure provides excellent control and uniformity of the resulting films, which is desired in the present invention. In this procedure, the coating material is measured onto the applicator roller by the precision setting of the gap between the upper metering roller and the application roller below it. The coating is transferred from the application roller to the substrate as it passes around the support roller adjacent to the application roller. Both three roll and four roll processes are common.

The gravure coating process relies on an engraved roller running in a coating bath, which fills the engraved dots or lines of the roller with the coating material. The excess coating on the roller is wiped off by a doctor blade and the coating is then deposited onto the substrate as it passes between the engraved roller and a pressure roller.

Offset Gravure is common, where the coating is deposited on an intermediate roller before transfer to the substrate.

In the simple process of immersion or dip coating, the substrate is dipped into a bath of the coating, which is normally of a low viscosity to enable the coating to run back into the bath as the substrate emerges.

In the metering rod coating process, an excess of the coating is deposited onto the substrate as it passes over the bath roller. The wire-wound metering rod, sometimes known as a Meyer Bar, allows the desired quantity of the coating to remain on the substrate. The quantity is determined by the diameter of the wire used on the rod.

In the slot die process, the coating is squeezed out by gravity or under pressure through a slot and onto the substrate. If the coating is 100% solids, the process is termed "Extrusion" and in this case, the line speed is frequently much faster than the speed of the extrusion. This enables coatings to be considerably thinner than the width of the slot.

The gap or knife over roll process relies on a coating being applied to the substrate which then passes through a "gap" between a "knife" and a support roller. As the coating and substrate pass through, the excess is scraped off.

Air knife coating is where the coating is applied to the substrate and the excess is "blown off" by a powerful jet from the air knife. This procedure is useful for aqueous coatings.

In the curtain coating process, a bath with a slot in the base allows a continuous curtain of the coating to fall into the gap between two conveyors. The object to be coated is passed along the conveyor at a controlled speed and so receives the coating on its upper face.

The substrate may be any material known for use in the art. For example, it may be a polyester film, such as polyethylene terephthalate, plastic sheet, glass or a cellulose-based paper, optionally coated. The substrate may be polyethylene terephthalate (e.g., mylar) or parchment paper. When the substrate is polyethylene terephthalate, it may be biaxially-oriented polyethylene terephthalate, which optionally has been corona treated on its bottom or top surface.

Drying the Film

The drying step is also a contributing factor with regard to maintaining the uniformity of the film composition. A controlled drying process is particularly important when, in the absence of a viscosity increasing composition or a composition in which the viscosity is controlled, for example by the selection of the polymer, the components within the film may have an increased tendency to aggregate or conglomerate. An alternative method of forming a film with an accurate dosage, that would not necessitate the controlled drying process, would be to cast the films on a predetermined well or to apply the desired amount of active to individual dosage units after the dosage units are cut from a continuously cast film (which do not contain active) on a manufacturing line. These two alternative methods do not have the same challenges associated with maintaining the uniformity of active content from the mixing process through the drying process as does the continuously cast films which incorporate the active in the film matrix prior to casting. With these alternative methods, there is no chance that migration of the active to an adjacent dosage form will occur. When a controlled or rapid drying process is desired, this may be accomplished through a variety of methods. A variety of methods may be used including those that require the application of heat. The liquid carriers are removed from the film in a manner such that the uniformity, or more specifically, the non-self-aggregating uniform heterogeneity, that is obtained in the wet film is maintained.

As described above, the wet continuously cast film is dried using thermal air currents which do not produce rippling of the wet, flowable cast film matrix, mass transfer of the wet, flowable cast film matrix, or premature surface skinning as discussed above. The parameters chosen to achieve this include ensuring the air currents are directed at the film from the top at from distances, angles and at speeds such that the force created when they strike the film does not overcome the yield values of the film matrix, i.e. below any force level that can move, or otherwise cause rippling and non-uniformity of the film forming compositions which form the matrix. Desirably, but not necessarily, the film is exposed to a high temperature differential as the film enters the oven, such that the water content is rapidly removed to quickly solidify the flowable matrix and lock-in the active within a more solid structure. In so doing and as long as care is taken to ensure the uniformity of the film is preserved throughout the drying process, the continuously cast film matrix may be dried using air solely emanating from the top or above the conveying substrate, using air solely emanating from the bottom of the conveying substrate, or by using air from both above and below the conveying substrate (top and bottom of the film).

Thus, in one aspect of the drying process, the film may be dried from the bottom of the film to the top of the film. Desirably, any top air flow present must not cause the non-uniformity conditions discussed above. Once the initial setting period has passed and a sufficiently solid, visco-elastic structure is formed, the likelihood of creating ripples and premature skinning is greatly reduced, if not eliminated. This can take place within the first few minutes, e.g. about the first 0.5 to about 4.0 minutes of the drying process. Controlling the drying in this manner, prevents the destruction and reformation of the film's top surface, which results from conventional drying methods. Drying continuously cast wet film in a manufacturing setting includes casting the wet flowable film matrix onto a conveying substrate In some instances it may be preferable to begin the drying process by supplying air currents to the bottom surface of the film, and hence below the conveying substrate. The heat from the air currents in this case is initially applied to the bottom side of the film to provide the necessary energy to evaporate or otherwise remove the liquid carrier. The films dried in this manner dry more quickly and evenly as compared to air-dried films (left to dry in the open air), or those dried by conventional drying means. In contrast to an air-dried film that dries first at the top and edges, the films dried by applying heat to the bottom dry simultaneously at the center as well as at the edges. This also prevents settling of ingredients that occurs with films dried by conventional means. The exogenous air temperature at which the films are dried may be about 130° C. or less, provided the film matrix per se does not reach a boiling point (e.g., 100° C.) or a high enough temperature which would destroy its uniformity.

Desirably, the exogenous air temperature may be about 100° C. or less, or about 80° C. or less.

Another method of controlling the drying process, which may be used alone or in combination with other controlled methods as disclosed above includes controlling and modifying the humidity within the drying apparatus where the film is being dried. In this manner, the premature drying of the top surface of the film may be avoided.

Additionally, it has also been discovered that the length of drying time can be properly controlled, i.e. balanced with the heat sensitivity and volatility of the components, and particularly the flavor oils and drugs. The amount of energy, temperature and length and speed of the conveyor can be balanced to accommodate such actives and to minimize loss, degradation or ineffectiveness in the final film.

A specific example of an appropriate drying method is that disclosed by U.S. Pat. No. 4,631,837 to Magoon ("Magoon"), herein incorporated by reference, which is specifically directed toward a method of drying fruit pulp. In one embodiment of the invention, the present inventors have adapted this process toward the preparation of thin films.

The method and apparatus of Magoon are based on an interesting property of water. Although water transmits energy by conduction and convection both within and to its surroundings, water only radiates energy within and to water. Therefore, the apparatus of Magoon includes a surface onto which the fruit pulp is placed that is transparent to infrared radiation. The underside of the surface is in contact with a temperature controlled water bath. The water bath temperature is desirably controlled at a temperature slightly below the boiling temperature of water. When the wet fruit pulp is placed on the surface of the apparatus, this creates a "refractance window." This means that infrared energy is permitted to radiate through the surface only to the area on the surface occupied by the fruit pulp, and only until the fruit pulp is dry. The apparatus of Magoon provides the films of the present invention with an efficient drying time reducing the instance of aggregation of the components of the film.

The thickness of the final, dried self-supporting films and dosage units made therefrom disclosed herein may vary, depending on the thickness of each of the layers and the number of layers. Both the thickness and number of layers (i.e., one layer or multi-layered, e.g., two, three, four or more) may be adjusted in order to vary the erosion kinetics. The films may initially have a thickness of about 500 μm to about 1,500 μm, or about 20 mils to about 60 mils, and when dried have a thickness from about 3 μm to about 250 μm, or about 0.1 mils to about 10 mils. Desirably, the dried films will have a thickness of about 2 mils to about 8 mils, and more desirably, from about 3 mils to about 6 mils.

If the final self-supporting film product (or dosage units made therefrom) has two layers, the total film thickness may range from about 0.005 mm to about 2 mm, from about 0.01 mm to about 1 mm, or from about 0.1 mm to about 0.5 mm. The total film thickness may be greater than about 0.1 mm, greater than about 0.2 mm, about 0.5 mm, greater than about 0.5 mm, less than about 0.5 mm, less than about 0.2 mm, or less than about 0.1 mm. The thickness of each layer may vary from about 10% to about 90%, or from about 30% to about 60%, of the total thickness of the layered self-supporting film. Any one layer may be greater than 10%, greater than 20%, greater than 30%, greater than 40%, greater than 50%, greater than 60%, greater than 70%, about 90%, less than 90%, less than 70%, less than 50%, less than 40%, less than 30%, less than 20%, or less than 10% of the total thickness of the layered self-supporting film. The preferred thickness of each layer may vary from about 0.01 mm to about 0.9 mm, or from about 0.03 mm to about 0.5 mm.

The final film products and dosage units disclosed herein may dissolve (which includes dispersing and dissolving) in about 30 seconds to about 24 hours, about 30 seconds to about 30 minutes, about 1 minute to about 24 hours, about 1 minute to about 30 minutes, about 1 minute to about 20 minutes, about 3 minutes to about 40 minutes, or about 5 minutes to about 30 minutes. The final self-supporting film products and dosage units disclosed herein may dissolve in more than about 1 minute, more than 5 about minutes, more than about 7 minutes, more than about 10 minutes, more than about 12 minutes, more than about 15 minutes, more than about 20 minutes, more than about 30 minutes, about 30 minutes, or less than about 30 minutes, less than about 20 minutes, less than about 15 minutes, less than about 12 minutes, less than about 10 minutes, less than about 7 minutes, less than about 5 minutes, or less than about 1 minute. Sublingual dissolution rates may be shorter than buccal dissolution rates.

More specifically, oral dissolving film dosage units (also referred to as "unit doses") can fall into three main classes: fast dissolving, moderate dissolving and slow dissolving. Oral dissolving film dosage units may also include a combination of any of the above categories. Fast dissolving film dosage units may dissolve in about 1 second to about 30 seconds in the mouth, including more than about 1 second, more than about 5 seconds, more than about 10 seconds, more than about 20 seconds, and less than about 30 seconds. Moderate dissolving film dosage units may dissolve in about 1 to about 30 minutes in the mouth, including more than about 1 minute, more than about 5 minutes, more than about 10 minutes, more than about 20 minutes, and less than about 30 minutes. Slow dissolving film dosage units may dissolve in more than about 30 minutes in the mouth, including about 30 minutes to about 24 hours, about 30 minutes to about 12 hours, about 30 minutes to about 10 hours, and about 1 hour to about 10 hours. Fast dissolving film dosage units may include (or consist of) low molecular weight hydrophilic polymers (e.g., polymers having a molecular weight between about 1,000 to about 9,000 daltons, or polymers having a molecular weight up to about 200,000 daltons). In contrast, slow dissolving film dosage units may include high molecular weight polymers (e.g., having a molecular weight in millions).

There may be certain advantages to moderate dissolving film dosage units in that they may dissolve rather quickly, while having a good level of mucoadhesion. Moderate dissolving film dosage units may also be flexible, quickly wettable, and are typically non-irritating to the patient. Such moderate dissolving film dosage units may provide a quick enough dissolution rate, for example, between about 1 minute and about 20 minutes, while providing an acceptable mucoadhesion level such that the film is not easily removable once it is placed in the oral cavity of the patient. This may ensure complete delivery of a pharmaceutical active to a patient.

Self-supporting means that the film maintains its integrity and structure in the absence of any separate support. The films of the present disclosure are formulated for absorption in the oral mucosa, that is, e.g., buccal or sublingual. Although a variety of different film-forming techniques may be used, it is desirable to select a method that will provide a flexible film, such as reverse roll coating. The flexibility of the film allows for the sheets of film to be rolled and transported for storage or prior to being cut into individual dosage forms.

Uses of Thin Films

The thin films disclosed herein are well suited for many uses. The high degree of uniformity of the components of the film makes them particularly well suited for incorporating pharmaceuticals. Furthermore, the polymers used in construction of the films may be chosen to allow for a range of disintegration times for the films. A variation or extension in the time over which a film will disintegrate may achieve control over the rate that the active is released, which may allow for a sustained release delivery system. In addition, the films may be used for the administration of an active to any of several body surfaces, especially those including mucous membranes, such as oral, anal, vaginal, ophthalmological, the surface of a wound, either on a skin surface or within a body such as during surgery, and similar surfaces.

The films may be used to orally administer an active. This is accomplished by preparing the films as described above and introducing them to the oral cavity of a mammal. This film may be prepared and adhered to a second or support layer from which it is removed prior to use, i.e. introduction to the oral cavity. An adhesive may be used to attach the film to the support or backing material which may be any of those known in the art, and is preferably not water soluble. If an adhesive is used, it will desirably be a food grade adhesive that is ingestible and does not alter the properties of the active. Mucoadhesive compositions are particularly useful. The film compositions in many cases serve as mucoadhesives themselves.

The films may be applied under or to the tongue of the mammal. When this is desired, a specific film shape, corresponding to the shape of the tongue may be preferred. Therefore, the film may be cut to a shape where the side of the film corresponding to the back of the tongue will be longer than the side corresponding to the front of the tongue. Specifically, the desired shape may be that of a triangle or trapezoid. Desirably, the film will adhere to the oral cavity preventing it from being ejected from the oral cavity and permitting more of the active to be introduced to the oral cavity as the film dissolves.

Another use for the films disclosed herein takes advantage of the films' tendency to dissolve quickly when introduce to a liquid. An active may be introduced to a liquid by preparing a film in accordance with the present invention, introducing it to a liquid, and allowing it to dissolve. This may be used either to prepare a liquid dosage form of an active, or to flavor a beverage.

The films of the present invention are desirably packaged in sealed, air and moisture resistant packages to protect the active from exposure oxidation, hydrolysis, volatilization and interaction with the environment. Moreover, the films of the present invention dissolve instantly upon contact with saliva or mucosal membrane areas, eliminating the need to wash the dose down with water.

Desirably, a series of such unit doses are packaged together in accordance with the prescribed regimen or treatment, e.g., a 10-90-day supply, depending on the particular therapy. The individual self-supporting films can be packaged individually without a backing, or on a backing and peeled off for use.

Methods of Use

Also disclosed herein are methods of treating epilepsy, epileptic seizures, and other forms of seizures in a human comprising administering to the human an oral film for delivery of a desired amount of an active in an individual unit dose. The film comprises: a) a water-soluble polymer matrix, a water swellable polymer matrix, or a water-soluble and water swellable polymer matrix; b) the active having an average particle size D90 of less than about 160 microns; and c) an additive selected from the group consisting of a sweetener, a flavor, a flavor enhancer, a filler, a plasticizer, a dye, a pigment, a permeation enhancer, a buffer, a preservative, silicon dioxide, an anti-tacking agent, and any combination thereof. The active in the oral film may have any of the dissolution profiles and rates discussed above.

The active may be any of the actives described herein. In certain embodiments, the active may be clobazam, diazepam, riluzole, or any combination thereof.

Another embodiment is directed to a method of treating Lennox-Gastaut syndrome in a human comprising administering to the human the oral film disclosed herein.

The terms used in connection with these embodiments (methods of use) have the same meanings and definitions as discussed above.

The features and advantages of the present invention are more fully shown by the following examples which are provided for purposes of illustration, and are not to be construed as limiting the invention in any way.

EXAMPLES

Example 1—Clobazam

Oral films having the following composition shown in Table 1 were prepared to compare milled and micronized active.

TABLE 1

Formulation for Oral Films Containing Milled or Micronized Clobazam

| Component | % solids (w/w) | 5 mg COSF (mg) | 10 mg COSF (mg) | 20 mg COSF (mg) |
|---|---|---|---|---|
| Clobazam | 12.50 | 5.00 | 10.00 | 20.00 |
| Polyethylene oxide | 53.80 | 21.52 | 43.04 | 86.08 |
| Cellulose ether | 6.20 | 2.48 | 4.96 | 9.92 |
| Sugar alcohol | 15.00 | 6.00 | 12.00 | 24.00 |
| Flavoring | 4.00 | 1.60 | 3.20 | 6.40 |
| Artificial sweetener | 3.00 | 1.20 | 2.40 | 4.80 |
| Sodium phosphate dibasic | 2.90 | 1.16 | 2.32 | 4.64 |
| Food acid | 2.10 | 0.84 | 1.68 | 3.36 |
| Monoglyceride ester | 0.50 | 0.20 | 0.40 | 0.80 |
| TOTAL (% or mg) | 100.0 | 40.0 | 80.0 | 160.0 |

Figure 3:
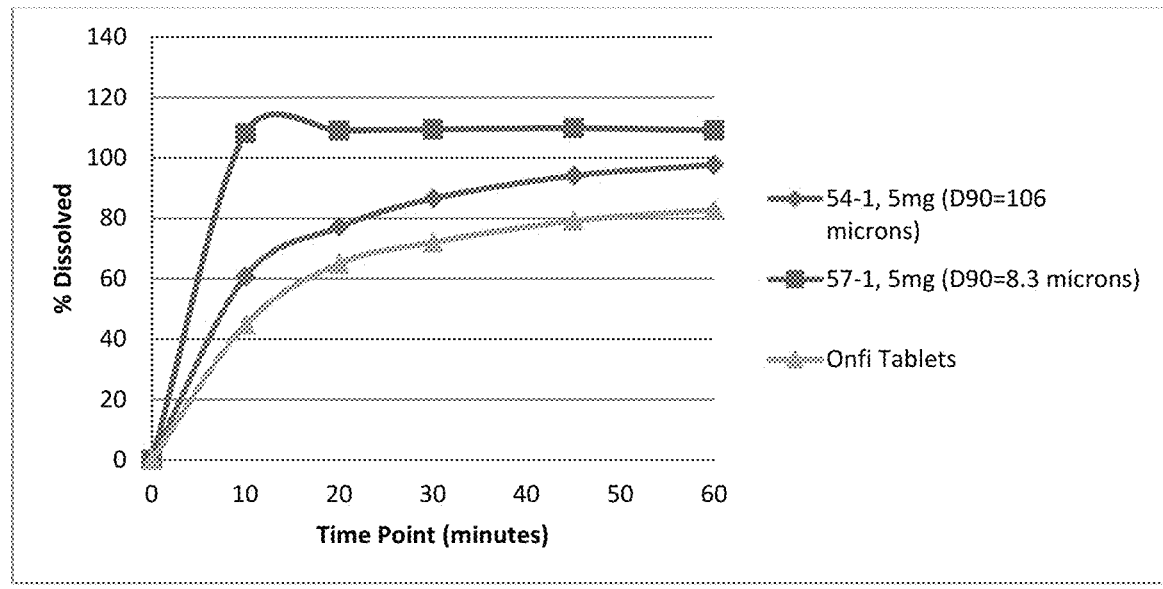
FIG. 3 is a graph showing dissolution of the active in oral films containing 5 mg clobazam milled (D90=106 microns) and 5 mg clobazam (D90=8.3 microns), and an oral tablet containing clobazam.

FIG. 3 shows the average active dissolution plot for films (N=3) containing 5 mg clobazam milled (unmicronized) (D90=106 microns) and micronized (D90=8.3 microns), as well as the RLD Onfi Tablet, 2×10 mg tablets. Table 2 presents some of the graphically depicted data points shown in FIG. 3.

TABLE 2

Dissolution Testing for Oral Films Containing Milled or Micronized Clobazam

| Time (Minutes) | Average % Dissolved Milled Clobazam | Average % Dissolved Micronized Clobazam |
|---|---|---|
| 10 | 60.8 | 108.2 |
| 20 | 77.1 | 109.0 |

TABLE 2-continued

Dissolution Testing for Oral Films Containing Milled or Micronized Clobazam

| Time (Minutes) | Average % Dissolved Milled Clobazam | Average % Dissolved Micronized Clobazam |
|---|---|---|
| 30 | 86.5 | 109.4 |
| 45 | 94.1 | 109.8 |
| 60 | 97.7 | 109.1 |

Accordingly, oral films containing micronized clobazam performed better (i.e., dissolved significantly faster) than oral films containing milled clobazam.

Example 2—Dissolution Study of Oral Films Containing Diazepam

Oral thin films containing diazepam (DBSF) were prepared containing 5 mg and 15 mg of the active. Dissolution of 5 mg and 15 mg DBSF under storage conditions of 12 months at 25° C. was tested using traditional dissolution and PION technology. Traditional dissolution as used herein is a common approach to testing dissolution characteristics of solid oral dosage forms, such as tablets and capsules. The traditional dissolution method utilizes a modified USP Apparatus 5 setup, with a modified sample holder necessary for holding the film stationary. All other aspects of the traditional dissolution method are similar to those of other solid oral dosage forms, including manual sampling and collection of samples at specified time points, then offline analysis of the samples using HPLC. The traditional dissolution method is limited in practical terms to the frequency and consistency of manual sampling and removal of sample aliquots. The PION technology utilizes a traditional dissolution bath, with a non-traditional setup. The bath is setup with an Apparatus 2 (paddle) with a modified sample holder mounted above the paddle. In-line fiber optic probes are positioned inside the vessel. The samples are tested in-situ at predefined intervals. The sampling is automated and analyzed in-line with no sample removal, manual sampling, or offline HPLC testing necessary. A comparison of system parameters between the traditional dissolution and PION technology for testing DBSF are presented in Table 3.

TABLE 3

Exemplary System Parameters for Traditional Dissolution and PION Technology

| Parameter | Set-point (Traditional) | Set-point (PION) |
|---|---|---|
| Dissolution Apparatus | USP <724> Apparatus 5 with 56mm, 120 mesh stainless steel discs used as sinkers | USP <711> Apparatus 2 with Custom Mesh Clip suspended above paddle |
| Rotation Speed | 100 RPM | 100 RPM |
| Media | 0.5% Sodium Lauryl Sulfate | 0.5% Sodium Lauryl Sulfate |
| Media Temperature | 37° C. | 37° C. |
| Media Volume | 900 Ml | 900 mL |
| Sampling Time Points | 5, 10, 15, 20, 30, 45, 60 minutes | Adjustable, minimum of 1 second intervals |
| Sample Volume | 5 Ml | Not Applicable, all sampling and analysis is performed in-situ with no offline analysis necessary |
| Sample Filter | 10 µm Full Flow | |
| HPLC Column | Zorbax Phenyl 5 µm, 4.6 mm × 150 mm | |
| Mobile Phase | 20 mM KH2PO4 Buffer Solution/ Acetonitrile, 50/50 ratio | |
| Flow Rate | 1.0 mL/minute | |
| Column Temperature | 30° C. | |
| Injection Volume | 40 µL | |
| Detection Wavelength | 242 nm | 200 nm-720 nm |
| Run time | 10 minutes | Not Applicable |

Figure 4:
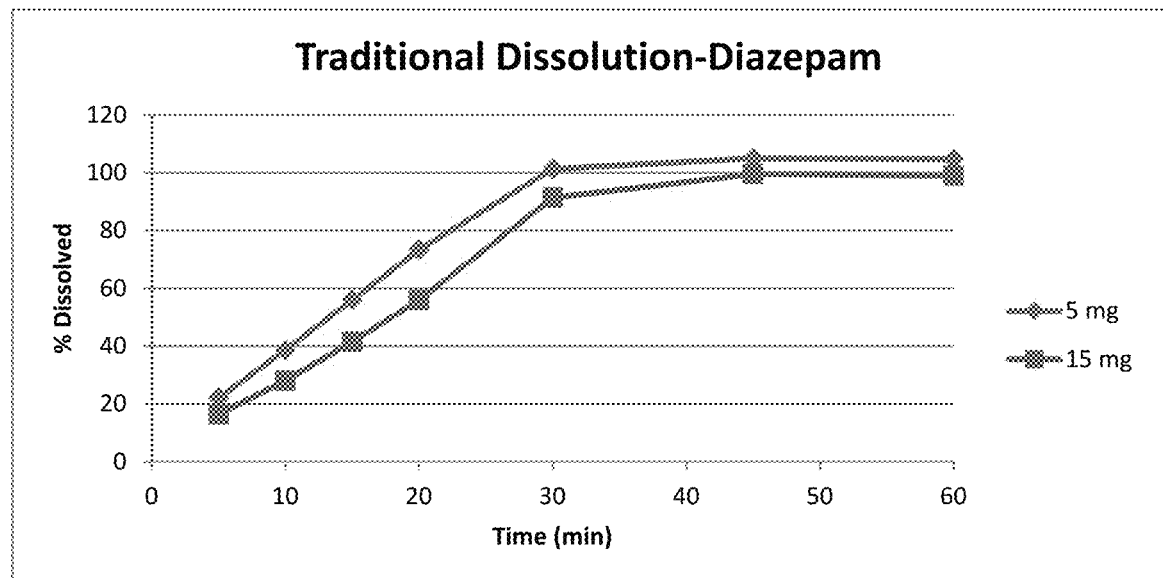
FIG. 4 is a graph of the average active dissolution profile for oral films containing 5 mg and 15 mg of diazepam measured by traditional dissolution.
Figure 5:
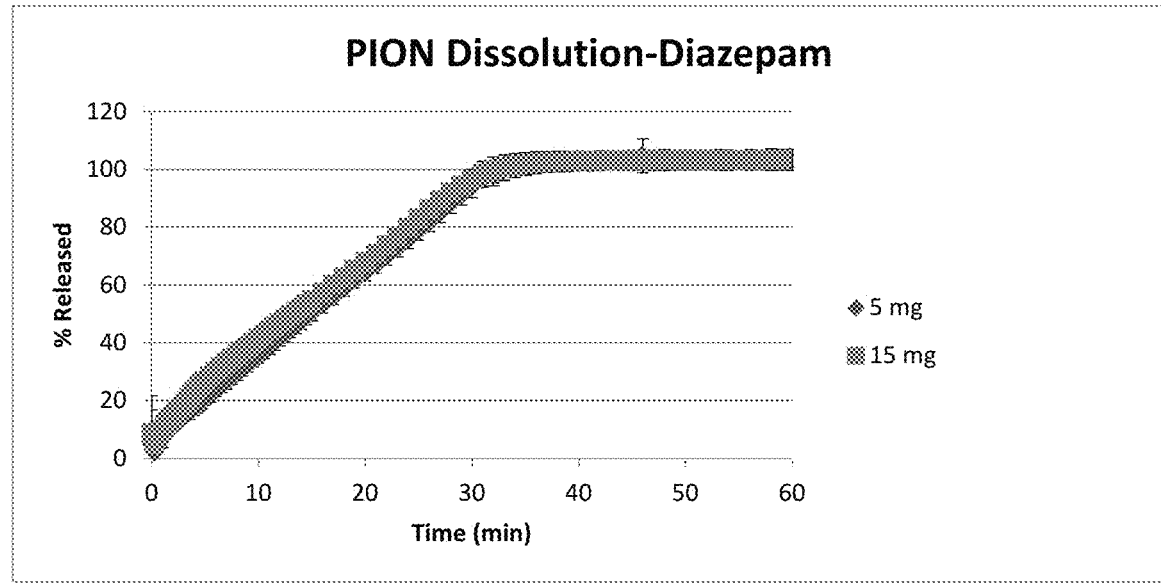
FIG. 5 is a graph of the average active dissolution profile for oral films containing 5 mg and 15 mg of diazepam measured by PION technology.

FIG. 4 is a graph showing the active dissolution profile of DBSF measured by traditional dissolution (n=6, 12M, 25° C.). FIG. 5 is a graph showing the active dissolution profile of DBSF measured by PION technology (n=6). A number of data points and a comparison of the results obtained by traditional dissolution and results obtained with PION technology are presented in Tables 4 and 5.

TABLE 4

Active Dissolution Rates and Comparison for DBSF Containing 5 mg Diazepam

| Time | Average % dissolved -- Traditional Dissolution | Average % dissolved -- PION Dissolution | {Rt − Tt} | (Rt − Tt)$^2$ |
|---|---|---|---|---|
| 5 | 22 | 21 | 1.316 | 1.7336 |
| 10 | 39 | 36 | 3.158 | 9.9751 |
| 15 | 56 | 50 | 5.683 | 32.3 |
| 20 | 73 | 64 | 9.0416 | 81.752 |
| 30 | 101 | 94 | 7.275 | 52.926 |
| Sum {Rt − Tt} | | | | 26.475 |
| Sum (Rt − Tt)$^2$ | | | | 178.69 |
| Sum Rt | | | | 291.48 |
| Similarity factor f2 | | | | 61 |
| Difference factor f1 | | | | 9 |

TABLE 5

Active Dissolution Rates and Comparison
for DBSF Containing 15 mg Diazepam

| Time | Average % dissolved -- Traditional Dissolution | Average % dissolved -- PION Dissolution | {Rt − Tt} | (Rt − Tt)² |
|---|---|---|---|---|
| 5 | 16 | 27 | 10.275 | 105.58 |
| 10 | 28 | 41 | 13.35 | 178.22 |
| 15 | 42 | 55 | 13.092 | 171.39 |
| 20 | 56 | 68 | 11.873 | 140.96 |
| 30 | 91 | 96 | 4.9333 | 24.338 |
| Sum {Rt − Tt} | | | | 53.523 |
| Sum (Rt − Tt)² | | | | 620.49 |
| Sum Rt | | | | 233.28 |
| Similarity factor f2 | | | | 48 |
| Difference factor f1 | | | | 23 |

According to the calculations presented in Tables 4 and 5 above, the active dissolution profiles for the 5 mg oral films are similar, while the active dissolution profiles for the 15 mg oral films are not. However, by using PION technology, the active dissolution profile is much more precise and enhanced with many more time intervals available. With traditional dissolution, the active dissolution profile includes only 7 data points, whereas the active dissolution profile obtained using PION technology has over five times that amount. In addition, data is available immediately when using PION technology, whereas the first data point using traditional dissolution is at 5 minutes. With these fast dissolving dosage forms, activity prior to the 5 minute mark can be a significant and differentiating factor.

Example 3—Dissolution Study of Oral Films Containing Riluzole

Oral thin films containing 50 mg of riluzole (ROSF) were prepared. Dissolution of 50 mg ROSF after storage for about 6 months at 25° C. was tested using traditional dissolution and PION technology in 0.1N HCL (a medium that mimics gastric conditions). The parameters used for traditional dissolution and PION technology for testing ROSF are presented in Table 3 above.

Figure 6:
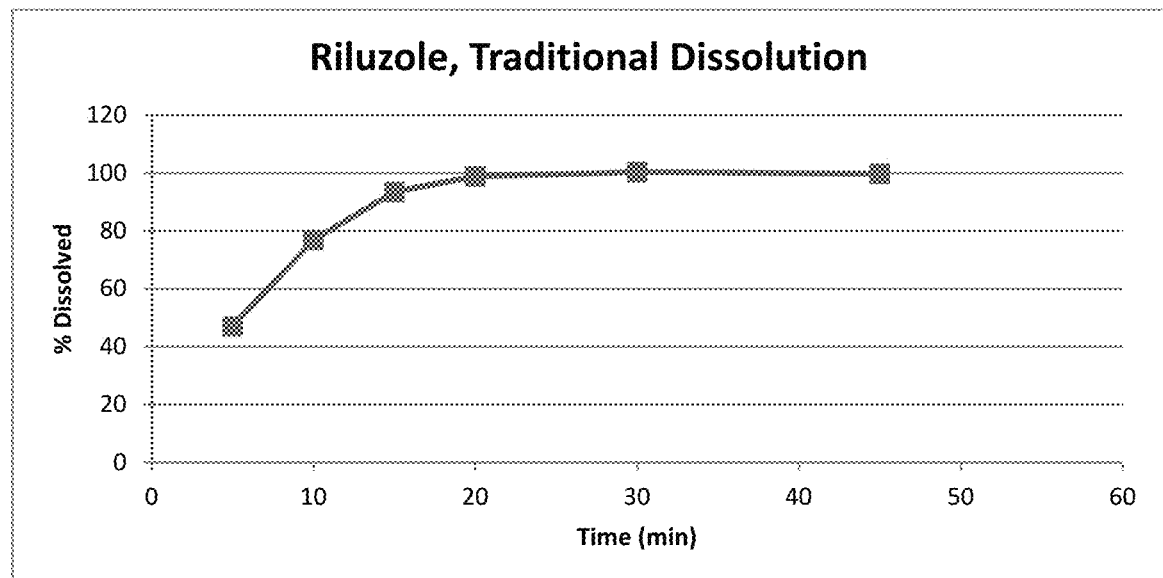
FIG. 6 is a graph of the average active dissolution profile for oral films containing 50 mg of riluzole measured by traditional dissolution.
Figure 7:
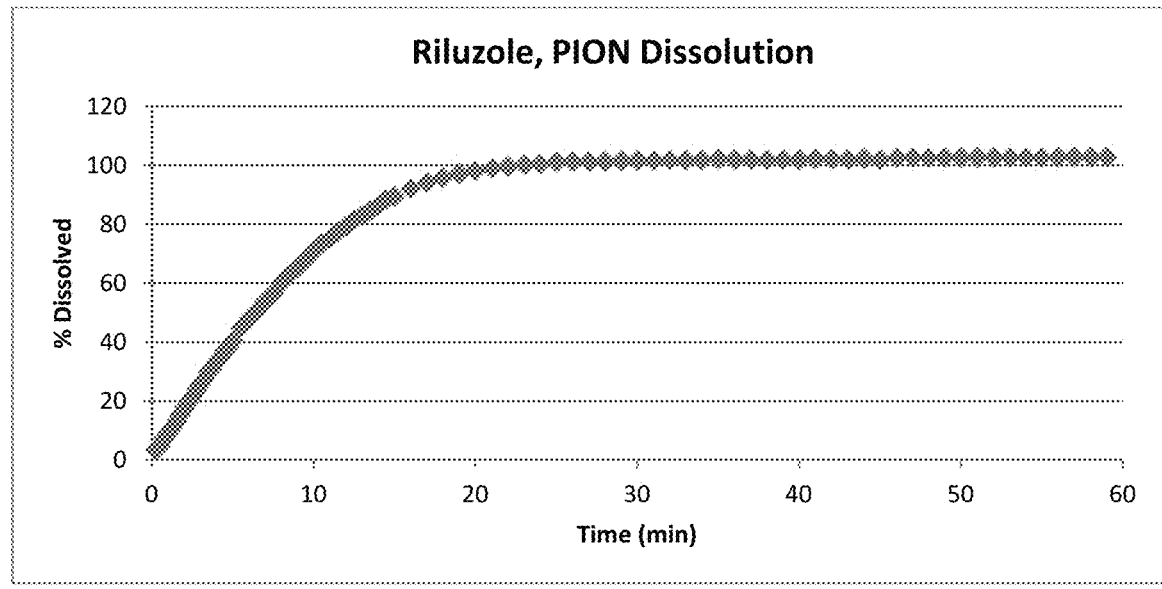
FIG. 7 is a graph of the average active dissolution profile for oral films containing 50 mg of riluzole measured by PION technology.

FIG. 6 is a graph of the active dissolution profile of ROSF measured by traditional dissolution testing. FIG. 7 is a graph of the active dissolution profile of ROSF measured by PION technology. A number of data points and a comparison of the results obtained by traditional dissolution and results obtained with PION technology are presented in Table 6.

TABLE 6

Active Dissolution Rates and Comparison for ROSF

| Time | Average % dissolved -- Traditional Dissolution | Average % dissolved -- PION Dissolution | {Rt − Tt} | (Rt − Tt)² |
|---|---|---|---|---|
| 5 | 47.0 | 40.4 | 6.6249 | 43.889 |
| 10 | 76.9 | 70.8 | 6.1846 | 38.25 |
| 15 | 93.5 | 89.5 | 4.0097 | 16.078 |
| Sum {Rt − Tt} | | | | 16.819 |
| Sum (Rt − Tt)² | | | | 98.217 |
| Sum Rt | | | | 217.43 |
| Similarity factor f2 | | | | 62 |
| Difference factor f1 | | | | 8 |

According to the calculations presented in Table 6 above, the active dissolution profiles for the 50 mg oral films containing riluzole are similar. However, by using PION technology, the active dissolution profile is much more precise and enhanced with many more time intervals available. With traditional dissolution, the active dissolution profile includes only 6 data points, whereas the active dissolution profile obtained using PION technology has over five times that amount. In addition, data is available immediately when using PION technology, whereas the first data point using traditional dissolution is at 5 minutes. With these fast dissolving dosage forms, activity prior to the 5 minute mark can be a significant and differentiating factor.

Example 4—Dissolution Study of Oral Films Containing Clobazam

Oral thin films containing clobazam (COSF) were prepared containing 5 mg, 10 mg and 20 mg of the active having compositions as shown in Table 7.

TABLE 7

Composition of COSF Formulations

| Component | % solids (w/w) | 5 mg COSF (mg) | 10 mg COSF (mg) | 20 mg COSF (mg) |
|---|---|---|---|---|
| Clobazam | 12.50 | 5.00 | 10.00 | 20.00 |
| Polyethylene oxide | 49.40 | 19.76 | 39.52 | 79.04 |
| Cellulose ether | 5.70 | 2.28 | 4.56 | 9.12 |
| Sugar alcohol | 13.80 | 5.52 | 11.04 | 22.08 |
| Flavoring | 6.00 | 2.40 | 4.80 | 9.60 |
| Artificial sweetener | 3.50 | 1.40 | 2.80 | 5.60 |
| Sodium phosphate dibasic | 2.90 | 1.16 | 2.32 | 4.64 |
| Food acid | 2.10 | 0.84 | 1.68 | 3.36 |
| Cooling agent | 2.00 | 0.80 | 1.60 | 3.20 |
| Bitter masker | 1.60 | 0.64 | 1.28 | 2.56 |
| Monoglyceride ester | 0.50 | 0.20 | 0.40 | 0.80 |
| TOTAL (% or mg) | 100.00 | 40.00 | 80.00 | 160.00 |

The COSF used in the examples herein contained clobazam having an average particle size D90 of 6-8 microns.

Dissolution of 5 mg and 20 mg COSF was tested using traditional dissolution and PION technology. The parameters used for traditional dissolution and PION technology for testing COSF are presented in Table 3 above.

FIG. 8 is a graph showing the active dissolution profile of 5 mg COSF measured by traditional dissolution after storage for about 24 months at 25° C. and 40° C. and 60 RH, shelf-life and accelerated conditions respectively. As shown therein, the films are nearly fully released at the very first sampling point. There is no information on the active dissolution profile at the very crucial time period before 10 minutes, when most of the dissolution is occurring. Also, the lack of precision of traditional dissolution is clearly visible in this graph where there is no detectable difference between the active dissolution profiles from 0-10 minutes for the two samples.

In contrast, FIGS. 9 and 10 show active dissolution profiles for COSF samples measured by PION technology. As shown in these figures, there is a clearly detectable difference between samples at differing storage conditions, as well as at different dosage amounts. FIG. 9 is a graph of the active dissolution profile of COSF measured by PION technology at different dosages and temperatures; FIG. 10 is an enhanced and smoothed curve of the same study as in FIG. 9. FIG. 10 plots the active dissolution profiles for these COSF dosages at different storage conditions, after storage conditions of about 12 months at about 25° C. and at about 40° C. from zero to ten minutes. A number of data points and a comparison of the results obtained at different temperatures using the PION technology are presented in Tables 8 and 9.

TABLE 8

Active Dissolution Rates and Comparison for 5 mg COSF

| Time | Average % dissolved at about 25° C. | Average % dissolved at 40° C. | {Rt − Tt} | (Rt − Tt)$^2$ |
|---|---|---|---|---|
| 0.17 | −4.4 | −3.3 | 1.13 | 1.29 |
| 0.67 | 4.5 | 23.9 | 19.45 | 378.37 |
| 1.08 | 38.1 | 59.4 | 21.32 | 454.56 |
| 1.5 | 67 | 81.2 | 14.17 | 200.86 |
| 1.92 | 84.4 | 93.4 | 9.01 | 81.22 |
| 2.5 | 97.4 | 102.4 | 4.98 | 24.78 |
| Sum {Rt − Tt} | | | | 70.07 |
| Sum (Rt − Tt)$^2$ | | | | 1141.1 |
| Sum Rt | | | | 287 |
| Similarity factor f2 | | | | 43 |
| Difference factor f1 | | | | 24 |

TABLE 9

Active Dissolution Rates and Comparison for 20 mg COSF

| Time | Average % dissolved at about 25° C. | Average % dissolved at 40° C. | {Rt − Tt} | (Rt − Tt)$^2$ |
|---|---|---|---|---|
| 1.5 | 3.8 | 6.3 | 2.57 | 6.60 |
| 2.5 | 18.2 | 33.7 | 15.52 | 240.9 |
| 3.5 | 46.1 | 68.2 | 22.12 | 489.13 |
| 4.5 | 69.5 | 85.9 | 16.37 | 268.06 |
| 5.5 | 83.4 | 93.7 | 10.29 | 105.85 |
| 6.5 | 91.1 | 97.3 | 6.20 | 38.44 |
| Sum {Rt − Tt} | | | | 73.07 |
| Sum (Rt − Tt)$^2$ | | | | 1149 |
| Sum Rt | | | | 312.1 |
| Similarity factor f2 | | | | 43 |
| Difference factor f1 | | | | 23 |

FIGS. 9 and 10 and the calculations presented in Tables 8 and 9 show the precision that is possible by using PION technology, including measuring data points in fractions of a minute. This produces identifiable measurable differences between oral films containing different amounts of active, and dosage forms under different storage conditions.

Figure 11:
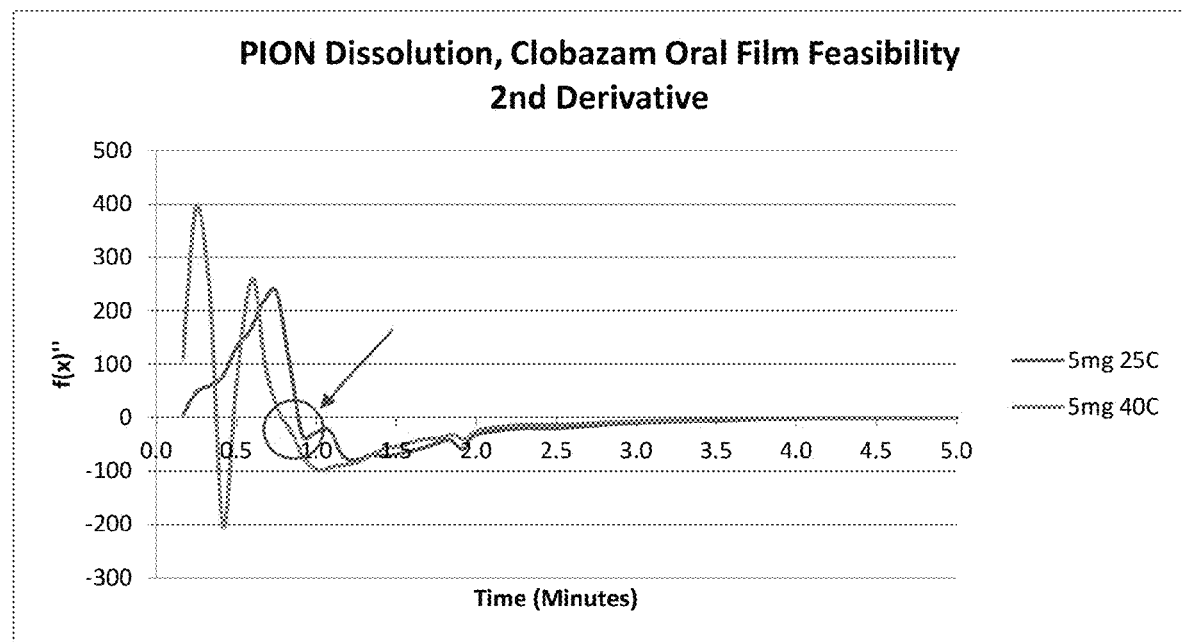
FIG. 11 is a graph of the second derivative values and inflection points (encircled) for the results of FIG. 9 for oral films containing 5 mg of clobazam.
Figure 12:
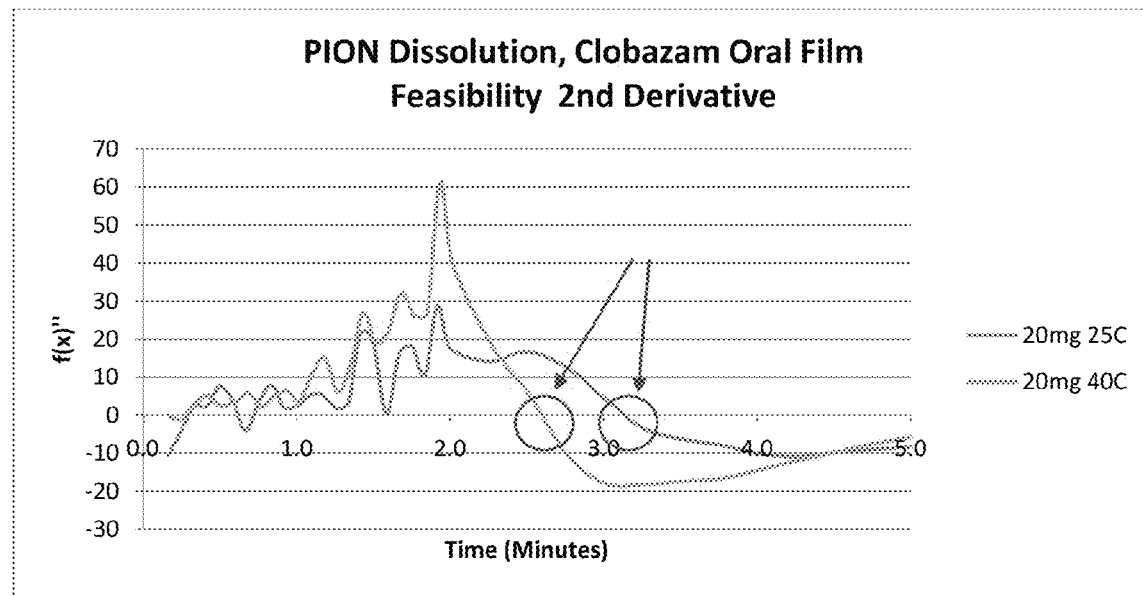
FIG. 12 is a graph of the second derivative values and inflection points (encircled) for the results of FIG. 9 for oral films containing 5 mg and 20 mg of clobazam.

FIGS. 11 and 12 plot the second derivatives of the active dissolution profiles measured by PION technology in FIGS. 9 and 10. With this, the calculation of the exact inflection point(s) (identified on the figures with arrows and encircled) is achievable.

Example 5: COSF Dosage Comparison

Oral thin films containing clobazam (COSF) were prepared containing 5 mg, 10 mg and 20 mg of the active having compositions as shown in Table 7. The films were stored for about 24 months and 60 RH at about 25° C. and then tested using PION technology to determine how the active dissolution profile varied between COSF containing different amounts of active. The parameters used for PION technology are presented in Table 3 above.

Figure 13:
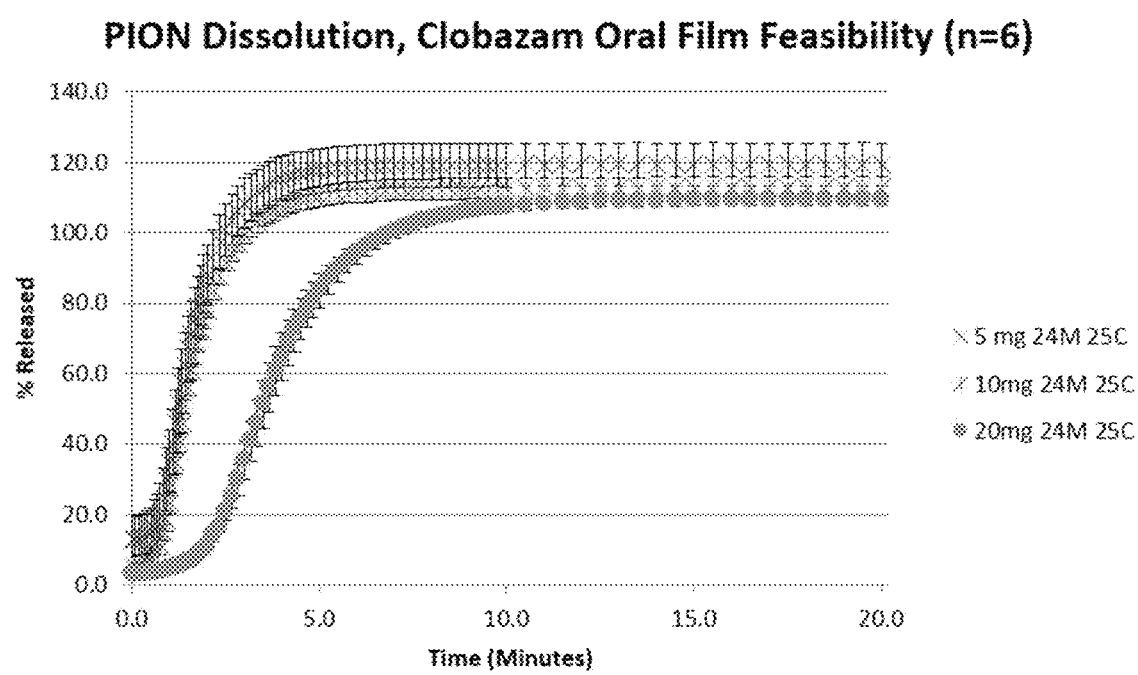
FIGS. 13 and 14 are graphs of average active dissolution profiles of oral films containing 5 mg, 10 mg and 20 mg of clobazam after storage for about 24 months and 60 RH at about 25° C. and about 40° C.
Figure 14:
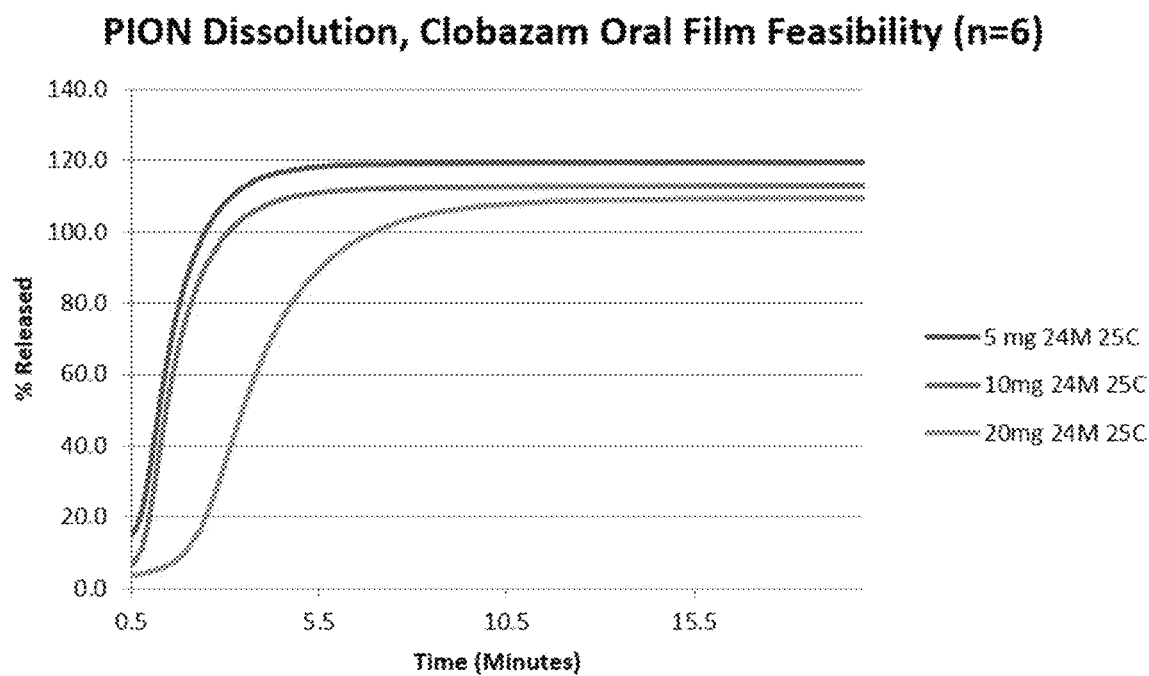

FIG. 13 graphs the data points actually obtained, while FIG. 14 is the smoothed curve of the points shown in FIG. 13. As shown in these figures, there is a detectable difference between the active dissolution profile of each of the films. The 5 mg COSF has the fastest release (steepest curve, reaching 100% at 2.5 minutes), then the 10 mg COSF (reaching 100% release at 3.0 minutes), and lastly the 20 mg COSF has the slowest release profile, approaching 100% after 7.0 minutes.

Figure 15:
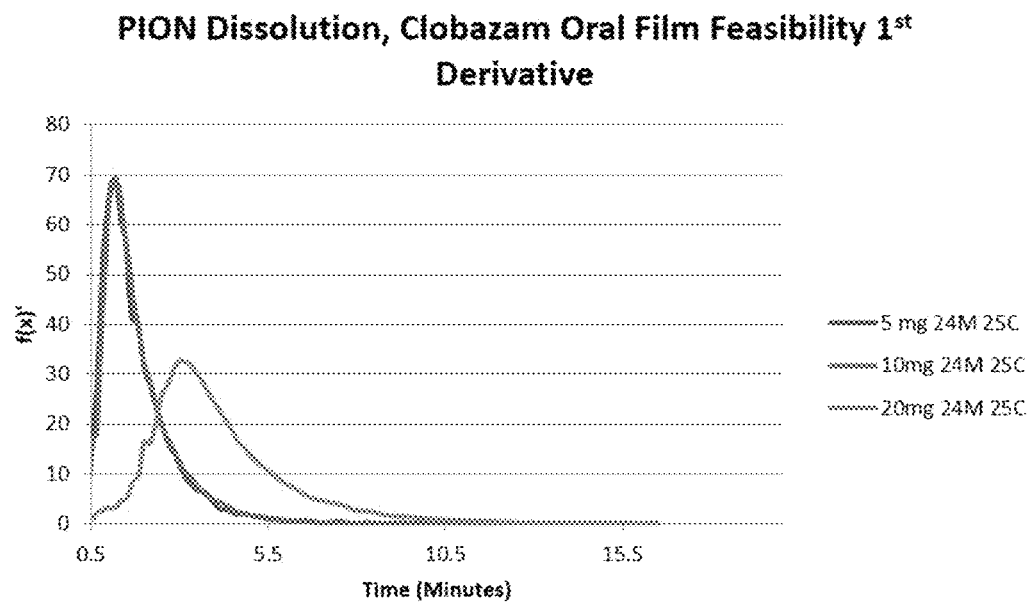
FIG. 15 is the $1^{st}$ derivative graph of the active dissolution profile of FIG. 13.

FIG. 15 is the 1$^{st}$ derivative graph of the active dissolution profile of FIG. 13. This graph provides information on the rate of release. The intensity and width of the first derivative is proportional to the rate of release. As indicated by the height and width of the 1st derivative curves in the figure, the 5 mg and 10 mg COSFs release faster and more fully within the first minute, while the 20 mg COSF releases slower, i.e., the curve is shorter and wider (lower intensity). For all curves, the first derivative approaches 0 as the release completes, and the concentration of drug in the vessel plateaus. The 5 mg and 10 mg COSF first derivative curves are substantially equivalent and plateau earlier than the 20 mg COSF curve.

Again as noted above with respect to FIG. 8, these differences shown in FIGS. 13, 14 and 15 would not be notable using traditional dissolution. It is only with the enhanced discriminating ability of PION technology that these differences can be detected and recorded.

Example 6: Comparison of COSF at Different Storage Conditions

The 5 mg, 10 mg and 20 mg COSF prepared as above were tested using PION technology either: 1) after storage for about 24 months and 60 RH at about 25° C.; 2) after storage for about 24 months and 60 RH at about 40° C.; or 3) upon completion of finished product (without storage time, T=about 0 months). The parameters used for PION technology are presented in Table 3 above. The active dissolution profiles were compared to determine how different storage conditions affect the rate of dissolution.

Figure 16:
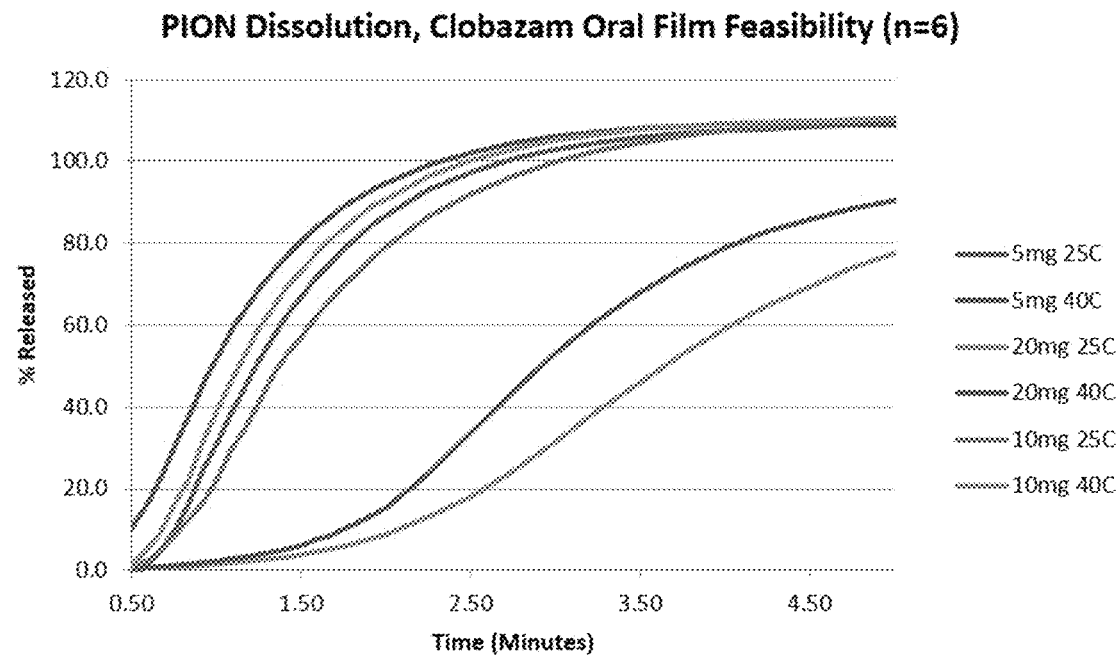
FIG. 16 is a graph of the active dissolution profiles of oral films containing 5 mg, 10 mg and 20 mg of clobazam after storage for about 24 months and 60 RH at about 25° C., and after storage for about 24 months and 60 RH at about 40° C., measured by PION technology.

FIG. 16 shows the active dissolution profiles for 5 mg, 10 mg and 20 mg COSF after storage for about 24 months and 60 RH at about 25° C., and after storage for about 24 months and 60 RH at about 40° C. For all film strengths, the active in samples that were stored at 40° C. dissolve faster than the active in the same dosage form that was stored at 25° C. The active in the 5 mg COSF stored at 40° C. dissolves the fastest, then 10 mg COSF stored at 40° C., while the 20 mg COSF samples had the slowest dissolution profiles. The enhanced discriminating ability of the PION system can be seen here. The active dissolution profiles obtained using PION technology are precise enough to show differences based on film strength and storage condition, both of which surprisingly affect dissolution rate of the active.

Statistical analysis, based on the FDA guidance, further demonstrates similarity or lack thereof between differing samples (strength/storage condition/age/etc.) With PION technology, similarity or lack of similarity is more evident than with traditional dissolution because of the enhanced precision, as well as the 1st derivative calculations. For example. statistical similarity is demonstrated between 5 mg and 10 mg at 25° C. and statistical similarity is not demonstrated between 5 mg and 10 mg at 25° C. vs. 40° C., as shown in Table 10. For similarity, $f_2$ (similarity factor) must be not less than 50 and $f_1$ (difference factor) must be not more than 15.

TABLE 10

Statistical Similarity Comparison

| Reference Sample | Test Sample | $f_2$ | $f_1$ |
|---|---|---|---|
| 5 mg ~24M, 25° C./60% RH | 10 mg ~24M, 25° C./60% RH | 55 | 15 |
| 5 mg ~24M, 40° C./75% RH | 10 mg ~24M, 40° C./75% RH | 46 | 20 |

Figure 18:
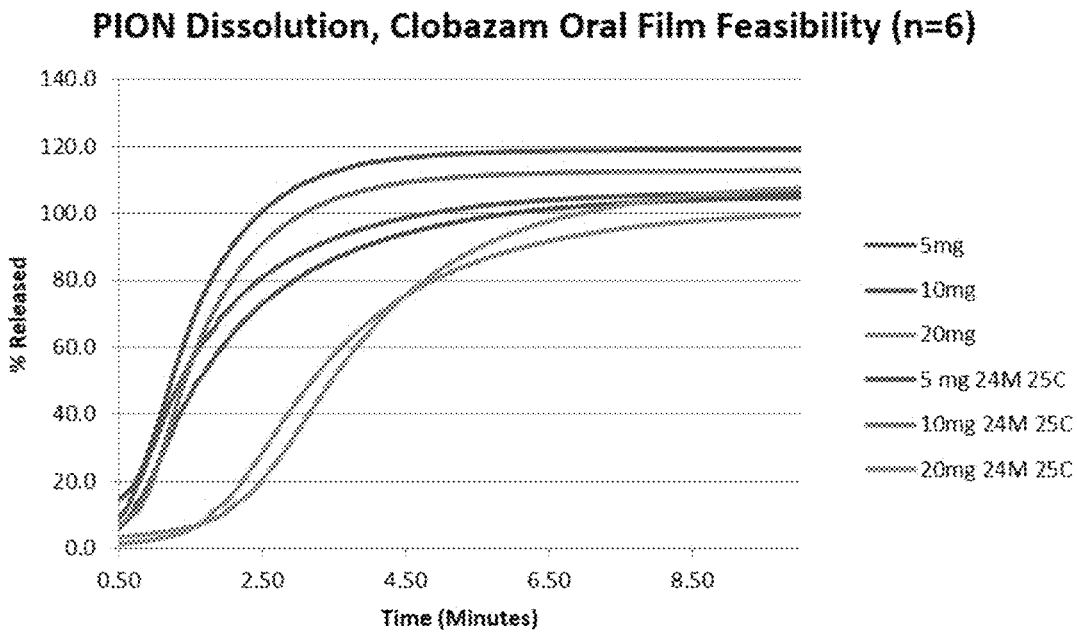
FIG. 18 is a graph of the active dissolution profiles of oral films containing 5 mg, 10 mg and 20 mg of clobazam after storage for about 24 months and 60 RH at about 25° C., and after manufacture, i.e., without storage, measured by PION technology.

FIG. 18 shows the active dissolution profiles for 5 mg, 10 mg and 20 mg COSF after storage for about 24 months and 60 RH at about 25° C., and without storage (T=about 0 months). For both 5 mg and 10 mg COSF, samples that were tested after storage dissolve faster than the finished product sample of the same strength (T=0).

As for statistical similarities, the active dissolution profiles for the finished product 5 mg and 10 mg COSF are not statistically similar to the equivalent stored samples. The active dissolution profile for the finished product 20 mg COSF samples is statistically similar to the stored 20 mg COSF samples.

TABLE 11

Statistical Similarity Comparison of Finished Product and Stored Product

| Reference Sample | Test Sample | $f_2$ | $f_1$ |
|---|---|---|---|
| 5 mg FP | 5 mg ~24M, 25° C./60% RH | 45 | 21 |
| 10 mg FP | 10 mg ~24M, 25° C./60% RH | 45 | 21 |
| 20 mg FP | 20 mg ~24M, 25° C./60% RH | 67 | 10 |

Figure 17:
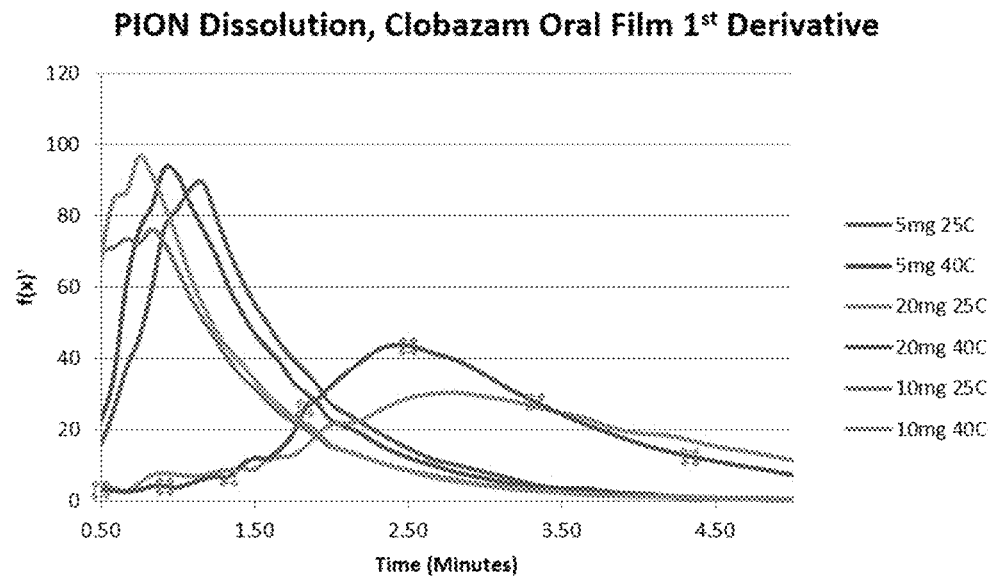
FIG. 17 is the $1^{st}$ derivative graph of the active dissolution profile of FIG. 16.

FIGS. 17 and 19 are the 1st derivative curves of the graphs of FIGS. 16 and 18, respectively. As indicated by the height and width of the 1st derivative curves in the figure, the 5 mg and 10 mg COSFs dissolve faster and more fully within the first minute, while the 20 mg COSF dissolves slower, i.e., the curve is shorter and wider (lower intensity). For all curves, the first derivative approaches 0 as dissolution is complete, and the concentration of drug in the vessel plateaus. The 5 mg and 10 mg COSF first derivative curves plateau earlier than the 20 mg COSF curve.

Example 7: Comparison of Media

The 5 mg, 10 mg and 20 mg COSF were prepared and tested (without a storage period) using PION technology to determine how media selection affect dissolution rates. The parameters used for PION technology are presented in Table 3 above. Accordingly, dissolution of the active in each film was tested in a bath of either: 0.1N HCL, 0.05 Molar solution of monobasic potassium phosphate adjusted to pH 6.8 with sodium hydroxide, or water.

Figure 20:
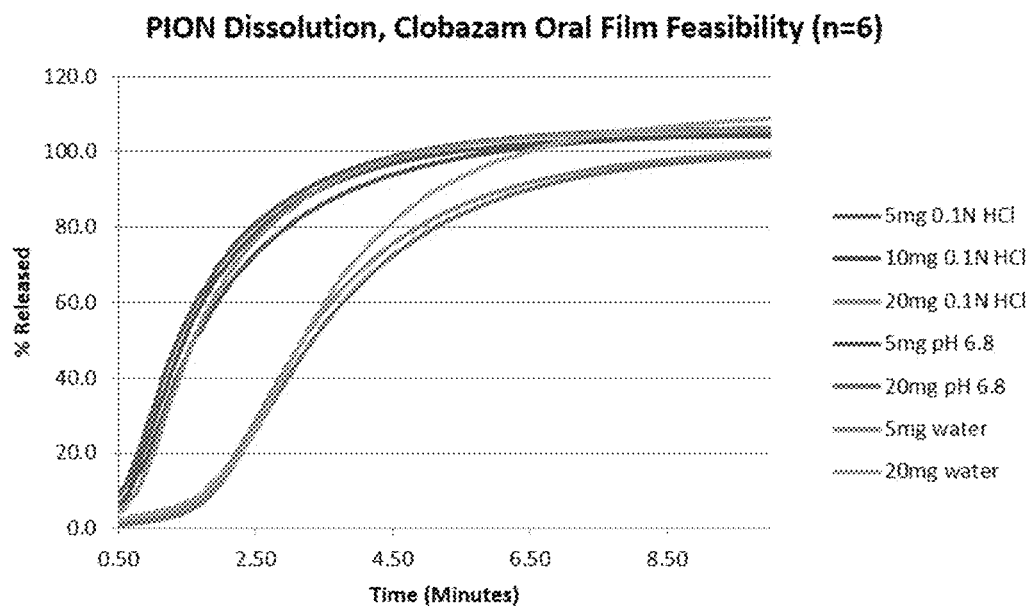
FIG. 20 is a graph of the active dissolution profiles of oral films containing 5 mg, 10 mg and 20 mg of clobazam in different media measured by PION technology.

FIG. 20 shows the active dissolution profiles for 5 mg, 10 mg and 20 mg COSF in different media. FIG. 21 is the 1st derivative curve of FIG. 20. Even with the enhanced discriminating ability of PION technology, the media selected does not affect the dissolution; samples of the same strength dissolved in the different media are statistically similar. With traditional dissolution, unless there is an obvious solubility issue, the active dissolution profile would not typically provide this enhanced information.

Example 8: Comparison of Release of Liquid Mix and Film

An experiment was designed to evaluate the impact of additional excipients on the release of the active. Specificity is an aspect of method development to ensure there is no interference of the quantitation of the active with any excipients contained within the drug product. Accordingly, active dissolution profiles for the following samples were measured by PION technology and presented in FIG. 22:
  5 mg COSF finished product (referred to as "5 mg nominal" in FIG. 22);
  liquid mix of the film composition before drying;
  placebo, which is a film with all excipients except for the active; and
  5 mg COSF finished product but with twice the amount of excipients (referred to as "5 mg w/2 placebos" in FIG. 22).

Figure 22:
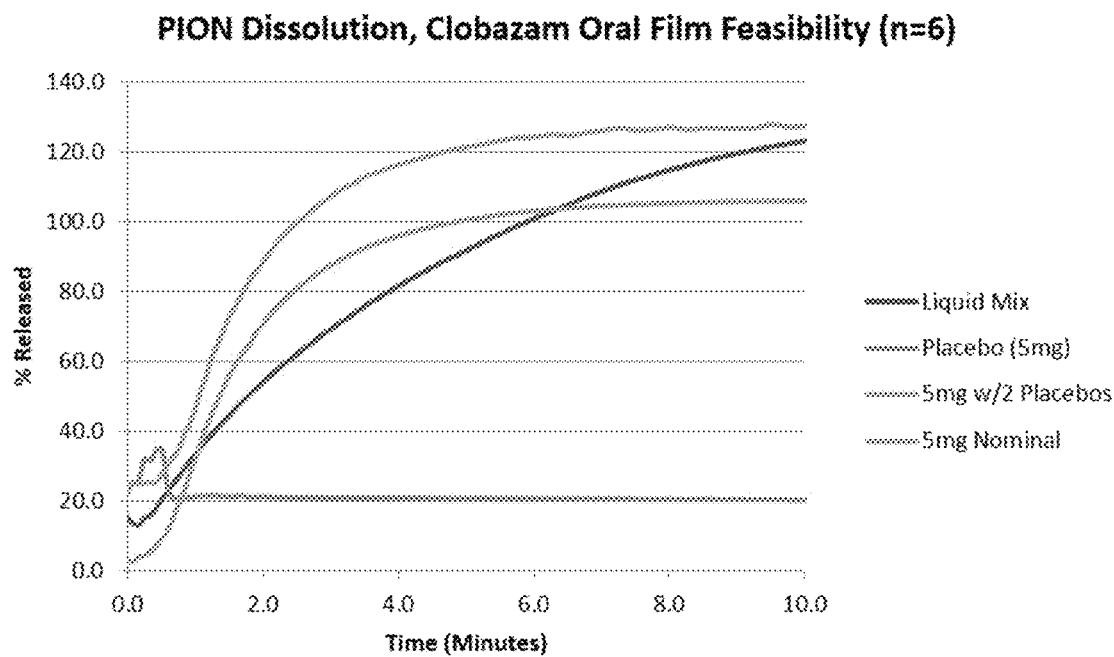
FIG. 22 is a graph of the active dissolution profiles for liquid mix containing clobazam, an oral film containing 5 mg of clobazam, and placebo, measured by PION technology.

As shown in FIG. 22, the placebo, which is the film without the active, shows some interference—about a 20% response. Thus, the excipients and film dosage form alone have an effect on the active dissolution profile. FIG. 23 is the 1st derivative curve of FIG. 22.

It was assumed that the active in liquid mix would dissolve faster than the active in the film, which needs to hydrate, swell and then release the active. However, unexpectedly, it was found that the film had a faster dissolution profile than the liquid mix. Based on these results, it is believed that the dry film absorbing moisture into the matrix facilitates the release and dissolution of the active.

Example 9: Evaluation of Substrate Performance

An experiment was conducted varying the substrate used during manufacture, specifically in the drying step, of an oral film containing 20 mg clobazam. In particular, the COSF 20 mg formulation was used to coat, using 40 mil gap, various substrates for comparative evaluation. The coated substrate was dried at 80° C. for 15 minutes. The dried coated substrate was evaluated and the results presented in Table 12.

TABLE 12

Properties and Comparison of Various Coated Substrates

| Substrate | Wet Uniformity | Dry Uniformity | Release (1-5; 1 is the best performing substrate) |
|---|---|---|---|
| Polyethylene terephthalate | Good | Good | 1 |
| Polyethylene terephthalate Corona Treated (Top) | Good | Good | 4 |
| Parchment Paper | Fair, paper not perfectly flat | Fair, paper not perfectly flat | 2 |
| Polyethylene terephthalate Corona Treated (Bottom) | Good | Good | 3 |
| Glass | Good | Good | 5 |

All of the dried film samples were able to be removed from the substrate after drying. However, there was a strong adherence at the edges of the film to the glass substrate, and moderate adherence for polyethylene terephthalate corona treated substrates. The best performing substrate was polyethylene terephthalate (untreated).

Example 10: Evaluation of Solubility of Clobazam in COSF Intermediate and Finished Products An experiment was conducted to assess the solubility of clobazam in the liquid mix (pre-drying) and oral films (COSF). Oral thin films containing 10 mg and 20 mg clobazam were prepared and then dissolved in 1.5 ml water. Two other samples were evaluated—one being the active in water (without the excipients added to the composition for oral films); and second being the liquid mix for the film but tested prior to film forming (i.e., drying). Table 13 presents the results of the evaluation.

TABLE 13

Solubility of Clobazam

| Sample | Theoretical Clobazam (mg/ml) in sample | Actual Clobazam (mg/ml) in supernatant | % Clobazam Dissolved in sample |
|---|---|---|---|
| COSF API 10 mg + 1.5 ml water | 6.70 | 0.11 | 1.576 |
| COSF 10 mg film + 1.5 ml water | 6.70 | 0.13 | 1.928 |
| COSF 20 mg film + 1.5 ml water | 13.30 | 0.15 | 1.115 |
| COSF wet mass | 37.50 | 0.39 | 1.027 |

As shown in the table above, about 1% to about 2% of clobazam dissolved, while over 98% remained dispersed, in each of the tested samples. The wet mass sample, which is the liquid mix composition of the film, has less active dissolved therein than the samples of the film that were subsequently hydrated with 1.5 ml water. This is because the drying process in the film forming method increases solubilization of the active in the formulation. The solubility is a function of the process of drying and the size (e.g., thickness) of the film. For example, the 10 mg film has a higher percent dissolved than the 20 mg film because the 10 mg film is thinner and thereby has a greater heat exposure per unit area during the drying process. Solubility is also proportionate to the taste profile of the oral film.

While there have been described what are presently believed to be the certain desirable embodiments of the invention, those skilled in the art will realize that changes and modifications may be made thereto without departing from the spirit of the invention, and it is intended to include all such changes and modifications as fall within the true scope of the invention.

What is claimed:

1. A self-supporting oral film for delivery of a desired amount of an active in an individual unit dose, said film comprising:
   a) a water-soluble polymer matrix, a water swellable polymer matrix, or a water-soluble and water swellable polymer matrix;
   b) the active being clobazam and having an average particle size D90 of less than about 160 microns; and
   c) an additive selected from the group consisting of a sweetener, a flavor, a flavor enhancer, a filler, a plasticizer, a dye, a pigment, a permeation enhancer, a buffer, a preservative, silicon dioxide, an anti-tacking agent, and any combination thereof;
   wherein, upon placing the film in a medium, about 60% or more of the active is dissolved in the medium after about 4 minutes.

2. The film of claim 1, wherein the active has an average particle size D90 of less than about 120 microns.

3. The film of claim 1, wherein the active has an average particle size D50 of less than about 30 microns.

4. The film of claim 2, wherein the active has an average particle size D10 of less than about 10 microns.

5. The film of claim 1, wherein the individual unit dose contains about 2 mg to about 20 mg of clobazam.

6. The film of claim 5, wherein the individual unit dose contains about 5 mg of clobazam.

7. The film of claim 5, wherein the individual unit dose contains about 10 mg of clobazam.

8. The film of claim 5, wherein the individual unit dose contains about 20 mg of clobazam.

9. A method of treating epilepsy and/or seizures in a human comprising administering to said human the oral film individual unit dose of claim 1.

10. The film of claim 1, wherein the water-soluble polymer matrix, the water swellable polymer matrix, or the water-soluble and water swellable polymer matrix comprise a polymer selected from polyethylene oxide (PEO), pullulan, hydroxypropylmethyl cellulose (HPMC), hydroxyethyl cellulose, hydroxypropyl cellulose (HPC), polyvinyl pyrrolidone, carboxymethyl cellulose, polyethylene glycol, xanthan gum, tragancanth gum, guar gum, acacia gum, arabic gum, polyacrylic acid, methyl-methacrylate copolymer, carboxyvinyl copolymers, starch, gelatin, and combinations thereof.

11. The film of claim 10, wherein the polymer is polyethylene oxide (PEO).

12. The film of claim 11, wherein the polyethylene oxide has a molecular weight of at least about 100,000.

13. The film of claim 11, wherein the polyethylene oxide has a molecular weight from about 100,000 to 300,000.

14. The film of claim 1, wherein the active has an average particle size D90 of about 8 microns to no more than about 160 microns.

* * * * *